United States Patent [19]

Morriello et al.

[11] Patent Number: 5,492,916
[45] Date of Patent: Feb. 20, 1996

[54] DI- AND TRI-SUBSTITUTED PIPERIDINES, PYRROLIDINES AND HEXAHYDRO-1H-AZEPINES PROMOTE RELEASE OF GROWTH HORMONE

[75] Inventors: Gregori J. Morriello, Belleville; Arthur A. Patchett, Westfield; Lihu Yang, Edison, all of N.J.

[73] Assignee: Merck & Co., Inc., Rahway, N.J.

[21] Appl. No.: 323,988

[22] Filed: Oct. 17, 1994

Related U.S. Application Data

[63] Continuation-in-part of Ser. No. 173,449, Dec. 23, 1993, abandoned.

[51] Int. Cl.⁶ .................. A61K 31/445; C07D 401/06; C07D 209/04
[52] U.S. Cl. .................. 514/318; 514/256; 514/319; 514/322; 514/323; 514/324; 514/326; 514/362; 514/363; 514/365; 514/372; 514/396; 514/414; 540/596; 540/597; 540/598; 540/601; 540/603; 540/607; 544/335; 546/193; 546/199; 546/201; 546/202; 546/205; 546/209; 546/210; 548/127; 548/128; 548/205; 548/214; 548/253; 548/306.1; 548/467; 548/468
[58] Field of Search .................. 540/596, 597, 540/598, 601, 602, 603, 607; 544/335; 546/193, 199, 201, 202, 205, 209, 210; 548/127, 128, 205, 214, 253, 306.1, 407, 468; 514/212, 318, 319, 323, 322, 324, 326, 362, 363, 365, 372, 396, 414

[56] References Cited

U.S. PATENT DOCUMENTS

| | | | |
|---|---|---|---|
| 3,239,345 | 3/1966 | Hodge et al. | 514/450 |
| 4,036,979 | 7/1977 | Asato | 514/443 |
| 4,411,890 | 10/1983 | Momany | 514/17 |
| 4,782,139 | 11/1988 | DiMarchi et al. | 530/407 |
| 5,137,872 | 8/1992 | Seely et al. | 514/12 |
| 5,164,368 | 11/1992 | Recker | 514/12 |
| 5,206,235 | 4/1993 | Fisher et al. | 514/213 |
| 5,283,241 | 2/1994 | Bochis et al. | 514/183 |
| 5,284,841 | 2/1994 | Chu et al. | 514/183 |
| 5,310,737 | 5/1994 | Fisher et al. | 514/215 |
| 5,317,017 | 5/1994 | Ok et al. | 514/211 |

FOREIGN PATENT DOCUMENTS

| | | |
|---|---|---|
| 0144230A3 | 6/1985 | European Pat. Off. . |
| 5163224 | 6/1993 | Japan . |
| WO94/08583 | 4/1994 | WIPO . |
| WO94/07486 | 4/1994 | WIPO . |
| WO94/13696 | 6/1994 | WIPO . |
| WO94/19367 | 9/1994 | WIPO . |

OTHER PUBLICATIONS

R. G. Smith, et al., *Science*, Reprint Series, 11 Jun. 1993, vol. 260, pp. 1640–1643 "A Nonpeptidyl Growth Hormone Secretagogue".

Ammann et al "IGF–I and pamidronate increase bone mineral density in ovariectomized adult rats" Am J. Physiology 265 pp. E770–E776 (1993).

Sakamoto, et al., *Chem. Abstracts*, 113(9) 73,560u (1990).

Horwell, et al., *Chem. Abstracts*, 113(15) 132,771p (1990).

*Primary Examiner*—Ceila Chang
*Attorney, Agent, or Firm*—J. Eric Thies; David L. Rose

[57] ABSTRACT

The present invention is directed to certain novel compounds identified as di- and tri-substituted piperidines, pyrrolidines, and hexahydro-1H-azepines of the general structural formula:

$$R_1 \overset{*}{-} \overset{H}{\underset{\underset{N}{\overset{|}{C=O}}}{\overset{|}{C}}} - \overset{H}{\underset{|}{N}} - \overset{O}{\underset{\|}{C}} - A - N \overset{R_4}{\underset{R_5}{}}$$

$$(CH_2)_n - N \diagdown \underset{Y}{\overset{}{-}} X$$

wherein $R_1$, $R_4$, $R_5$, A, X, Y, and n are as defined herein. These compounds promote the release of growth hormone in humans and animals. This property can be utilized to promote the growth of food animals to render the production of edible meat products more efficient, and in humans, to treat physiological or medical conditions characterized by a deficiency in growth hormone secretion, such as short stature in growth hormone deficient children, and to treat medical conditions which are improved by the anabolic effects of growth hormone. Growth hormone releasing compositions containing such di and tri substituted piperidines, pyrrolidines, and hexahydro-1H-azepines as the active ingredient thereof are also disclosed.

10 Claims, No Drawings

DI- AND TRI-SUBSTITUTED PIPERIDINES, PYRROLIDINES AND HEXAHYDRO-1H-AZEPINES PROMOTE RELEASE OF GROWTH HORMONE

CROSS REFERENCE TO RELATED APPLICATIONS

This application is a continuation-in-part of application Ser. No. 08/173,449, filed Dec. 23, 1993, now abandoned.

BACKGROUND OF THE INVENTION

Growth hormone, which is secreted from the pituitary, stimulates growth of all tissues of the body that are capable of growing. In addition, growth hormone is known to have the following basic effects on the metabolic processes of the body:

1. Increased rate of protein synthesis in all cells of the body;
2. Decreased rate of carbohydrate utilization in cells of the body;
3. Increased mobilization of free fatty acids and use of fatty acids for energy.

A deficiency in growth hormone secretion can result in various medical disorders, such as dwarfism.

Various ways are known to release growth hormone. For example, chemicals such as arginine, L-3,4-dihydroxyphenylalanine (L-DOPA), glucagon, vasopressin, and insulin induced hypoglycemia, as well as activities such as sleep and exercise, indirectly cause growth hormone to be released from the pituitary by acting in some fashion on the hypothalamus perhaps either to decrease somatostatin secretion or to increase the secretion of the known secretagogue growth hormone releasing factor (GRF) or an unknown endogenous growth hormone-releasing hormone or all of these.

In cases where increased levels of growth hormone were desired, the problem was generally solved by providing exogenous growth hormone or by administering an agent which stimulated growth hormone production and/or release. In either case the peptidyl nature of the compound necessitated that it be administered by injection. Initially the source of growth hormone was the extraction of the pituitary glands of cadavers. This resulted in a very expensive product and carried with it the risk that a disease associated with the source of the pituitary gland could be transmitted to the recipient of the growth hormone. Recently, recombinant growth hormone has become available which, while no longer carrying any risk of disease transmission, is still a very expensive product which must be given by injection or by a nasal spray.

Other compounds have been developed which stimulate the release of endogenous growth hormone such as analogous peptidyl compounds related to GRF or the peptides of U.S. Pat. No. 4,411,890. These peptides, while considerably smaller than growth hormones are still susceptible to various proteases. As with most peptides, their potential for oral bioavailability is low. The instant compounds are non-peptide analogs for promoting the release of growth hormone which are stable in a variety of physiological environments and which may be administered parenterally, nasally or by the oral route.

SUMMARY OF THE INVENTION

The instant invention is directed to certain di- and tri-substituted piperidine, pyrrolidine and hexahydro-1H-azepine compounds which have the ability to stimulate the release of natural or endogenous growth hormone. The compounds thus have the ability to be used to treat conditions which require the stimulation of growth hormone production or secretion such as in humans with a deficiency of natural growth hormone or in animals used for food or wool production where the stimulation of growth hormone will result in a larger, more productive animal. Thus, it is an object of the instant invention to describe the di- and tri-substituted piperidine, pyrrolidine and hexahydro-1H-azepine compounds. It is a further object of this invention to describe procedures for the preparation of such compounds. A still further object is to describe the use of such compounds to increase the secretion of growth hormone in humans and animals. A still further object of this invention is to describe compositions containing the di- and tri-substituted piperidine, pyrrolidine and hexahydro-1H-azepine compounds for the use of treating humans and animals so as to increase the level of growth hormone secretions. Further objects will become apparent from a reading of the following description.

DESCRIPTION OF THE INVENTION

The novel di- and tri- substituted piperidines, pyrrolidines and hexahydro-1H-azepines of the instant invention are described by structural Formula I:

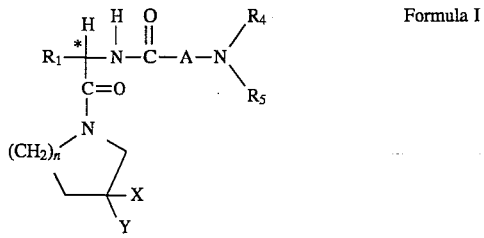

wherein:

$R_1$ is selected from the group consisting of: $C_1$–$C_{10}$ alkyl, aryl, aryl($C_1$–$C_6$ alkyl), ($C_3$–$C_7$ cycloalkyl) ($C_1$–$C_6$ alkyl)-, ($C_1$–$C_5$ alkyl)-K—($C_1$–$C_5$ alkyl)-, aryl ($C_0$–$C_5$ alkyl)-K—($C_1$–$C_5$ alkyl)-, and ($C_3$–$C_7$ cycloalkyl)($C_0$–$C_5$ alkyl)-K—($C_1$–$C_5$ alkyl)-, where K is O, S(O)$_m$, N($R_2$)C(O), C(O)N($R_2$), OC(O), C(O)O, —$CR_2$═$CR_2$—, or —C≡C—, where aryl is selected from: phenyl, naphthyl, indolyl, azaindole, pyridyl, benzothienyl, benzofuranyl, thiazolyl, and benzimidazolyl, and $R_2$ and alkyl may be further substituted by 1 to 9 halogen, S(O)$_m$$R_{2a}$, 1 to 3 of O$R_{2a}$ or C(O)O$R_{2a}$, and aryl may be further substituted by 1 to 3 of $C_1$–$C_6$ alkyl, 1 to 3 of halogen, 1 to 2 of O$R_2$, methylenedioxy, —S(O)$_m$$R_2$, 1 to 2 of —$CF_3$, —$OCF_3$, nitro, —N($R_2$)C(O)($R_2$), —C(O)O$R_2$, —C(O)N($R_2$)($R_2$), -1H-tetrazol-5-yl, —$SO_2$N($R_2$)($R_2$), —N($R_2$)$SO_2$ phenyl, or —N($R_2$)$SO_2$$R_2$;

$R_2$ is selected from: hydrogen, $C_1$–$C_6$ alkyl, and $C_3$–$C_7$ cycloalkyl, and where two $C_1$–$C_6$ alkyl groups are present on one atom, they may be optionally joined to form a $C_3$–$C_8$ cyclic ring, optionally including oxygen, sulfur or N$R_{3a}$, where $R_{3a}$ is hydrogen, or $C_1$–$C_6$ alkyl, optionally substituted by hydroxyl;

X is selected from: hydrogen, —C≡N, —($CH_2$)$_q$N($R_2$)C(O)$R_2$, —($CH_2$)$_q$N($R_2$)C(O)($CH_2$)$_t$aryl, —($CH_2$)$_q$N($R_2$)$SO_2$($CH_2$)$_t$aryl, —($CH_2$)$_q$N($R_2$)$SO_2$$R_2$, —($CH_2$)$_q$N($R_2$)C(O)N($R_2$)($CH_2$)$_t$aryl, —($CH_2$)$_q$N($R_2$)C(O)N($R_2$)($R_2$), —$(CH_2)_qC(O)N(R_2)(R_2)$,
—$(CH_2)_qC(O)N(R_2)(CH_2)_t$aryl, —$(CH_2)_qC(O)OR_2$,
—$(CH_2)_qC(O)O(CH_2)_t$aryl, —$(CH_2)_qOR_2$,
—$(CH_2)_qOC(O)R_2$, —$(CH_2)_qOC(O)(CH_2)_t$aryl,
—$(CH_2)_qOC(O)N(R_2)(CH_2)_t$aryl,
—$(CH_2)_qOC(O)N(R_2)(R_2)$, —$(CH_2)_qC(O)R_2$,
—$(CH_2)_qC(O)(CH_2)_t$aryl, —$(CH_2)_qN(R_2)C(O)OR_2$,
—$(CH_2)_qN(R_2)SO_2N(R_2)(R_2)$, —$(CH_2)_qS(O)_mR_2$, and
—$(CH_2)_qS(O)_m(CH_2)_t$aryl, where an $R_2$, $(CH_2)_q$ and $(CH_2)_t$ group may be optionally substituted by 1 to 2 $C_1$–$C_4$ alkyl, hydroxyl, $C_1$–$C_4$ lower alkoxy, carboxyl, $CONH_2$, $S(O)_mCH_3$, carboxylate $C_1$–$C_4$ alkyl esters, or 1H-tetrazol-5-yl, and aryl is phenyl, naphthyl, pyridyl, thiazolyl, or 1H-tetrazol-5-yl groups which may be optionally substituted by 1 to 3 halogen, 1 to 3 —$OR_2$, —$CON(R_2)(R_2)$, —$C(O)OR_2$, 1 to 3 $C_1$–$C_4$ alkyl, —$S(O)_mR_2$, or 1H-tetrazol-5-yl;

Y is selected from: hydrogen, $C_1$–$C_{10}$ alkyl, —$(CH_2)_t$aryl, —$(CH_2)_q(C_3$–$C_7$ cycloalkyl), —$(CH_2)_q$—K—$(C_1$–$C_6$ alkyl), —$(CH_2)_q$—K—$(CH_2)_t$aryl, —$(CH_2)_q$—K—$(CH_2)_t(C_3$–$C_7$ cycloalkyl containing O, NR2, S), and —$(CH_2)_q$—K—$(CH_2)_t(C_3$–$C_7$ cycloalkyl), where K is O, $S(O)_m$, $C(O)NR_2$, $CH=CH$, $C\equiv C$, $N(R_2)C(O)$, $C(O)NR_2$, $C(O)O$, or $OC(O)$, and where the alkyl, $R_2$, $(CH_2)_q$ and $(CH_2)_t$ groups may be optionally substituted by $C_1$–$C_4$ alkyl, hydroxyl, $C_1$–$C_4$ lower alkoxy, carboxyl, —$CONH_2$ or carboxylate $C_1$–$C_4$ alkyl esters, and aryl is phenyl, naphthyl, pyridyl, 1H-tetrazol-5-yl, thiazolyl, imidazolyl, indolyl, pyrimidinyl, thiadiazolyl, pyrazolyl, oxazolyl, isoxazolyl, thiopheneyl, quinolinyl, pyrazinyl, or isothiazolyl which is optionally substituted by 1 to 3 halogen, 1 to 3 —$OR_2$, —$C(O)OR_2$, —$C(O)N(R2)(R2)$, nitro, cyano, benzyl, 1 to 3 $C_1$–$C_4$ alkyl, —$S(O)_mR_2$, or 1H-tetrazol-5-yl, with the proviso that if X is hydrogen, Y is other than hydrogen;

$R_4$ and $R_5$ are independently hydrogen, $C_1$–$C_6$ alkyl, or substituted $C_1$–$C_6$ alkyl where the substituents may be 1 to 5 halo, 1 to 3 hydroxy, 1 to 3 $C_1$–$C_{10}$ alkanoyloxy, 1 to 3 $C_1$–$C_6$ alkoxy, phenyl, phenyloxy, 2-furyl, $C_1$–$C_6$ alkoxycarbonyl, $S(O)_m(C_1$–$C_6$ alkyl), or $R_4$ and $R_5$ may be taken together to form —$(CH_2)_d$—$L_a(CH_2)_e$— where $L_a$ is —$C(R_2)_2$—, O, $S(O)_m$ or $N(R_2)$, d and e are independently 1 to 3 and $R_2$ is as defined above;

A is:

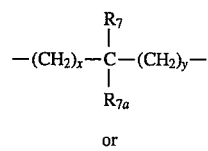

or $$-Z-(CH_2)_x-\underset{R_{7a}}{\overset{R_7}{C}}-(CH_2)_y-$$

where x and y are independently 0, 1, 2 or 3;

Z is N—$R_{6a}$ or O, where $R_{6a}$ is hydrogen or $C_1$–$C_6$ alkyl;

$R_7$ and $R_{7a}$ are independently hydrogen, $C_1$–$C_6$ alkyl, trifluoromethyl, phenyl, or substituted $C_1$–$C_6$ alkyl where the substituents are imidazolyl, phenyl, indolyl, p-hydroxyphenyl, $OR_2$, $S(O)_mR_2$, $C(O)OR_2$, $C_3$–$C_7$ cycloalkyl, $N(R_2)(R_2)$, $C(O)N(R_2)(R2)$, or $R_7$ and $R_{7a}$ may independently be joined to one or both of $R_4$ and $R_5$ groups to form an alkylene bridge between the terminal nitrogen and the alkyl portion of the $R_7$ or $R_{7a}$ groups, wherein the bridge contains 1 to 5 carbons atoms, or $R_7$ and $R_{7a}$ can be joined to one another to form $C_3$–$C_7$ cycloalkyl;

m is 0, 1, or 2;

n is 1, 2, or 3;

q is 0, 1, 2, 3, or 4;

t is 0, 1, 2, or 3;

and pharmaceutically acceptable salts and individual diastereomers thereof.

In the above structural formula and throughout the instant specification, the following terms have the indicated meanings:

When n is 1 a pyrrolidine ring is formed, when n is 2 a piperidine ring is formed, and when n is 3 the ring is designated a hexahydro-1-H-azepine.

The alkyl groups specified above are intended to include those alkyl groups of the designated length in either a straight or branched configuration and if two carbon atoms or more they may include a double or a triple bond. Exemplary of such alkyl groups are methyl, ethyl, propyl, isopropyl, butyl, sec-butyl, tertiary butyl, pentyl, isopentyl, hexyl, isohexyl, allyl, propargyl, and the like.

The alkoxy groups specified above are intended to include those alkoxy groups of the designated length in either a straight or branched configuration and if two or more carbon atoms in length, they may include a double or a triple bond. Exemplary of such alkoxy groups are methoxy, ethoxy, propoxy, isopropoxy, butoxy, isobutoxy, tertiary butoxy, pentoxy, isopentoxy, hexoxy, isohexoxy allyloxy, propargyloxy, and the like.

The term "halogen" is intended to include the halogen atom fluorine, chlorine, bromine and iodine.

The term "aryl" within the present invention, unless otherwise specified, is intended to include aromatic rings, such as carbocyclic and heterocyclic aromatic rings selected the group consisting of: phenyl, naphthyl, pyridyl, 1-H-tetrazol-5-yl, thiazolyl, imidazolyl, indolyl, pyrimidinyl, thiadiazolyl, pyrazolyl, oxazolyl, isoxazolyl, thiopheneyl, quinolinyl, pyrrazinyl, or isothiazolyl, which may be optionally substituted by 1 to 3 of $C_1$–$C_6$ alkyl, 1 to 3 of halogen, 1 to 2 of $OR_2$, methylenedioxy, —$S(O)_mR_2$, 1 to 2 of —$CF_3$, —$OCF_3$, nitro, —$N(R_2)C(O)(R_2)$, —$C(O)OR_2$, —$C(O)N(R_2)(R_2)$, -1H-tetrazol-5-yl, —$SO_2N(R_2)(R_2)$, —$N(R_2)SO_2$ phenyl, or —$N(R_2)SO_2R_2$, wherein $R_2$ is as defined herein.

Certain of the above defined terms may occur more than once in the above formula and upon such occurrence each term shall be defined independently of the other.

Preferred compounds of the instant invention include those of Formula Ia:

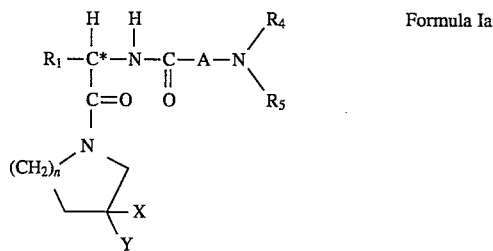

Formula Ia wherein:

$R_1$ is selected from the group consisting of: $C_1$–$C_{10}$ alkyl, aryl ($C_1$–$C_4$ alkyl)-, $C_3$–$C_6$ cycloalkyl ($C_1$–$C_4$ alkyl)-, ($C_1$–$C_4$ alkyl)-K—($C_1$–$C_2$ alkyl)-, aryl ($C_0$–$C_2$ alkyl)-K—($C_1$–$C_2$ alkyl)-, and ($C_3$–$C_7$ cycloalkyl)($C_0$–$C_2$ alkyl)-K—(C$_1$-C$_2$ alkyl)-, where K is O, S(O)$_m$, OC(O), or C(O)O, and the alkyl groups may be further substituted by 1 to 7 halogen, S(O)$_m$R$_2$, 1 to 3 OR$_2$ or C(O)OR$_2$, and aryl is phenyl, naphthyl, indolyl, pyridyl, benzimidazolyl, azaindoleyl, benzothienyl or benzofuranyl which may be further substituted by 1–2 C$_1$-C$_4$ alkyl, 1 to 2 halogen, 1 to 2 —OR$_2$, —S(O)$_m$R$_2$, or —C(O)OR$_2$;

R$_2$ is hydrogen, C$_1$-C$_6$ alkyl, or C$_3$-C$_7$ cycloalkyl, and where two C$_1$-C$_6$ alkyl groups are present on one atom they may be optionally joined to form a C$_4$-C$_7$ cyclic ring optionally including oxygen, sulfur or NR$_{3a}$;

R$_{3a}$ is hydrogen, or C$_1$-C$_4$ alkyl; X is selected from: hydrogen, —(CH$_2$)$_q$N(R$_2$)C(O)R$_2$,
—(CH$_2$)$_q$N(R$_2$)C(O)(CH$_2$)$_t$aryl,
—(CH$_2$)$_q$N(R$_2$)C(O)OR$_2$,
—(CH$_2$)$_q$N(R$_2$)SO$_2$(CH$_2$)$_t$aryl, —(CH$_2$)$_q$N(R$_2$)SO$_2$R$_2$,
—(CH$_2$)$_q$N(R$_2$)C(O)N(R$_2$)(CH$_2$)$_t$aryl,
—(CH$_2$)$_q$N(R$_2$)C(O)N(R$_2$)(R$_2$),
—(CH$_2$)$_q$C(O)N(R$_2$)(R$_2$),
—(CH$_2$)$_q$C(O)N(R$_2$)(CH$_2$)$_t$aryl, —(CH$_2$)$_q$C(O)OR$_2$,
—(CH$_2$)$_q$C(O)O(CH$_2$)$_t$aryl, —(CH$_2$)$_q$OC(O)R$_2$,
—(CH$_2$)$_q$OC(O)(CH$_2$)$_t$aryl, —(CH$_2$)$_q$S(O)mR$_2$, and
—(CH$_2$)$_q$S(O)m(CH$_2$)$_t$aryl, where an R$_2$ group may be optionally substituted by hydroxyl, carboxyl, CONH$_2$, S(O)$_m$CH$_3$, carboxylate C$_1$-C$_4$ alkyl esters, or tetrazole, and aryl is phenyl, naphthyl, pyridyl or 1-H-tetrazolyl which may be optionally substituted by 1 to 2 halogen, 1 to 2 —OR$_2$, —CONH$_2$, —C(O)OR$_2$, 1 to 3 C$_1$-C$_4$ alkyl, —S(O)$_m$R$_2$, or 1H-tetrazole-5-yl;

Y is selected from: hydrogen, C$_1$-C$_8$ alkyl, (CH$_2$)$_t$aryl, —(CH$_2$)$_q$(C$_5$-C$_6$ cycloalkyl), —(CH$_2$)$_q$—K—(C$_1$-C$_6$ alkyl), —(CH$_2$)$_q$—K—(CH$_2$)$_t$aryl, —(CH$_2$)$_q$—K—(CH$_2$)$_t$(C$_3$-C$_7$ cycloalkyl containing O, NR$_2$, or S), and —(CH$_2$)$_q$—K—(CH$_2$)$_t$ (C$_5$-C$_6$ cycloalkyl), where K is O or S(O)m and where the alkyl groups may be optionally substituted by hydroxyl, carboxyl, CONH$_2$, carboxylate C$_1$-C$_4$ alkyl esters or 1H-tetrazole-5-yl and aryl is phenyl, naphthyl, pyridyl, 1-H-tetrazolyl, thiazolyl, imidazolyl, indolyl, pyrimidinyl, thiadiazolyl, pyrazolyl, oxazolyl, isoxazolyl, or thiopheneyl which is optionally substituted by 1 to 3 halogen, 1 to 3 —OR$_2$, —C(O)OR$_2$, —C(O)N(R$_2$)(R$_2$), cyano, 1 to 2 C$_1$-C$_4$ alkyl, benzyl, —S(O)$_m$R$_2$, or 1H-tetrazol-5-yl, with the proviso that if X is hydrogen, Y is other than hydrogen;

R$_4$ and R$_5$ are independently hydrogen, C$_1$-C$_6$ alkyl, or substituted C$_1$-C$_6$ alkyl where the substituents may be 1 to 5 halo, 1 to 3 hydroxyl, S(O)m (C$_1$-C$_6$ alkyl) or phenyl;

A is:

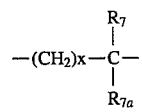

where x is 0, or 1;

R$_7$ and R$_{7a}$ are independently hydrogen C$_1$-C$_6$ alkyl, trifluoromethyl, phenyl, substituted C$_1$-C$_6$ alkyl where the substituents are imidazolyl, phenyl, indolyl, p-hydroxyphenyl, OR$_2$, S(O)mR$_2$, C(O)OR$_2$, C$_5$-C$_7$ cycloalkyl, —N(R$_2$)(R$_2$), —C(O)N(R$_2$)(R$_2$); or R$_7$ and R$_{7a}$ can independently be joined to one of R$_4$ or R$_5$ to form alkylene bridges between the terminal nitrogen and the alkyl portion of R$_7$ or R$_{7a}$ groups to form 5 or 6 membered rings; or R$_7$ and R$_{7a}$ can be joined to one another to form a C$_3$ cycloalkyl;

n is 2;

m is 0, 1, or 2;

q is 0, 1, 2, or 3;

t is 0, 1, 2, or 3;

and pharmaceutically acceptable salts and individual diastereomers thereof.

More preferred compounds of the instant invention include those of Formula Ib:

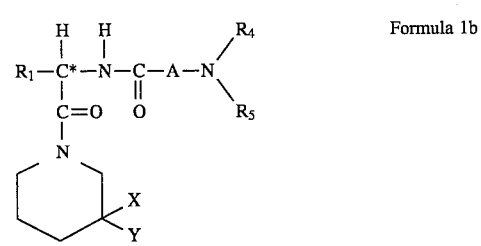

Formula Ib wherein:

R$_1$ is selected from the group consisting of: C$_1$-C$_{10}$ alkyl, aryl (C$_1$-C$_3$ alkyl)-, (C$_3$-C$_7$ cycloalkyl)(C$_1$-C$_3$ alkyl)-, and aryl (C$_0$-C$_1$ alkyl)-K—(C$_1$-C$_2$ alkyl)-, where K is O or S(O)$_m$ and the aryl is phenyl, pyridyl, naphthyl, indolyl, azaindolyl, or benzimidazolyl which is optionally substituted by 1–2 C$_1$-C$_4$ alkyl, 1 to 2 halogen, 1 to 2 OR$_2$, S(O)$_m$R$_2$, or C(O)OR$_2$;

R$_2$ is hydrogen, C$_1$-C$_6$ alkyl, or C$_3$-C$_7$ cycloalkyl, and where two C$_1$-C$_6$ alkyl groups are present on one atom they may be optionally joined to form a C$_5$-C$_7$ cyclic ring optionally including oxygen, sulfur or NR$_{3a}$;

R$_{3a}$ is hydrogen, or C$_1$-C$_4$ alkyl;

X is selected from: hydrogen, —(CH$_2$)$_q$N(R$_2$)C(O)R$_2$,
—(CH$_2$)$_q$N(R$_2$)C(O)(CH$_2$)$_t$aryl, —(CH$_2$)$_q$ N(R$_2$)SO$_2$(CH$_2$)$_t$aryl, —(CH$_2$)$_q$ N(R$_2$)SO$_2$R$_2$,
—(CH$_2$)$_q$N(R$_2$)C(O)N(R$_2$)(CH$_2$)$_t$aryl,
—(CH$_2$)$_q$N(R$_2$)C(O)N(R$_2$)(R$_2$),
—(CH$_2$)$_q$C(O)N(R$_2$)(R$_2$), —(CH$_2$)$_q$N(R$_2$)C(O)OR$_2$,
—(CH$_2$)$_q$C(O)N(R$_2$)(CH$_2$)$_t$aryl, —(CH$_2$)$_q$C(O)OR$_2$,
—(CH$_2$)$_q$C(O)O(CH$_2$)$_t$aryl, —(CH$_2$)$_q$OC(O)R$_2$,
—(CH$_2$)$_q$OC(O)(CH$_2$)$_t$aryl, —(CH$_2$)$_q$S(O)$_m$R$_2$, and
—(CH$_2$)$_q$S(O)$_m$(CH$_2$)$_t$aryl, where an R$_2$ group may be optionally substituted by hydroxyl, carboxyl, —CONH$_2$, —S(O)$_m$CH$_3$, carboxylate C$_1$-C$_4$ alkyl esters or tetrazole and aryl is phenyl, naphthyl or pyridyl which may be further substituted by 1–2 halogen, 1 to 2 OR$_2$, C(O)OR$_2$, 1 to 3 C$_1$-C$_4$ alkyl, S(O)$_m$R$_2$, or 1H-tetrazole-5-yl;

Y is selected from: hydrogen, C$_1$-C$_8$ alkyl, (CH$_2$)$_t$aryl, —(CH$_2$)$_q$ C$_5$-C$_7$ cycloalkyl, —(CH$_2$)$_q$—K—(C$_1$-C$_6$ alkyl), —(CH$_2$)$_q$—K—(CH$_2$)$_t$aryl, and —(CH$_2$)$_q$—K—(CH$_2$)$_t$ (C$_5$-C$_6$ cycloalkyl), where K is S(O)$_m$ and where the alkyl groups may be optionally substituted by hydroxyl, carboxyl, CONH$_2$, carboxylate C$_1$-C$_4$ alkyl esters or 1H-tetrazole-5-yl and aryl is phenyl, napthyl, pyridyl, thiazolyl, thiopheneyl, pyrazolyl, oxazolyl, isoxazolyl or imidazolyl which may be optionally substituted by 1 to 2 halogen, 1 to 2 OR$_2$, 1 to 2 -N(R$_2$)(R$_2$), CO(OR$_2$), 1 to 2 C$_1$-C$_4$ alkyl, S(O)$_m$R$_2$, or 1H-tetrazol-5-yl, with the proviso that if X is hydrogen, Y is other than hydrogen;

R$_4$ and R$_5$ are independently hydrogen, C$_1$-C$_4$ alkyl, or substituted C$_1$-C$_3$ alkyl where the substituents may be 1 to 2 hydroxyl;

A is

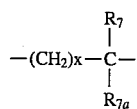

where x is 0, or 1;

$R_7$ and $R_{7a}$ are independently hydrogen, $C_1$–$C_6$ alkyl, phenyl, substituted $C_1$–$C_6$ alky wherein the substitutent is imidixolyl, phenyl, indolyl, p-hydroxyphenyl, $OR_2$, $S(O)_m R_2$, or $R_7$ and $R_{7a}$ may be joined to one another to form a $C_3$ cycloalkyl;

m is 0, 1, or 2;

q is 0, 1, 2, or 3;

t is 0, 1, 2, or 3;

and pharmaceutically acceptable salts and individual diastereomers thereof.

Still more preferred compounds of the instant invention include those of Formula Ic:

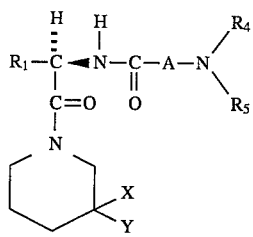

Formula Ic wherein:

$R_1$ is selected from the group consisting of:

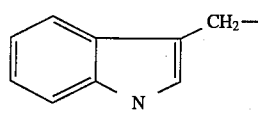

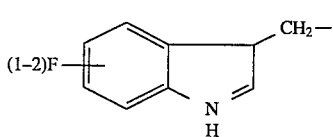

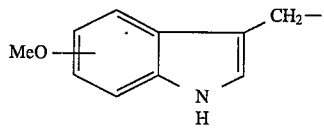

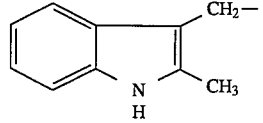

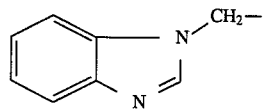

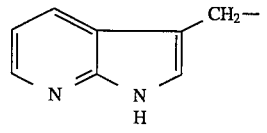

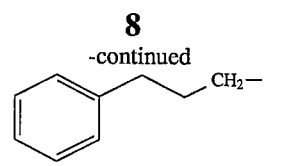

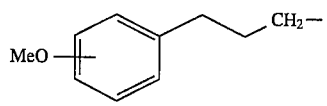

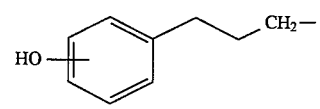

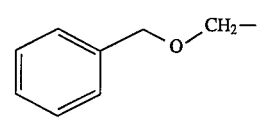

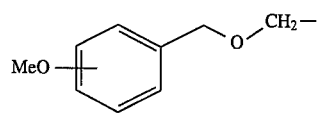

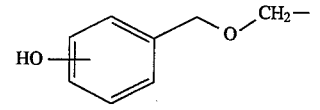

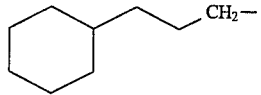

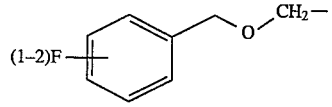

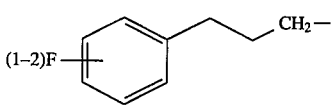

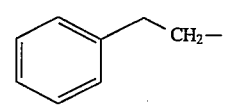

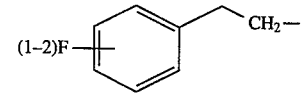

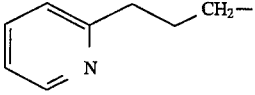

or their regioisomers where not specified;

$R_2$ is hydrogen, $C_1$–$C_6$ alkyl, or $C_3$–$C_7$ cycloalkyl and where two $C_1$–$C_6$ alkyl groups are present on one atom they may be optionally joined to form a $C_5$–$C_7$ cyclic ring optionally including oxygen, sulfur or $NR_{3a}$;

$R_{3a}$ is hydrogen, or $C_1$–$C_4$ alkyl;

X is selected from the group consisting of: hydrogen,

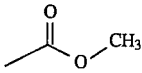 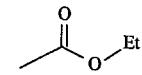 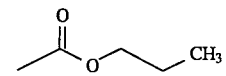

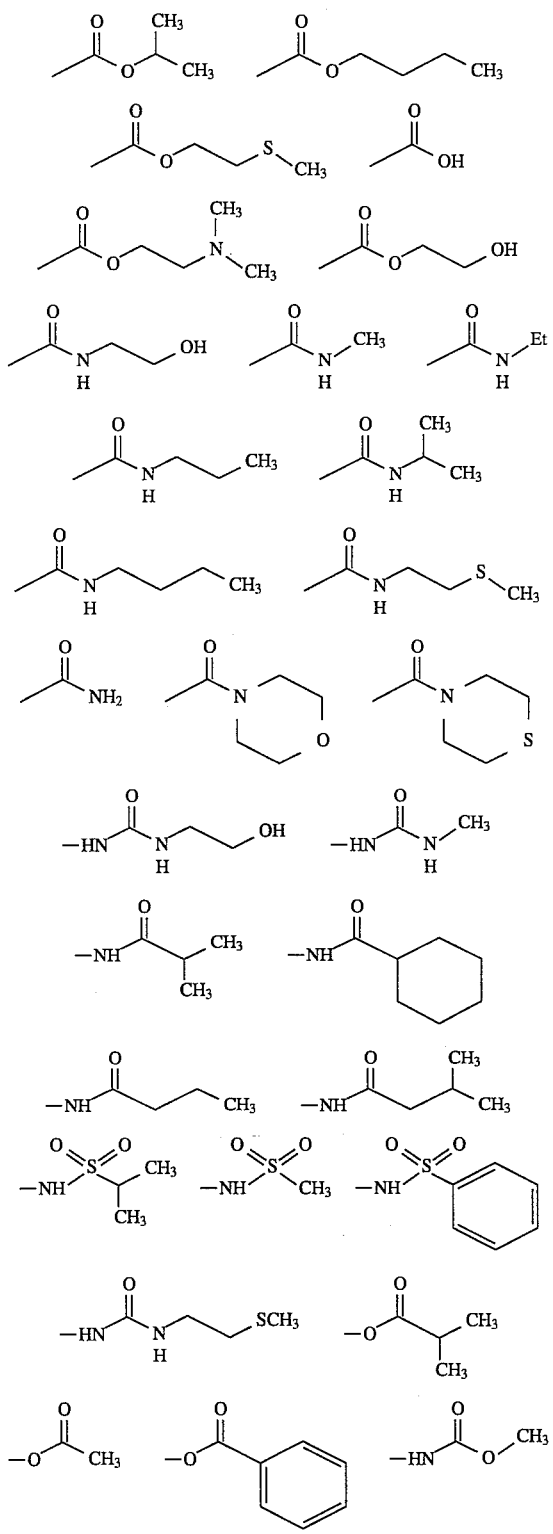
Y is selected from the group consisting of: hydrogen,
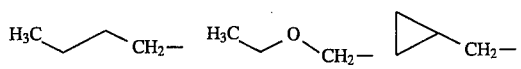
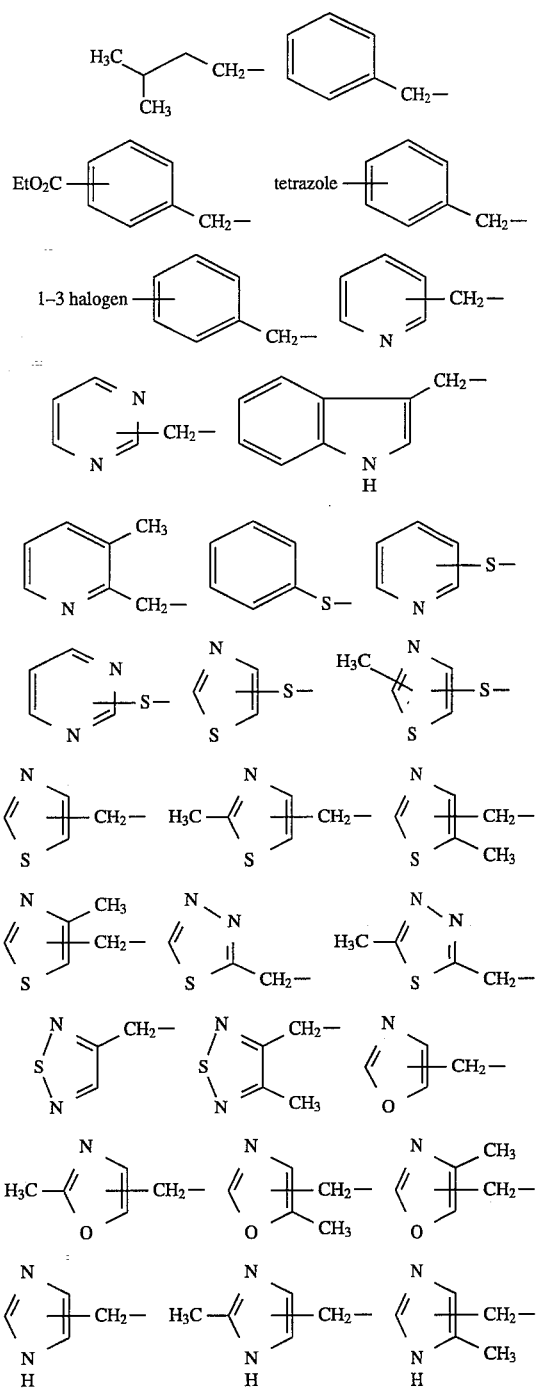
or their regioisomers whereof where not specified, with the proviso that if X is hydrogen, Y is other than hydrogen;
A is selected from the group consisting of:
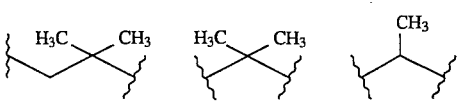

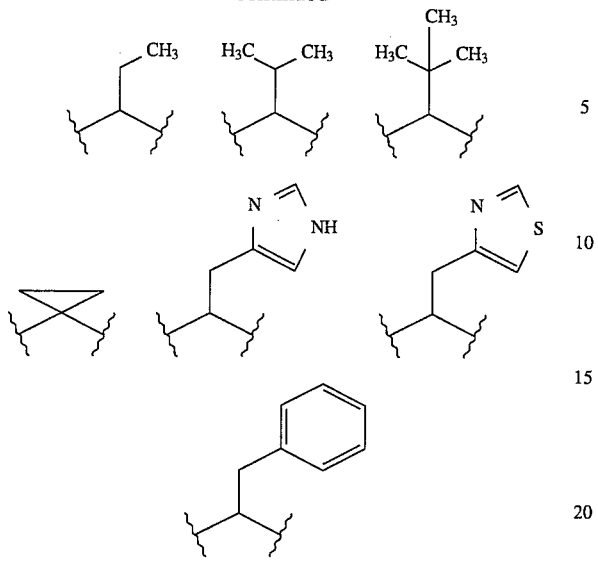
$R_4$ and $R_5$ are independently selected from the group consisting of:
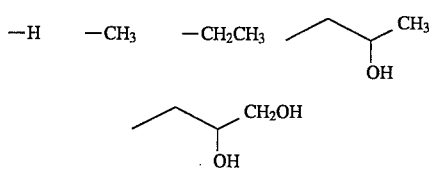
and pharmaceutically acceptable salts and individual diastereomers thereof.
The most preferred compounds of the instant invention include the following:
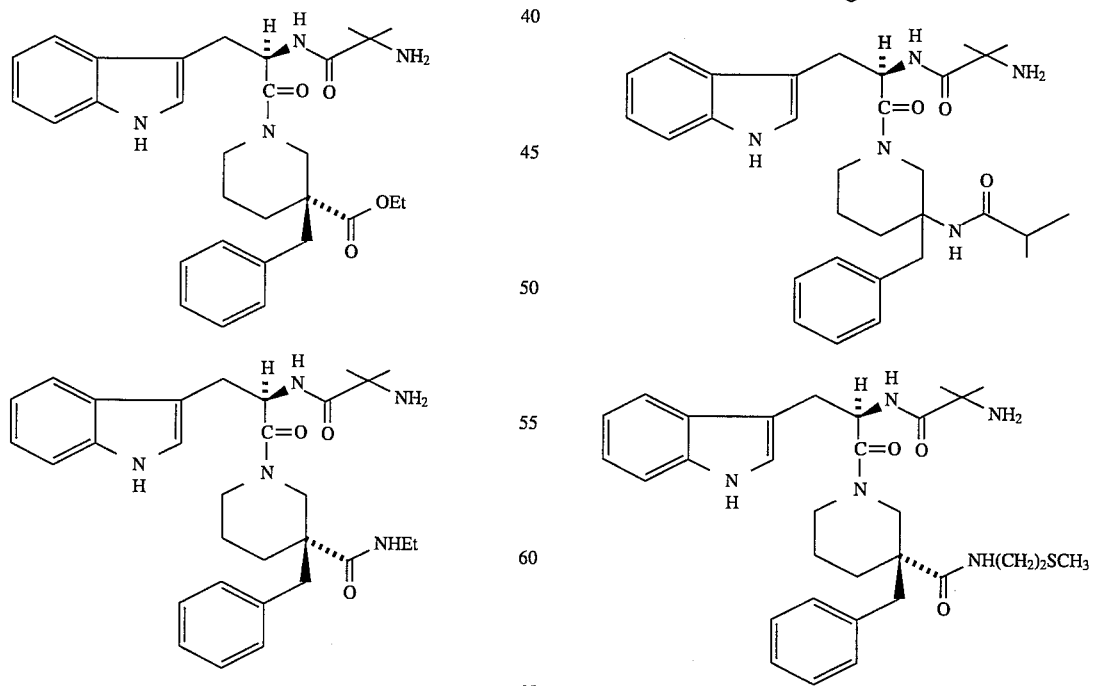

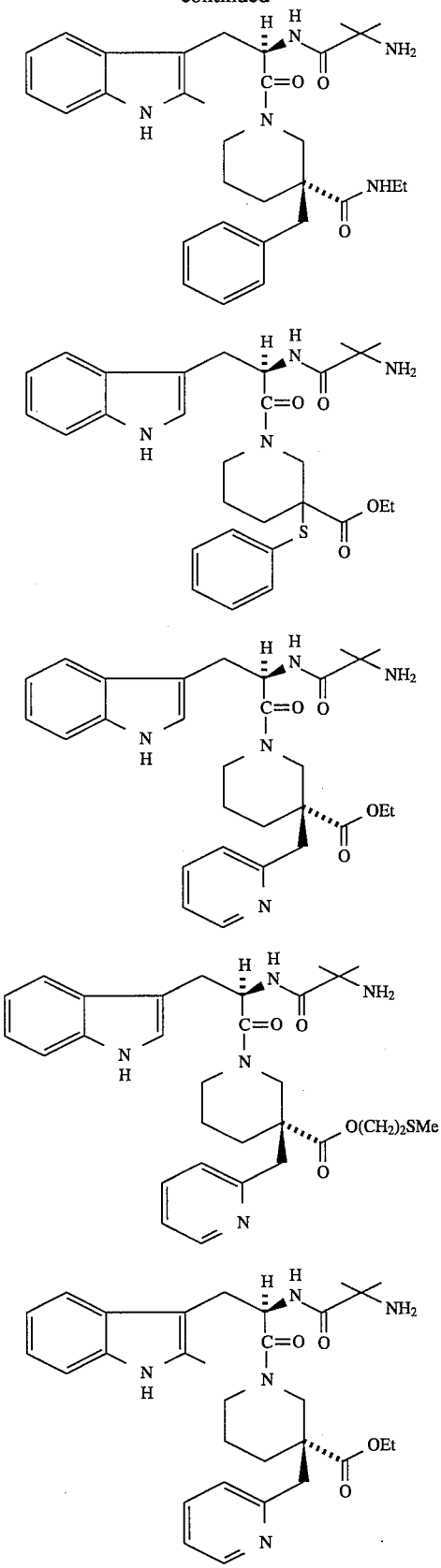
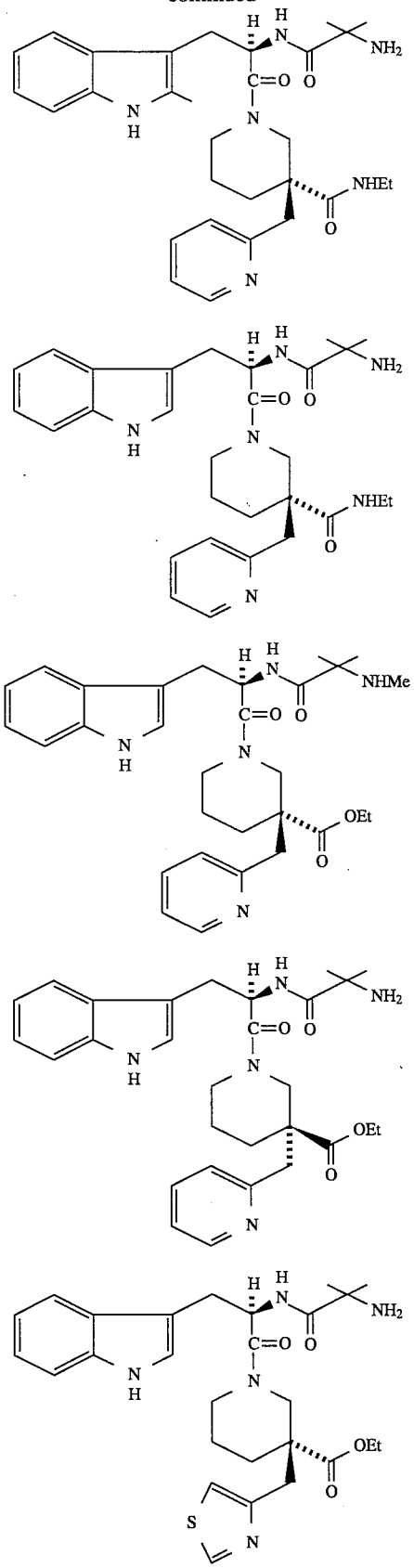

15
-continued
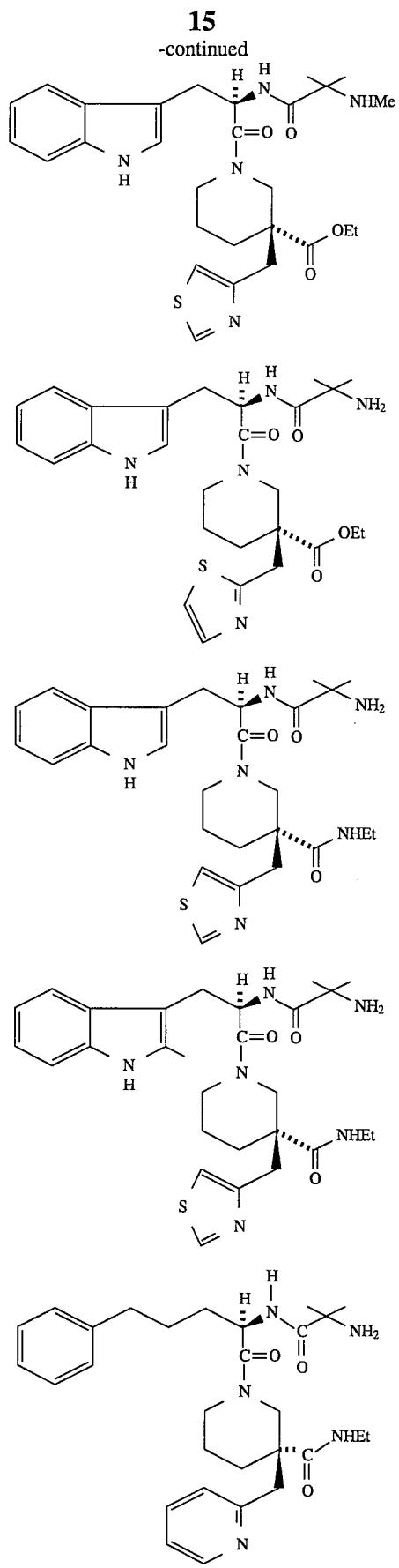
16
-continued
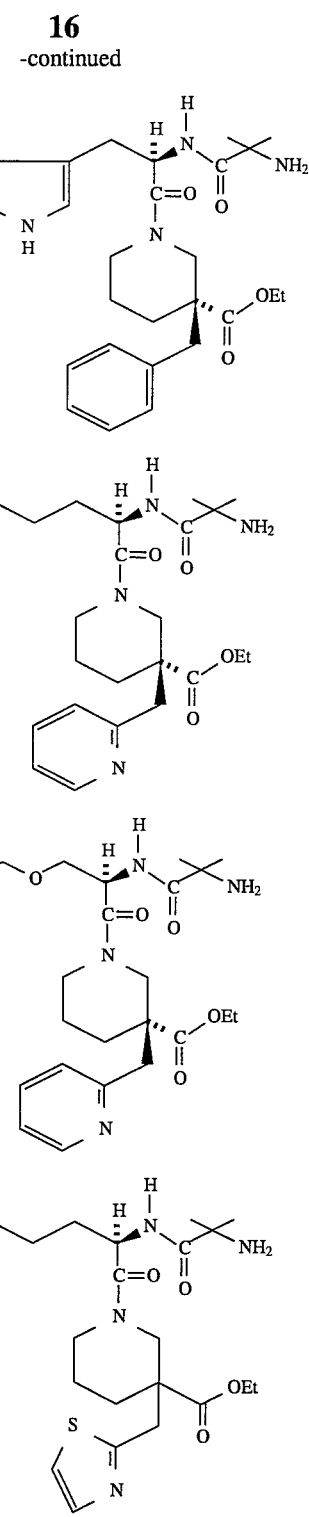

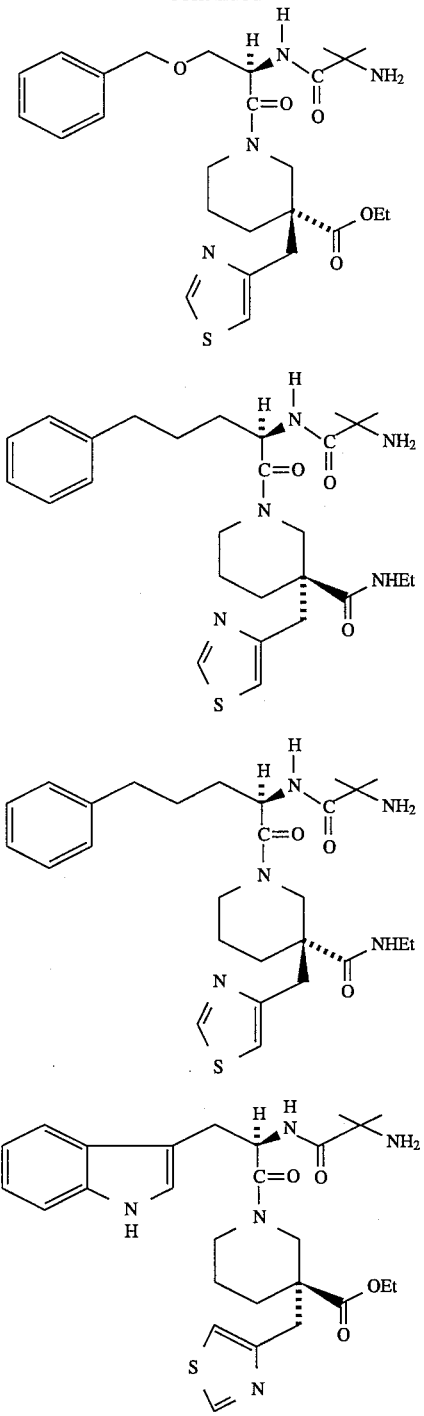
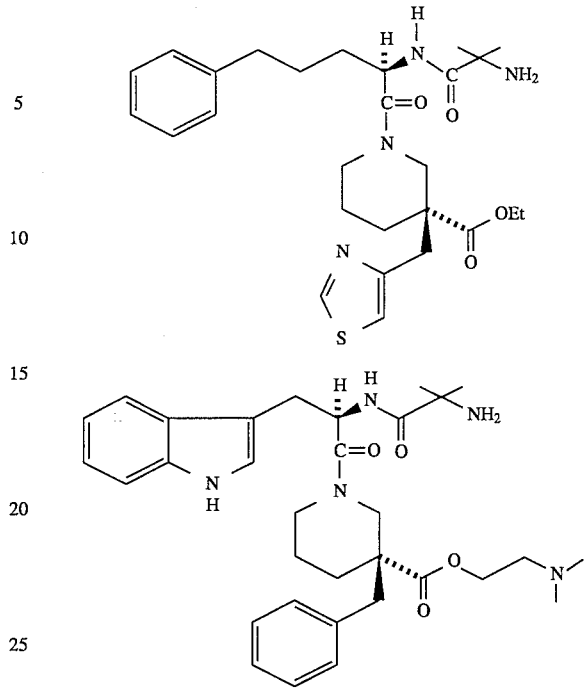

and their pharmaceutically acceptable salts and individual diasteromers thereof where not otherwise specified.

Throughout the instant application, the following abbreviations are used with the following meanings:

| | |
|---|---|
| Bu | butyl |
| Bn | benzyl |
| BOC, Boc | t-butyloxycarbonyl |
| BOP | Benzotriazol-1-yloxy tris(dimethylamino)-phosphonium hexafluorophosphate |
| calc. | calculated |
| CBZ, Cbz | Benzyloxycarbonyl |
| DCC | Dicyclohexylcarbodiimide |
| DMF | N,N-dimethylformamide |
| DMAP | 4-Dimethylaminopyridine |
| EDC | 1-(3-dimethylaminopropyl)-3-ethylcarbodi-imide hydrochloride |
| EI-MS | Electron ion-mass spectroscopy |
| Et | ethyl |
| eq. | equivalent(s) |
| FAB-MS | Fast atom bombardment-mass spectroscopy |
| HOBT, HOBt | Hydroxybenztriazole |
| HPLC | High pressure liquid chromatography |
| KHMDS | Potassium bis(trimethylsilyl)amide |
| LAH | Lithium aluminum hydride |
| LHMDS | Lithium bis(trimethylsilyl)amide |
| Me | methyl |
| MF | Molecular formula |
| MHz | Megahertz |
| MPLC | Medium pressure liquid chromatography |
| NMM | N-Methylmorpholine |
| NMR | Nuclear Magnetic Resonance |
| Ph | phenyl |
| Pr | propyl |
| prep. | prepared |
| TFA | Trifluoroacetic acid |
| THF | Tetrahydrofuran |
| TLC | Thin layer chromatography |
| TMS | Tetramethylsilane |

The compounds of the instant invention all have at least two asymmetric centers when both X and Y are groups other than hydrogen and are different from each other. Additional asymmetric centers may be present depending upon the nature of the various substituents on the molecule. Each such asymmetric center will independently produce two optical isomers and it is intended that all of the possible optical isomers and diastereomers in mixture and as pure or partially purified compounds are included within the ambit of this invention. In the case of the asymmetric carbon atom represented by an asterisk in Formula I, it has been found that compounds are more active as growth hormone secretagogues and, therefore preferred, in which the nitrogen substituent is above and the hydrogen atom is below the plane of the structure as represented in Formula II. An equivalent representation places $R_1$ and the N-substitutent in the plane of the structure with the C=O group above. This configuration corresponds to that present in a D-amino acid. In most cases, this is also designated an R-configuration, although this will vary according to the value of $R_1$ used in making R- or S-stereochemical assignments. In the case of the asymmetric center which bears the X and Y groups, in most cases, both R- and S-configurations are consistent with useful levels of growth hormone secretagogue activity. In addition configurations of many of the most preferred compounds of this invention are indicated. When the carbon atom in Formula I bearing an asterisk is of a defined and usually a D-configuration, two diastereomers result according to the absolute configuration at the carbon atom bearing the X and Y groups. These diastereomers are arbitrarily referred to as diastereomer 1 ($d_1$) and diastereomer 2 ($d_2$) in this invention and, if desired, their independent syntheses or chromatographic separations may be achieved as described herein. Their absolute stereochemistry may be determined by the x-ray crystallography of crystalline products or crystalline intermediates which are derivatized, if necessary, with a reagent containing an asymmetric center of known absolute configuration.

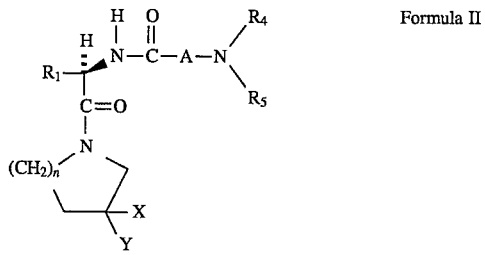

Formula II

The instant compounds are generally isolated in the form of their pharmaceutically acceptable acid addition salts, such as the salts derived from using inorganic and organic acids. Examples of such acids are hydrochloric, nitric, sulfuric, phosphoric, formic, acetic, trifluoroacetic, propionic, maleic, succinic, malonic, methane sulfonic and the like. In addition, certain compounds containing an acidic function such as a carboxy can be isolated in the form of their inorganic salt in which the counterion can be selected from sodium, potassium, lithium, calcium, magnesium and the like, as well as from organic bases.

The preparation of compounds of Formula I of the present invention may be carried out in sequential or convergent synthetic routes. Syntheses detailing the preparation of the compounds of Formula I in a sequential manner are presented in the following reaction schemes.

The phrase "standard peptide coupling reaction conditions" is used repeatedly here, and it means coupling a carboxylic acid with an amine using an acid activating agent such as EDC, DCC, and BOP in a inert solvent such as dichloromethane in the presence of a catalyst such as HOBT. The uses of protective groups for amine and carboxylic acid to facilitate the desired reaction and minimize undesired reactions are well documented. Conditions required to remove protecting groups which may be present and can be found in Greene, T, and Wuts, P. G. M., *Protective Groups in Organic Synthesis*, John Wiley & Sons, Inc., New York, N.Y. 1991. CBZ and BOC were used extensively in the synthesis, and their removal conditions are known to those skilled in the art. For example, removal of CBZ groups can be achieved by a number of methods known in the art; for example, catalytic hydrogenation with hydrogen in the presence of a nobel metal or its oxide such as palladium on activated carbon in a protic solvent such as ethanol. In cases where catalytic hydrogenation is contraindicated by the presence of other potentially reactive functionality, removal of CBZ groups can also be achieved by treatment with a solution of hydrogen bromide in acetic acid, or by treatment with a mixture of TFA and dimethylsulfide. Removal of BOC protecting groups is carried out in a solvent such as methylene chloride or methanol or ethyl acetate, with a strong acid, such as trifluoroacetic acid or hydrochloric acid or hydrogen chloride gas.

The protected amino acid derivatives 1 are, in many cases, commercially available, where the protecting group L is, for example, BOC or CBZ groups. Other protected amino acid derivatives 1 can be prepared by literature methods (Williams, R. M. *Synthesis of Optically Active α-Amino Acids*, Pergamon Press: Oxford, 1989). Many of the piperdines, pyrrolidines, and hexahydro-1H-azepines of Formula 2 are either commercially available or known in the literature and others can be prepared following literature methods described for analogous compounds. Some of these methods are illustrated in the subsequent schemes. The skills required in carrying out the reaction and purification of the resulting reaction products are known to those in the art. Purification procedures includes crystallization, normal phase or reverse phase chromatography.

SCHEME 1

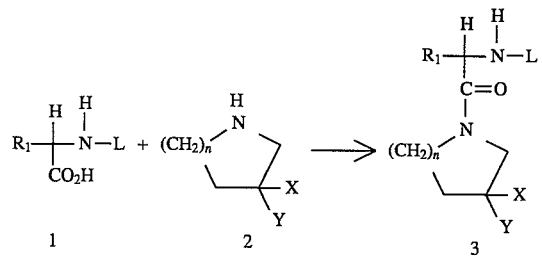

Intermediates of Formula 3 may be synthesized as described in Scheme 1. Coupling of amine of Formula 2, whose preparations are described later if they are not commercially available, to protected amino acids of Formula 1, wherein L is a suitable protecting group, is conveniently carried out under standard peptide coupling conditions.

SCHEME 2

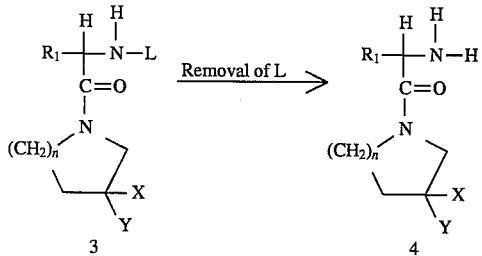

Conversion of 3 to intermediate 4 can be carried out as illustrated in Scheme 2 by removal of the protecting group L (CBZ, BOC, etc.)

SCHEME 3

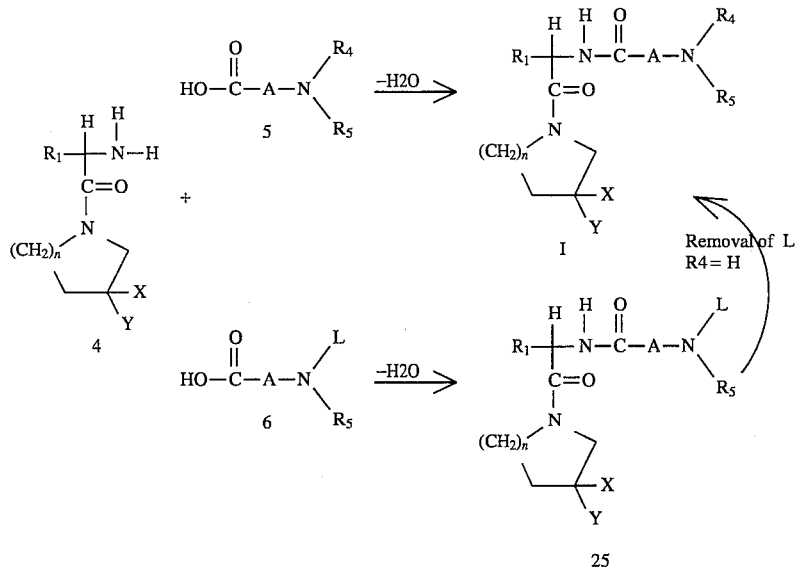

Intermediates of Formula 5, wherein A is —(CH$_2$)$_x$—C(R$_7$)(R$_{7a}$)—(CH$_2$)$_y$— may be prepared as shown in Scheme 3 by coupling intermediates of Formula 4 to amino acids of Formula 5 under the standard peptide coupling reaction conditions. The amino acids 5, as amino acid 1, are either commercially available or can be synthesized by routine methods. Also if R$_4$ or R$_5$ is a hydrogen then the protected amino acids 6 are employed in the coupling reaction, wherein L is a protecting group as defined above. The removal of L in 7 to afford I, where R$_4$=H, can be carried out as noted above.

SCHEME 4

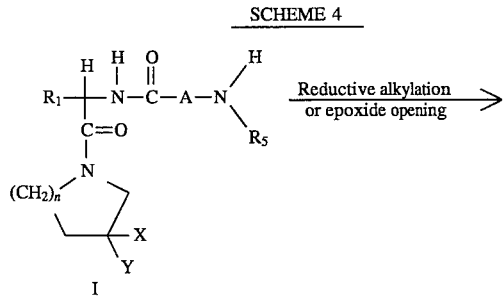

-continued
SCHEME 4

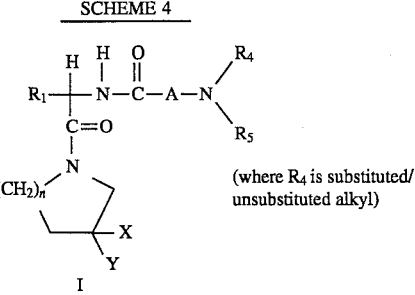

(where R$_4$ is substituted/unsubstituted alkyl)

Compounds of Formula I wherein R$_4$ and/or R$_5$ is a hydrogen may be further elaborated to new Compounds I (with most preferred side chains R$_4$=CH$_2$—CH(OH)—CH$_2$X, wherein X=H or OH) which are substituted on the amino group as depicted in Scheme 4. Reductive alkylation of I with an aldehyde is carried out under conditions known in the art; for example, by catalytic hydrogenation with hydrogen in the presence of platinum, palladium, or nickel catalysts or with chemical reducing agents such as sodium cyanoborohydride in a protic solvent such as methanol or ethanol in the present of catalytic amount of acid. Alternatively, a similar transformation can be accomplished via an epoxide opening reaction.

SCHEME 5

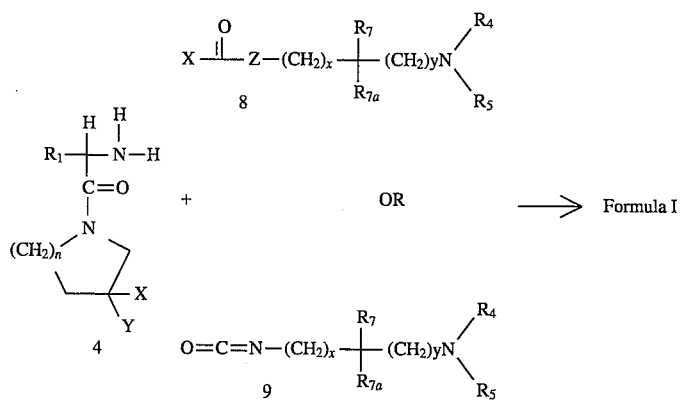

Compounds of Formula I, wherein A is Z—(CH$_2$)$_x$—C(R$_7$)(R$_{7a}$)—(CH$_2$)$_y$ and Z is N—R$_6$ or O may be prepared as shown in Scheme 5 by reacting 4 with reagents 8, wherein X is a good leaving group such as Cl, Br, I, or imidazole. Alternatively, 4 may be reacted with an isocyanate of Formula 9 in an inert solvent such as 1,2-dichloroethane to provide compounds of Formula I where Z is NH.

SCHEME 6

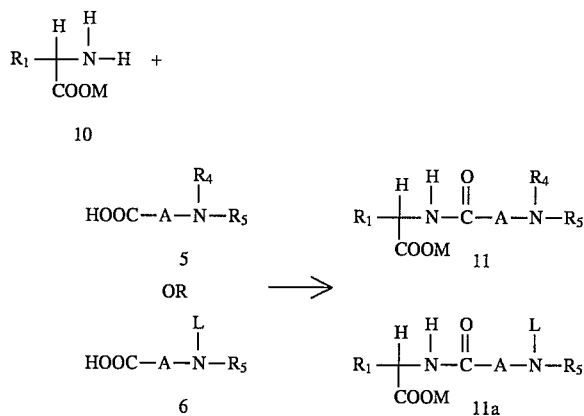

The compounds of general Formula I of the present invention may also be prepared in a convergent manner as described in reaction Schemes 6, 7 and 8.

The carboxylic acid protected amino acid derivatives 10 are, in many cases, commercially available where M=methyl, ethyl, or benzyl esters. Other ester protected amino acids can be prepared by classical methods familiar to those skilled in the art. Some of these methods include the reaction of the amino acid with an alcohol in the presence of an acid such as hydrochloric acid or p-toluenesulfonic acid and azeotropic removal of water. Other reactions includes the reaction of a protected amino acid with a diazoalkane, or with an alcohol and an acid activating agent such as EDC, DCC in the presence of a catalyst such as DMAP and removal of the protecting group L.

Intermediates of Formula 11 or 11a, may be prepared as shown in Scheme 6 by coupling of amino acid ester 10 to amino acids of Formula 6 or 7. When a urea or carbamate linkage is present in 11 or 11a, it can be introduced as illustrated in Scheme 5.

SCHEME 7

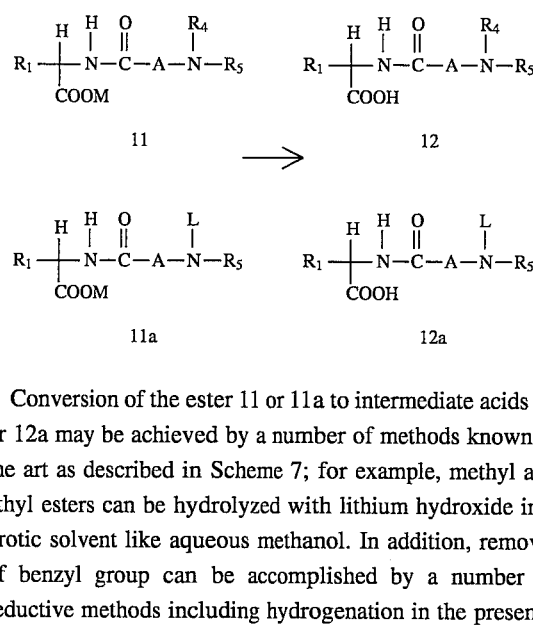

Conversion of the ester 11 or 11a to intermediate acids 12 or 12a may be achieved by a number of methods known in the art as described in Scheme 7; for example, methyl and ethyl esters can be hydrolyzed with lithium hydroxide in a protic solvent like aqueous methanol. In addition, removal of benzyl group can be accomplished by a number of reductive methods including hydrogenation in the presence of palladium catalyst in a protic solvent such as methanol. An allyl ester can be cleaved with tetrakis-triphenylphosphine palladium catalyst in the presence of 2-ethylhexanoic acid in a variety of solvents including ethyl acetate and dichloromethane (see *J. Org. Chem.*, 42, 587 (1982)).

SCHEME 8

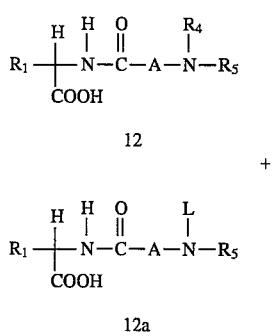

SCHEME 8 -continued

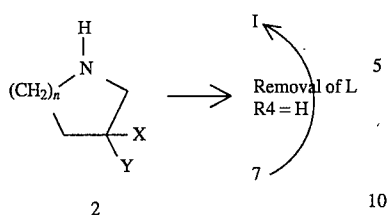

Acid 12 or 12a may then be elaborated to I or to I bearing protecting group L (Compound I) as described in Scheme 8. Coupling of piperidines pyrrolidines or hexahydro-1H-azepines of Formula 2 to acids of Formula 12 or 12a, is conveniently carried out under the standard peptide coupling reaction conditions. Transformation of 7 to I is achieved by removal of the protecting group L. When $R_4$ and/or $R_5$ is H, substituted alkyl groups may be optionally added to the nitrogen atom as described in Scheme 4.

SCHEME 9

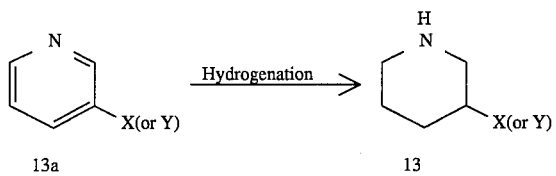

3-Monosubstituted piperidines of formula 13 can be prepared by the reduction of pyridine derivatives or their salts by hydrogenation in a suitable organic solvent such as water, acetic acid, alcohol, e.g. ethanol, or their mixture, in the presence of a noble metal catalyst such as platinum or an oxide thereof on a support such as activated carbon, and conveniently at room temperature and atmospheric pressure or under elevated temperature and pressure. 3-Monosubstituted piperidines can also be prepared by modification of the X or Y moiety of the existing 3-monosubstituted piperidines.

SCHEME 9A

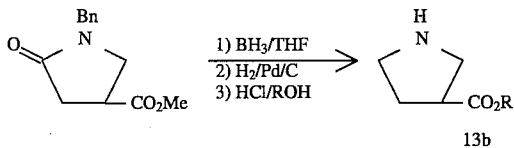

3-Monosubstituted pyrrolidines are commercially available or can be conveniently prepared by literature procedures. Shown in Scheme 9A is an example of the preparation of these compounds via pyrrolidine-3-carboxylic acid ester. The commercially available compound methyl 1-benzyl-4-oxo-3-pyrrolidinecarboxylate is reduced by borane (*J. Chem. Soc.*, 24, 1618–1619). Removal of the benzyl group by catalytic hydrogenolysis followed by ester exchange in an appropriate alcohol medium such as ethyl alcohol in the presence of acid gave the compound 13b. The ester functionality may be further modified through conventional chemistry to other groups as defined by X. 3-Monosubstituted pyrrolidines may also be prepared by catalytic hydrogenation of 3-substituted pyrroles.

SCHEME 9B

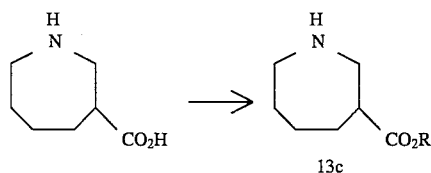

Hexahydro-1H-azepines are commercially available or may be prepared by the literature procedure. Hexahydro-1H-azepine-3-carboxylic acid (*Krogsgaard-Larsen, P. et al., Acta. Chem. Scand., B32*, 327,(1978)) is esterified in an alcohol solvent in the presence of acid The ester functionality may be further modified through conventional chemistry to other groups within the definition of X.

SCHEME 10

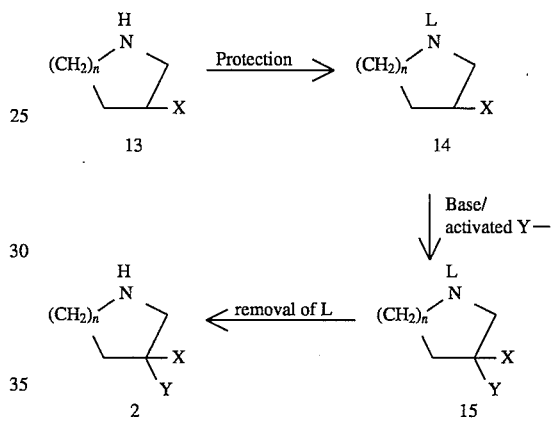

Illustrated in Scheme 10 is a general way to prepare di-substituted piperidines, pyrrolidines, and hexahydro-1H-azepines. Compounds of Formula 13 wherein X is an electron withdrawing group such as —CN, —$CO_2R_8$, where $R_8$ is alkyl, aryl, and ($C_1$–$C_4$alkyl)aryl are known compounds or may be prepared by methods analogous to those used for the preparation of such known compounds. The secondary amine of compounds of Formula 13 may be first protected by a protecting group L such as BOC and CBZ using the conventional techniques. Introduction of the Y substitution can be achieved by first reacting compounds of Formula 14 with a strong base such as lithium bis(trimethylsilyl)amide, lithium diisopropylamide following by addition of alkylating or acylating reagents such as alkyl halides, aryl alkyl halides, acyl halides, and haloformates in a inert solvent such as THF at temperatures from −100° to room temperature. Thio derivatives where the sulfur is attached directly to an alkyl or an aryl group can be prepared similarly by reacting with a disulfide. The halides used in these reactions are either commercially available or known compounds in the literature or may be prepared by methods analogous to those used for the preparation of known compounds. The protecting group L in compounds of formula 15 may be removed with conventional chemistry to give compounds of Formula 2.

SCHEME 11

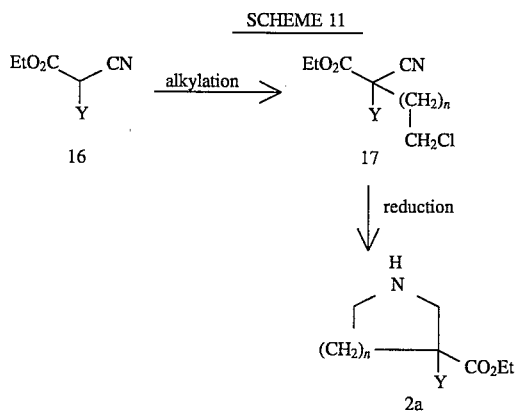

Alternative ways of preparing compounds of Formula 2 include construction of the ring itself (Jacoby, R. L. et al, *J. Med. Chem.*, 17, 453–455, (1974)). Alkylation of the cyanoacetates of general formula 16, which are commercially available or may be prepared from literature procedures, with alkyl dihalides such as 1-bromo-2-chloroethane or 1-bromo-3-chloropropane yields the chloride 17. Reduction of the nitriles 17 by borane or by hydrogenation using Raney Ni as a catalyst gives the corresponding primary amines, which upon refluxing in ethanol to give compounds of Formula 2a.

SCHEME 12

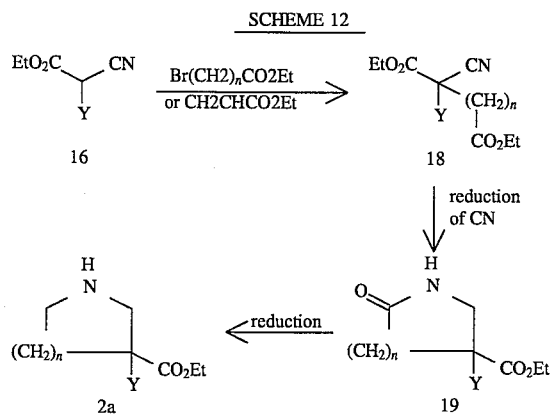

Alternatively, the cyanoacetates of general formula 16 may be alkylated with an ethoxycarbonylalkyl bromide or reacted with ethyl acrylate to give compounds of Formula 18. Reduction of the nitriles 18 by borane or by hydrogenation using Raney Ni as a catalyst gives the corresponding primary amines, which upon refluxing in ethanol gives lactam 19. Reduction of the lactam 19 by borane gives compounds of Formula 2a.

SCHEME 13

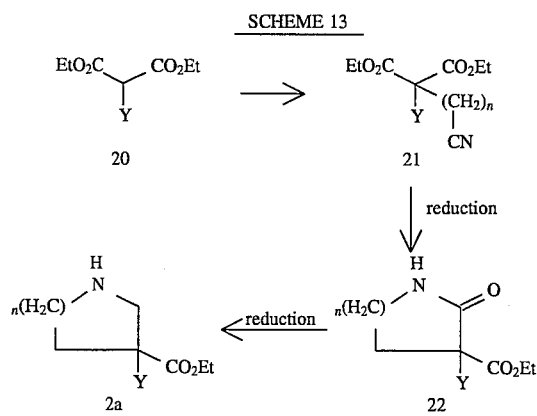

Alternatively, a malonate of general formula 20 may be alkylated with cyanoalkyl bromide or can be reacted with acrylonitrile to form compounds of formula 21. Reduction of the nitriles 21 by borane or by hydrogenation using Raney Ni as a catalyst gives the corresponding primary amines, which upon refluxing in ethanol gives lactam 22. Reduction of the lactam 22 by borane gives compounds of formula 2a.

SCHEME 14

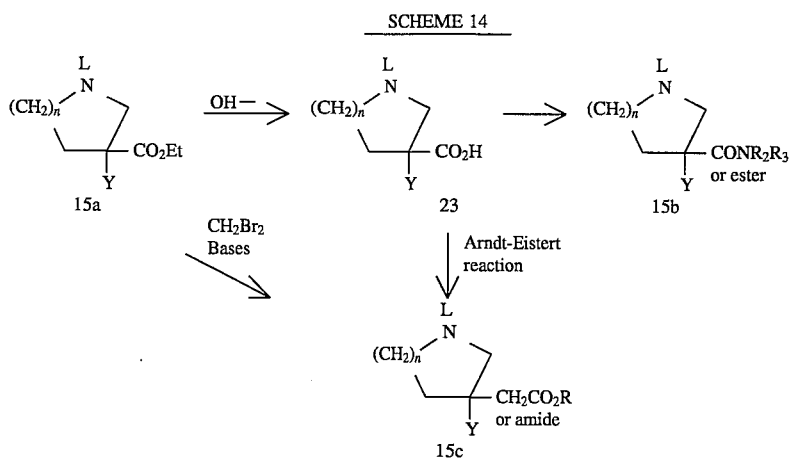

The X, Y functionalities in compounds of general structure 15 may be further elaborated to groups not accessible by direct alkylation. For example in Compound 15 when X=CO$_2$Et the ester (provided that this is the only ester group in the molecule) can be saponified to the carboxylic acid, which can be further derivatized to amides or other esters. The carboxylic acid can be converted into its next higher homologue, or to a derivative of the homologous acid, such as amide or ester by an Arndt-Eistert reaction. Alternatively, the ester can be directly homologated by the protocol using ynolate anions described by C. J. Kowalski and R. E. Reddy in *J. Org. Chem.*, 57, 7194–7208 (1992). The resulting acid and/or ester may be converted to the next higher homologue, and so on and so forth. The protecting group L may be removed through conventional chemistry.

may also be converted to a good leaving group such as mesylate and displaced by a nucleophile such as cyanide, a thiol or an azide. Reduction of the azide in compounds of Formula 20 to an amine 21 can be achieved by hydrogenation in the presence of a noble metal such as palladium or its oxide or Raney nickel in a protic solvent such as ethanol. The nitrile can be reduced to afford the homologous amine. The amine of Formula 21 may be further elaborated to amides, ureas sulfonamides as defined by X through conventional chemistry. The protecting group L may be removed through conventional chemistry.

SCHEME 15

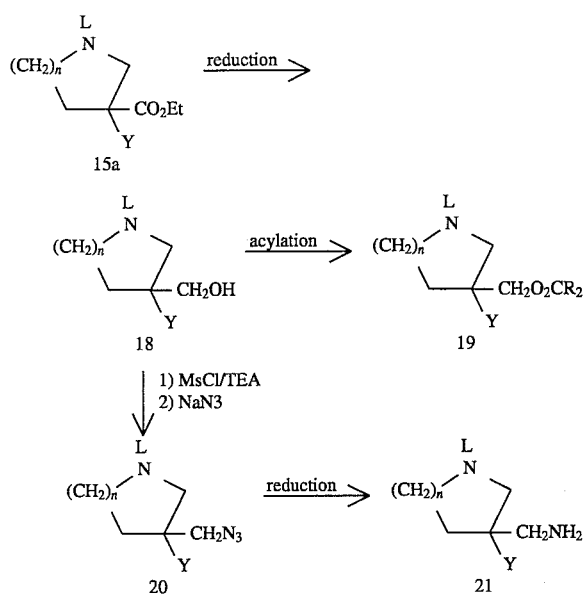

SCHEME 16

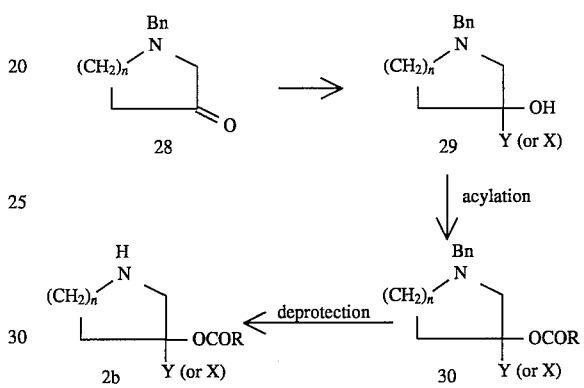

The ester in 15a may be reduced to an alcohol 18 in a suitable solvent such as THF or ether with a reducing agent such as DIBAL-H and conveniently carried out at temperatures from −100° C. to 0° C. The alcohol may be acylated to Compound 19 in a suitable solvent such as dichloromethane using an acyl halide or acid anhydride in the presence of a base such as triethyl amine (TEA). The hydroxy group in 18

In cases where oxygen is directly attached to the ring, a convenient method involves the addition reaction by an activated form of an alkyl, aryl, alkylaryl group, such as lithium reagent, Grignard reagents, and the like with a ketone of general formula 28, which is commercially available. Further derivatization of the resulting hydroxy group by acylation, sulfonylation, alkylation, and the like gives compounds as defined by Y or X through conventional chemistry. Removal of the benzyl protective group may be carried out under the usual conditions to give compounds of general formula 2b. Shown in Scheme 16 is a general example of acylations.

SCHEME 17

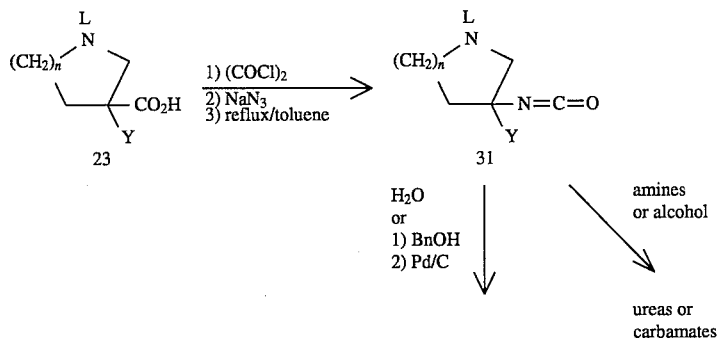

-continued
SCHEME 17

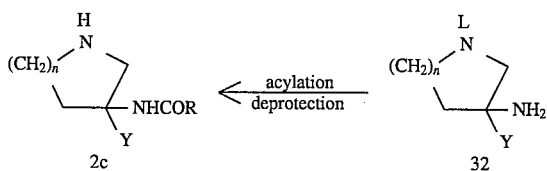

In cases where a nitrogen-substituted group is directly attached to the ring, a convenient method is to use the Curtius rearrangement on the acid 23 to afford the isocyanate 31. Addition of amines or alcohols give ureas or carbamates respectively which can be deprotected to remove L to give special cases of compounds of formula 2. Conversion of the isocyanate to amine by hydrolysis gives compound 32. Further derivatization of the resulting amine group by acylation, sulfonylation, alkylation, and the like to give compounds as defined by Y or X can be done through conventional chemistry. Removal of the protective group L may be carried out under the usual conditions to give compounds of general formula 2c. Shown in Scheme 17 is a general example of acylations.

example of a procedure that uses nitrile as a starting point for the preparation of compounds with different substitutions. Removal of the protective group L gives compounds of general formula 2 as described in Scheme 10.

Compounds of the general formula 2 prepared in this way are racemic when X and Y are not identical. Resolution of the two enatiomers can be conveniently achieved by classical crystallization methods by using a chiral acid such as L- or D-tartaric acid, (+) or (−)-10-camphorsulfonic acid in a suitable solvent such as acetone, water, alcohol, ether, acetate or their mixture. Alternatively, the racemic amine 2 can be reacted with a chiral auxiliary such as (R) or (S)—O-acetylmandelic acid followed by chromatographic separation of the two diastereomers, and removal of the

SCHEME 18

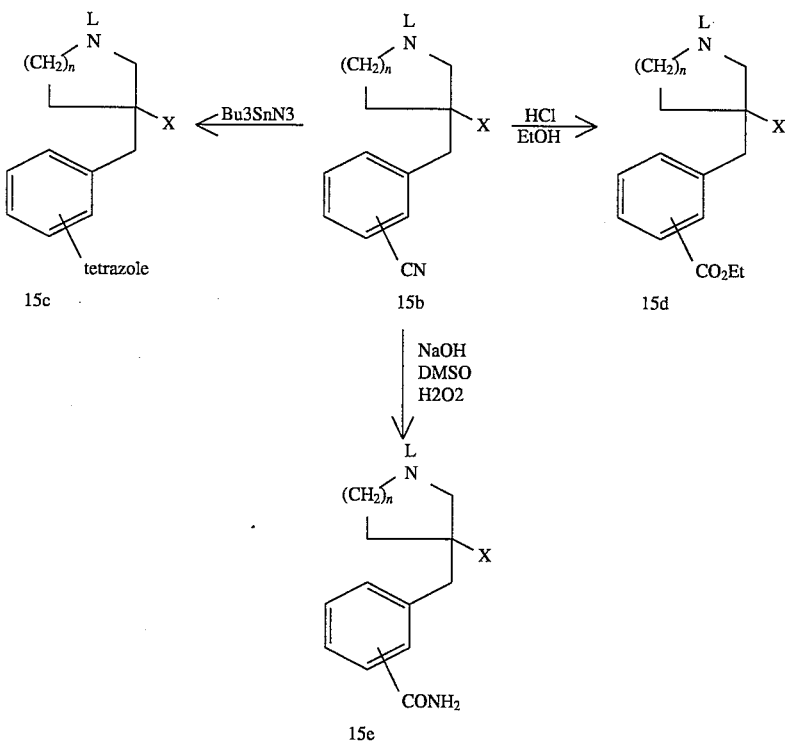

For compounds that are not readily obtainable by direct alkylation as shown in Scheme 10, modifications of easily obtainable compounds of general formula 15 may be conducted to achieve the desired substitution through conventional chemistry. For example, compounds with Y being hydroxybenzyl may be prepared by demethylation of the corresponding compound wherein Y is methoxybenzyl. Similarly, compounds with Y being aminobenzyl may be prepared by reduction of the corresponding compound wherein Y is nitrobenzyl. Shown in Scheme 18 is an chiral auxiliary by hydrolysis. Alternatively asymmetric alkylation can also be utilized for the synthesis of optically active intermediate by introducing a removable chiral auxiliary in X or in place of L with subsequent chromatographic separation of diastereomers.

In cases where a sulfide is present in the molecule, it may be oxidized to a sulfoxide or to a sulfone with oxidizing agents such as sodium periodate, m-chloroperbenzoic acid or Oxone® in an solvent such as dichloromethane, alcohol or water or their mixtures.

The compounds of the present invention may also be prepared from a variety of substituted natural and unnatural amino acids of formulas 46. The preparation of many of these acids is described in U.S. Pat. No. 5,206,237. The preparation of these intermediates in racemic form is accomplished by classical methods familiar to those skilled in the art (Williams, R. M. "*Synthesis of Optically Active α-Amino Acids*" Pergamon Press: Oxford, 1989; Vol. 7). Several methods exist to resolve (DL)-

amino acids. One of the common methods is to resolve amino or carboxyl protected intermediates by crystallization of salts derived from optically active acids or amines. Alternatively, the amino group of carboxyl protected intermediates may be coupled to optically active acids by using chemistry described earlier. Separation of the individual diastereomers either by chromatographic techniques or by crystallization followed by hydrolysis of the chiral amide furnishes resolved amino acids. Similarly, amino protected intermediates may be converted to a mixture of chiral diastereomeric esters and amides. Separation of the mixture using methods described above and hydrolysis of the individual diastereomers provides (D) and (L) amino acids. Finally, an enzymatic method to resolve N-acetyl derivatives of (DL)-amino acids has been reported by Whitesides and coworkers in *J. Am. Chem. Soc.* 1989, 111, 6354–6364.

When it is desirable to synthesize these intermediates in optically pure form, established methods include: (1) asymmetric electrophilic amination of chiral enolates (*J. Am. Chem. Soc.* 1986, 108, 6394–6395, 6395–6397, and 6397–6399), (2) asymmetric nucleophilic amination of optically active carbonyl derivatives, (*J. Am. Chem. Soc.* 1992, 114, 1906; *Tetrahedron Lett.* 1987, 28, 32), (3) diastereoselective alkylation of chiral glycine enolate synthons (*J. Am. Chem. Soc.* 1991, 113, 9276; *J. Org. Chem.* 1989, 54, 3916), (4) diastereoselective nucleophilic addition to a chiral electrophilic glycinate synthon (*J. Am. Chem. Soc.* 1986, 108, 1103), (5) asymmetric hydrogenation of prochiral dehydroamino acid derivatives ("*Asymmetric Synthesis, Chiral Catalysis*; Morrison, J. D., Ed; Academic Press: Orlando, Fla., 1985; Vol 5), and (6) enzymatic syntheses (*Angew. Chem. Int. Ed. Engl.* 1978, 17, 176).

SCHEME 19

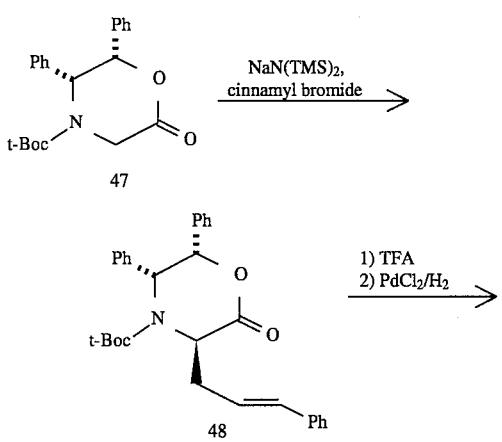

-continued
SCHEME 19

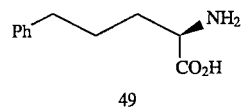

For example, alkylation of the enolate of diphenyloxazinone 47 (*J. Am. Chem. Soc.* 1991, 113, 9276) with cinnamyl bromide in the presence of sodium bis(trimethylsilyl)amide proceeds smoothly to afford 48 which is converted into the desired (D)-2-amino-5-phenylpentanoic acid 49 by removing the N-t-butyloxycarbonyl group with trifluoroacetic acid and hydrogenation over a PdCl$_2$ catalyst (Scheme 19).

SCHEME 20

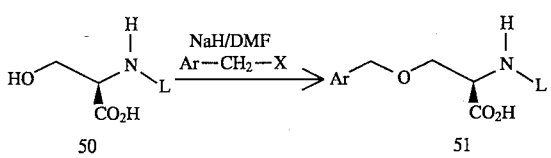

Intermediates of formula 46 which are O-benzyl-(D)-serine derivatives 51 are conveniently prepared from suitably substituted benzyl halides and N-protected-(D)-serine 50. The protecting group L is conveniently a BOC or a CBZ group. Benzylation of 64 can be achieved by a number of methods well known in the literature including deprotonation with two equivalents of sodium hydride in an inert solvent such as DMF followed by treatment with one equivalent of a variety of benzyl halides (*Synthesis* 1989, 36) as shown in Scheme 20.

The O-alkyl-(D)-serine derivatives may also be prepared using an alkylation protocol. Other methods that could be utilized to prepare (D)-serine derivatives of formula 51 include the acid catalyzed benzylation of carboxyl protected intermediates derived from 50 with reagents of formula ArCH$_2$OC(=NH)CCl$_3$ (O. Yonemitsu et al., *Chem. Pharm. Bull.* 1988, 36, 4244). Alternatively, alkylation of the chiral gylcine enolates (*J. Am. Chem. Soc.* 1991, 113, 9276; *J. Org. Chem.* 1989, 54, 3916) with ArCH$_2$OCH$_2$X where X is a leaving group affords 51. In addition D,L-O-aryl(alkyl)serines may be prepared and resolved by methods described above.

It is noted that in some cases the order of carrying out the foregoing reaction schemes may be varied to facilitate the reaction or to avoid unwanted reaction products.

The utility of the compounds of the present invention as growth hormone secretagogues may be demonstrated by methodology known in the art, such as an assay disclosed by Smith, et al., *Science*, 260, 1640–1643 (1993) (see text of FIG. 2 therein). In particular, all of the compounds prepared in the following examples had activity as growth hormone secretagogues in the aforementioned assay. Such a result is indicative of the intrinsic activity of the present compounds as growth hormone secretagogues.

The growth hormone releasing compounds of Formula I are useful in vitro as unique tools for understanding how growth hormone secretion is regulated at the pituitary level. This includes use in the evaluation of many factors thought or known to influence growth hormone secretion such as age, sex, nutritional factors, glucose, amino acids, fatty acids, as well as fasting and non-fasting states. In addition, the compounds of this invention can be used in the evaluation of how other hormones modify growth hormone releasing activity. For example, it has already been established that somatostatin inhibits growth hormone release. Other hormones that are important and in need of study as to their effect on growth hormone release include the gonadal hormones, e.g., testosterone, estradiol, and progesterone; the adrenal hormones, e.g., cortisol and other corticoids, epinephrine and norepinephrine; the pancreatic and gastrointestinal hormones, e.g., insulin, glucagon, gastrin, secretin; the vasoactive peptides, e.g., bombesin, the neurokinins; and the thyroid hormones, e.g., thyroxine and triiodothyronine. The compounds of Formula I can also be employed to investigate the possible negative or positive feedback effects of some of the pituitary hormones, e.g., growth hormone and endorphin peptides, on the pituitary to modify growth hormone release. Of particular scientific importance is the use of these compounds to elucidate the subcellular mechanisms mediating the release of growth hormone.

The compounds of Formula I can be administered to animals, including man, to release growth hormone in vivo. For example, the compounds can be administered to commercially important animals such as swine, cattle, sheep and the like to accelerate and increase their rate and extent of growth, to improve feed efficiency and to increase milk production in such animals. In addition, these compounds can be administered to humans in vivo as a diagnostic tool to directly determine whether the pituitary is capable of releasing growth hormone. For example, the compounds of Formula I can be administered in vivo to children. Serum samples taken before and after such administration can be assayed for growth hormone. Comparison of the amounts of growth hormone in each of these samples would be a means for directly determining the ability of the patient's pituitary to release growth hormone.

Accordingly, the present invention includes within its scope pharmaceutical compositions comprising, as an active ingredient, at least one of the compounds of Formula I in association with a pharmaceutical carrier or diluent. Optionally, the active ingredient of the pharmaceutical compositions can comprise an anabolic agent in addition to at least one of the compounds of Formula I or another composition which exhibits a different activity, e.g., an antibiotic growth permittant or an agent to treat osteoporosis or in combination with a corticosteroid to minimize the latter's catabolic side effects or with other pharmaceutically active materials wherein the combination enhances efficacy and minimizes side effects.

Growth promoting and anabolic agents include, but are not limited to, TRH, diethylstilbesterol, conjugated estrogens, β-agonists, theophylline, anabolic steroids, enkephalins, E series prostaglandins, compounds disclosed in U.S. Pat. No. 3,239,345, e.g., zeranol, and compounds disclosed in U.S. Pat. No. 4,036,979, e.g., sulbenox or peptides disclosed in U.S. Pat. No. 4,411,890.

A still further use of the growth hormone secretagogues of this invention is in combination with other growth hormone secretagogues such as the growth hormone releasing peptides GHRP-6, GHRP-1 (as described in U.S. Pat. Nos. 4,411,890 and publications WO 89/07110, WO 89/07111) and B-HT920 as well as hexarelin and GHRP-2 (as described in WO 93/04081) or growth hormone releasing hormone (GHRH, also designated GRF) and its analogs or growth hormone and its analogs or somatomedins including IGF-1 and IGF-2 or α- adrenergic agonists such as clonidine or serotonin 5HTID agonists such as sumatriptan or agents which inhibit somatostatin or its release such as physostigmine and pyridostigmine.

As is well known to those skilled in the art, the known and potential uses of growth hormone are varied and multitudinous. Thus, the administration of the compounds of this invention for purposes of stimulating the release of endogenous growth hormone can have the same effects or uses as growth hormone itself. These varied uses of growth hormone may be summarized as follows: stimulating growth hormone release in elderly humans; treating growth hormone deficient adults; prevention of catabolic side effects of glucocorticoids; treatment of osteoporosis; stimulation of the immune system, acceleration of wound healing; accelerating bone fracture repair; treatment of growth retardation; treating acute or chronic renal failure or insufficiency; treatment of physiological short stature, including growth hormone deficient children; treating short stature associated with chronic illness; treatment of obesity and growth retardation associated with obesity; treating growth retardation associated with Prader-Willi syndrome and Turner'syndrome; accelerating the recovery and reducing hospitalization of burn patients or following major surgery such as gastrointestinal surgery; treatment of intrauterine growth retardation, and skeletal dysplasia; treatment of peripheral neuropathies; replacement of growth hormone in stressed patients; treatment of osteochondrodysplasias, Noonans syndrome, schizophrenia, depression, Alzheimer's disease, delayed wound healing, and psychosocial deprivation; treatment of pulmonary dysfunction and ventilator dependency; attenuation of protein catabolic response after a major operation; treating malabsorption syndromes; reducing cachexia and protein loss due to chronic illness such as cancer or AIDS; accelerating weight gain and protein accretion in patients on TPN (total parenteral nutrition); treatment of hyperinsulinemia including nesidioblastosis; adjuvant treatment for ovulation induction and to prevent and treat gastric and duodenal ulcers; to stimulate thymic development and prevent the age-related decline of thymic function; adjunctive therapy for patients on chronic hemodialysis; treatment of immunosuppressed patients and to enhance antibody response following vaccination; increasing the total lymphocyte count of a human, in particular, increasing the T4/T8-cell ratio in human with a depressed T4/T8-cell ratio resulting, for example, from physical trauma, such as closed head injury, or from infection, such as bacterial or viral infection, especially infection with the human immunodeficiency virus; improvement in muscle strength, mobility, maintenance of skin thickness, metabolic homeostasis, renal hemeostasis in the frail elderly; stimulation of osteoblasts, bone remodelling, and cartilage growth; stimulation of the immune system in companion animals and treatment of disorders of aging in companion animals; growth promotant in livestock; and stimulation of wool growth in sheep. Further, the instant compounds are useful for increasing feed efficiency, promoting growth, increasing milk production and improving the carcass quality of livestock.

In particular, the instant compounds are useful in the prevention or treatment of a condition selected from the group consisting of: osteoporosis; catabolic illness; immune deficiency, including that in individuals with a depressed T4/T8 cell ratio; hip fracture; musculoskeletal impairment in the elderly; growth hormone deficiency in adults or in children; obesity; cachexia and protein loss due to chronic illness such as AIDS or cancer; and treating patients recovering from major surgery, wounds or burns, in a patient in need thereof.

It will be known to those skilled on the art that there are numerous compounds now being used in an effort to treat the diseases or therapeutic indications enumerated above. Combinations of these therapeutic agents some of which have also been mentioned above with the growth hormone secretagogues of this invention will bring additional, complementary, and often synergistic properties to enhance the growth promotant, anabolic and desirable properties of these various therapeutic agents. In these combinations, the therapeutic agents and the growth hormone secretagogues of this invention may be independently present in dose ranges from one one-hundredth to one times the dose levels which are effective when these compounds and secretagogues are used singly.

Combined therapy to inhibit bone resorption, prevent osteoporosis and enhance the healing of bone fractures can be illustrated by combinations of bisphosphonates and the growth hormone secretagogues of this invention. The use of bisphosphonates for these utilities has been reviewed, for example, by Hamdy, N.A.T. Role of Bisphosphonates in Metabolic Bone Diseases. *Trends in Endocrinol. Metab.,*, 4, 19–25 (1993). Bisphosphonates with these utilities include alendronate, tiludronate, dimethyl-APD, risedronate, etidronate, YM-175, clodronate, pamidronate, and BM-210995. According to their potency, oral daily dosage levels of the bisphosphonate of between 0.1 mg and 5 g and daily dosage levels of the growth hormone secretagogues of this invention of between 0.01 mg/kg to 20 mg/kg of body weight are administered to patients to obtain effective treatment of osteoporosis.

In the case of alendronate daily oral dosage levels of 0.1 mg to 50 mg are combined for effective osteoporosis therapy with 0.01 mg/kg to 20 mg/kg of the growth hormone secretagogues of this invention.

Osteoporosis and other bone disorders may also be treated with compounds of this invention in combination with calcitonin, estrogens, raloxifene and calcium supplements such as calcium citrate.

Anabolic effects especially in the treatment of geriatric male patients are obtained with compounds of this invention in combination with anabolic steroids such as oxymetholone, methyltesterone, fluoxymesterone and stanozolol.

The compounds of this invention can be administered by oral, parenteral (e.g., intramuscular, intraperitoneal, intravenous or subcutaneous injection, or implant), nasal, vaginal, rectal, sublingual, or topical routes of administration and can be formulated in dosage forms appropriate for each route of administration.

Solid dosage forms for oral administration include capsules, tablets, pills, powders and granules. In such solid dosage forms, the active compound is admixed with at least one inert pharmaceutically acceptable carrier such as sucrose, lactose, or starch. Such dosage forms can also comprise, as in normal practice, additional substances other than inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include pharmaceutically acceptable emulsions, solutions, suspensions, syrups, and elixirs containing inert diluents commonly used in the art, such as water. Besides such inert diluents, compositions can also include adjuvants, such as wetting agents, emulsifying and suspending agents, and sweetening, flavoring, and perfuming agents.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria-retaining filter, by incorporating sterilizing agents into the compositions, by irradiating the compositions, or by heating the compositions. They can also be manufactured in the form of sterile solid compositions which can be dissolved in sterile water, or some other sterile injectable medium immediately before use.

Compositions for rectal or vaginal administration are preferably suppositories which may contain, in addition to the active substance, excipients such as cocoa butter or a suppository wax.

Compositions for nasal or sublingual administration are also prepared with standard excipients well known in the art.

The dosage of active ingredient in the compositions of this invention may be varied; however, it is necessary that the amount of the active ingredient be such that a suitable dosage form is obtained. The selected dosage depends upon the desired therapeutic effect, on the route of administration, and on the duration of the treatment. Generally, dosage levels of between 0.0001 to 100 mg/kg. of body weight daily are administered to patients and animals, e.g., mammals, to obtain effective release of growth hormone.

The following examples are provided for the purpose of further illustration only and are not intended to be limitations on the disclosed invention.

INTERMEDIATE 1

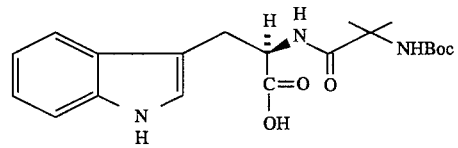

Step A:

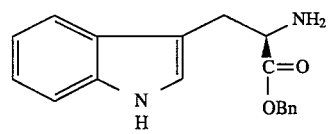

To a solution of the commercially available N-t-BOC-D-tryptophan (25.0 g, 82.2 mmol), benzyl alcohol (10.2 mL, 98.6 mmol), and DMAP (100 mg) in dichloromethane (200 mL) at 0° C., was added EDC (17.4 g, 90.4 mmol) in several portions over a one hour period. The reaction mixture was stirred at room temperature for six hours and was poured into water (200 mL), and the organic layer was separated. The organic solution was washed with a mixture of brine and 3N hydrochloric acid, dried over anhydrous magnesium sulfate, filtered and concentrated to give a thick oil, which solidified upon standing.

To a solution of this oil in 30 mL of dichloromethane was added 20 mL of TFA and stirred for 1 h. The reaction mixture was concentrated, neutralized carefully with saturated aqueous sodium bicarbonate solution, and extracted with dichloromethane (2×100 mL). The combined organic solution was washed with brine (100 mL), passed through a short column of silica gel eluting with 5–10% methanol in dichloromethane to give 23.2 g of the amine as an oil after evaporation.

Step B:

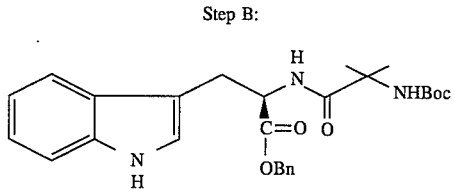

To a solution of the above product, HOBT (10.6 g, 78.8 mmol) and N-BOC-α-methyl alanine (19 g, 94.5 mmol) in 200 mL of dichloromethane, was added EDC (19.5 g, 0.102 mol) in several portions at 0° C. After 5 minutes, the clear reaction mixture became milky. After stirring at room temperature overnight, the reaction mixture was poured into 200 mL of water and the organic layer was separated. The organic solution was washed with brine, and with a brine and saturated sodium bicarbonate solution, dried over anhydrous magnesium sulfate, filtered and concentrated to give a thick oil, which was purified by flash chromatography eluting with 10–40% ethyl acetate in hexane to give the desired material (28.7 g).

$^1$H NMR (CDCl$_3$, 200 MHz) δ8.48 (br.s, 1H), 7.54 (br.d, 1H), 7.38–7.23 (m, 3H), 7.19 (br.d, 2H), 7.15–7.00 (m, 1H), 6.90 (d, 1H), 6.86 (d, 1H), 5.06 (br.s, 2H), 4.95 (ddd, 1H), 3.30 (2 dd, 2H), 1.40 (s, 15H)

Step C:

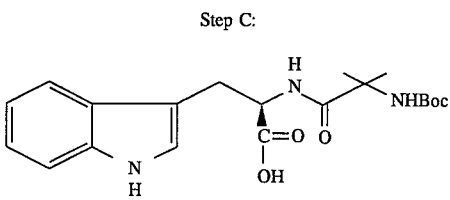

A solution of the material from Step B (28.7 g) in 200 mL of ethanol was stirred at RT under a H$_2$ balloon for 20 minutes in the presence of 10% palladium on carbon (2 g). The catalyst was filtered off through a pad of celite and washed with ethyl acetate. The filtrate was concentrated to give the acid as a slightly pink foam (23.3 g).

$^1$H NMR (CD$_3$OD, 400 MHz) δ7.56 (d,J=8 Hz, 1H), 7.31 (dd, J=1,8 Hz, 1H), 7.09 (s, 1H), 7.07 (dt, J=1,7 Hz, 1H), 6.98 (dt, J=1, 7 Hz, 1H), 4.69 (t, J=6 Hz, 1H), 3.34–3.23 (m, 2H), 1.35 (s, 3H), 1.34 (s, 9H), 1.29 (s, 3H).

FAB-MS calc. for C$_{20}$H$_{27}$N$_3$O$_5$:389; Found 390 (M+H), 290 (M+H-100 (BOC))

INTERMEDIATE 2

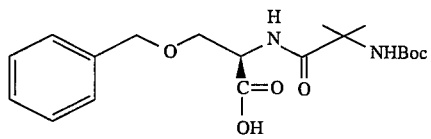

Following the procedures for the preparation of Intermediate 1 using N-t-Boc-O-Benzyl-D-serine in the place of N-t-BOC-D-tryptophan gave Intermediate 2. FAB-MS calc. for C$_{19}$H$_{28}$N$_2$O$_6$:380; Found 381 (M+H), 325 (M+H-56 (t-Bu)), 281 (M+H-100 (BOC)).

INTERMEDIATE 3

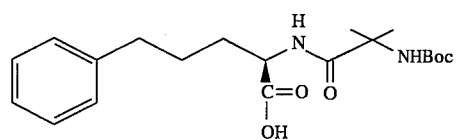

Step A: (DL)-N-Acetyl-2-amino-5-phenylpentanoic acid

To a solution of sodium (2.3 g, 0.1 mol) in ethanol (60 mL) under nitrogen at room temperature, was added diethyl acetamidomalonate. The mixture was stirred at room temperature for one hour, and then 1-bromo-3-phenylpropane was added dropwisely. After the addition, the mixture was stirred at room temperature for two hours, then refluxed overnight. It was cooled to room temperature and partitioned between water and ethyl acetate. The organic layer was washed with sodium bicarbonate in water, dried over MgSO4 and evaporate to give an intermediate (32.5 g, 97%).

$^1$H NMR (CDCl3, 400 MHz) 7.26–7.10 (m, 5H); 6.75 (br.s, 1H); 4.19 (q, J=7 Hz, 4H); 2.58 (t, J=7.9 Hz, 2H); 2.39–2.35 (m, 2H); 2.00 (s, 3H); 1.43–1.39 (m, 2H); 1.20 (t, J=7 Hz, 6H).

The product above was suspended in 190 mL of 2.5N NaOH in water and refluxed for two hours. The mixture was cooled to 0° C., and it was carefully neutralized with 6N NCl to pH2. The precipitate was collected using a glass sinter funnel and washed with a small amount of cold water and air dried. The solid was then suspended in 300 mL of water and refluxed for four hours. The solution was cooled and acidified to pH1 and the solid was collected by filtration (15.3 g, 67%).

$^1$H NMR (CD3OD, 400 MHz) 7.26–7.12 (m, 5H); 4.90–4.37 (m, 1H); 2.65–2.60 (m, 2H); 1.97 (s, 3H); 1.87–1.82 (m, 1H); 1.73–1.65 (m, 3H).

Step B: (D)-N-Acetyl-2-amino-5-phenylpentanoic acid

The racemic intermediate from the previous step (10 g, 42.5 mmol) and CoCl3-6H$_2$O were dissolved in 21 ml of 2N KOH and 200 mL of water at 40° C., and the pH of the solution was adjusted to 8 by the addition of the several drops of 2N KOH. Then acylase I (Aspergillus sp, 0.5 u/mg, from Sigma; 0.9 g) was added with vigorous stirring. The reaction mixture was stirred for one day at 40° C. and the pH was kept at 8 by the addition of a few drops of KOH. The solid which formed was filtered off. The filtrate was acidified by 3N HCl to pH2, and was extracted with ethyl acetate (200 mL×4). The organic extracts were combined and evaporated to give a white solid (4.64 g, 46%)

$^1$H NMR (CD3OD, 400 MHz) 7.26–7.12 (m, 5H); 4.90–4.37 (m, 1H); 2.65–2.60 (m, 2H); 1.97 (s, 3H); 1.87–1.82 (m, 1H); 1.73–1.65 (m, 3H).

Step C: (D)-N-t-Boc-2-amino-5-phenylpentanoic acid

The intermediate from step B (4.2 g, 17.8 mmol) was suspended in 2N HCl (100 mL) and refluxed for two hours. The reaction mixture was evaporated in vacuo to remove water and hydrochloric acid to yield a white solid. To a solution of this solid in 50 mL of water, was added 3N NaOH until the pH 11, then di-t-butyl dicarbonate (4.66 g, 21.4 mmol) was added with vigorous stirring. After four hours, the reaction mixture was acidified to pH2 with 3N HCl and it was extracted with ethyl acetate (100 mLX3). The organic extracts were combined and evaporated to give a white solid (6.56 g, crude) which was used without purification. $^1$H NMR (CD3OD, 400 MHz) 7.26–7.12 (m, 5H); 4.11–4.08 (m, 1H); 2.65–2.60 (m, 2H); 1.83–1.62 (m, 4H); 1.43 (s, 9H).

Step D:

Following the procedures for the preparation of Intermediate 1 using (D)-N-t-Boc-2-amino-5-phenylpentanoic acid in the place of N-t-BOC-D-tryptophan gave Intermediate 3. $^1$H NMR (CDCl$_3$, 400 MHz) 7.24–7.20 (m, 2H), 7.15–7.04 (m, 3H), 4.60–4.55 (m, 1H), 2.62–2.55 (m, 2H), 2.00–1.86 (m, 1H), 1.78–1.60 (m, 3H), 1.50 (s, 6H), 1.30 (s, 9H).

EXAMPLE 1

Example 1

Step A:

To a stirred solution of ethyl nipecotate (15 g, 95.4 mmol) and DMAP (0.05 eq.) in dichloromethane at 0° C. was added dropwise by an addition funnel di-tert-butyl dicarbonate (21.8 g, 100 mmol) in dichloromethane (200 mL). The mixture was stirred for 2–3 hours. The solution was washed with 3N HCl and saturated sodium chloride, dried over anhydrous magnesium sulfate; then filtered and concentrated to give the desired product (18.7 g, 88%).

Step B:

To a stirred solution of ethyl N-t-Boc nipecotate (7 g, 26.90 mmol) in THF (100 mL) at −78° C. under argon was added LHMDS (28 mL, 28 mmol) over a 10 minute period. The solution was allowed to stir an additional 30 minutes at −78° C.; then benzyl bromide (4.8 g, 28 mmol) was added slowly to the solution. The reaction mixture was stirred overnight and allowed to warm to room temperature. The material was concentrated, then diluted with water, and extracted using ethyl acetate (2×200 mL). The organic layer was dried over anhydrous magnesium sulfate, filtered, and concentrated. Purification by silica gel flash column chromatography, eluting with 20% ethyl acetate in hexane, provided the title compound. (8.32 g, 88%).

FAB-MS calc. for C$_{20}$H$_{29}$NO$_4$:347; Found 348 (M+H)

Step C:

A solution of the intermediate from Step B (8 g, 23.02 mmol) in ethyl acetate (80 mL) was cooled to 0° C. While stirring, hydrogen chloride gas was bubbled into the mixture until saturation occurred. The reaction was stirred for 40 minutes, until TLC analysis indicated that the reaction was complete. The solution was then concentrated to remove the ethyl acetate to afford the product (6.53 g, 99%).

$^1$H NMR (CDCl$_3$, 400 MHz) δ7.25–7.19 (m, 3H), 7.04–7.01 (m, 2H), 5.35 (v.br.s, 2H), 4.22–4.10 (m, 2H), 3.44 (d, J=13 Hz, 1H), 3.21 (br. d, J=12.7 Hz, 1H), 2.95 (d, J=13.5 Hz, 1H), 2.76–2.68 (m, 3H), 2.22 (br.d, J=13 Hz, 1H), 1.73–1.71 (m, 1H), 1.61–1.48 (m, 2H), 1.18 (t, J=7 Hz, 3H).

FAB-MS calc. for C$_{15}$H$_{21}$NO$_2$:247; Found 248 (M+H)

Step D:

and

To a solution of the intermediate prepared in the previous step (1.2 g, 4.23 mmol), and Intermediate 1 (1 eq.), HOBT (1 eq.), and N-methyl morpholine (1 eq.) in dichloromethane cooled to 0° C. was added EDC (1.5 eq.). The reaction mixture was stirred at 0° C. overnight. The solution was washed with saturated sodium chloride, dried over anhydrous magnesium sulfate; then filtered and concentrated. Purification by MPLC eluting with 40% ethyl acetate in hexane provided two enantiomerically pure compounds. The compound which came out first from the column was designated as d1 (1.14 g), which has an R-absolute stereochemistry at the 3-position of the nipecotate; and the compound which came out of the column second was designated as d2 (1.08 g), which has an S-absolute stereochemistry (see Example 2 for assignment) at the 3-position of the nipecotate.

d1 FAB-MS calc. for $C_{35}H_{46}N_4O_6$: 618; Found 619 (M+H)

d2 FAB-MS calc. for $C_{35}H_{46}N_4O_6$: 618; Found 619 (M+H)

Step E:

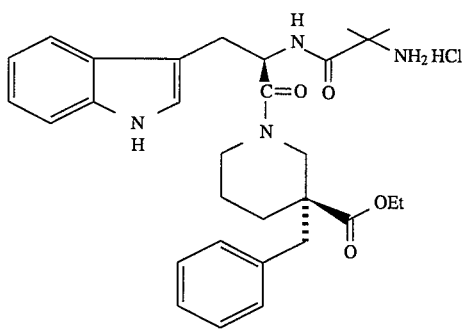

Prepared by the procedure described in Step C from the intermediates d1 from the previous step (1 g) in ethyl acetate (20 mL) and HCl gas at 0° C. for 1.5 hours. Product: 860 mg, 91%.

FAB-MS calc. for $C_{30}H_{38}N_4O_4$: 518; Found 519 (M+H)

EXAMPLE 1A

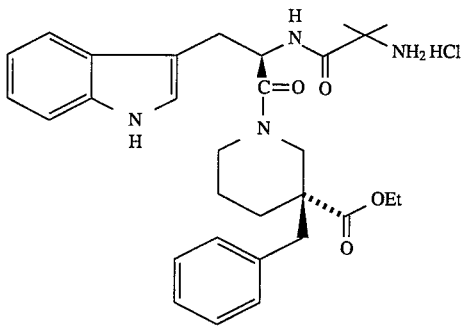

Prepared by the procedure described in Step C of Example 1 from 1 g of the d2 intermediates from the Step D of Example 1 in ethyl acetate (20 mL) by bubbling HCl at 0° C. until saturated and then evaporated after 30 minutes to give the title compound (878 mg, 93%). FAB-MS calc. for $C_{30}H_{38}N_4O_4$: 518; Found 519 (M+H)

$^1$H NMR (CD$_3$OD, 400 MHz) compound exists in two rotamers in approximately a 5/3 ratio that slowly interconvert relative to the NMR time scale δ7.60 (d, J=7.9 Hz, 5/8H), 7.55 (d, J=7.9 Hz, 3/8H), 7.34–6.93 (m, 9H), 5.36 (dd, J=5.2 Hz, 9.7 Hz, 3/8H), 5.31 (dd, J=6.7 Hz, 8.8 Hz, 5/8H), 4.23 (br. d, J=13.7 Hz, 3/8H), 4.10–4.00 (m, 6/8H), 4.04–3.98 (m,3/8H), 3.96–3.82 (m, 10/8H), 3.80 (br. d, J=13.5 Hz, 5/8H), 3.36 (br. d, J=13.3 Hz, 5/8H), 3.29–3.22, 3.17–3.10, (2m, 2H), 3.20 (br. d, J=14.5 Hz, 3/8H), 3.10–2.96 (m, 5/8H), 2.90 (s, 6/8H), 2.60 (d, J=13.4 Hz, 5/8), 2.41 (d, J=13.4 Hz, 5/8H), 2.19–2.12, 1.82–1.70, 1.68–1.60, 1.50–1.40, 1.34–1.25, 1.05–0.95 (6m, 4H), 1.55 (s, 9/8H), 1.50 (s, 15/8H), 1.09 (t, J=7.1 Hz, 3H).

The additional intermediates shown in Table I were prepared according to the above established procedures as exemplified in Example 1 steps A through C. The final compounds were prepared according to Example 1 Steps D and E, and Example Ia using Intermediate 1.

TABLE I

ADDITIONAL EXAMPLES

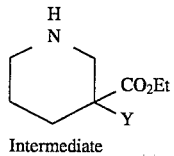

Intermediate

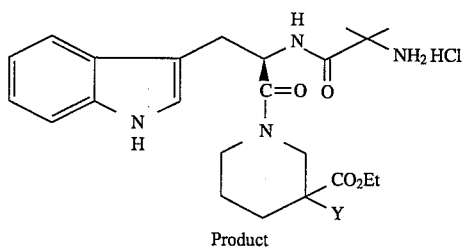

Product

| entry | Y | Intermediate MF FAB-MS (M + 1) | Product MF FAB-MS (M + 1) | isomer[a] |
|---|---|---|---|---|
| 1 | Me | $C_9H_{17}NO_2$ 171 (M+,EI-MS) | $C_{24}H_{34}N_4O_4$ 443 | d1 d2 |

TABLE I-continued

ADDITIONAL EXAMPLES

Intermediate

Product

| entry | Y | Intermediate MF FAB-MS (M + 1) | Product MF FAB-MS (M + 1) | isomer[a] |
|---|---|---|---|---|
| 2 | Et | $C_{10}H_{19}NO_2$ 185 (M+,EI-MS) | $C_{25}H_{36}N_4O_4$ 457 | d1 d2 |
| 3 | n-Pr | $C_{11}H_{21}NO_2$ 199 (M+,EI-MS) | $C_{26}H_{38}N_4O_4$ 471 | d1 d2 |
| 4 | allyl | $C_{11}H_{19}NO_2$ 198 | $C_{26}H_{36}N_4O_4$ 469 | d1 d2 |
| 5 | n-Bu | $C_{12}H_{23}NO_2$ 213 (M+,EI-MS) | $C_{27}H_{40}N_4O_4$ 485 | d1 d2 |
| 6 | —CH2OEt | $C_{11}H_{21}NO_3$ 216 | $C_{26}H_{38}N_4O_5$ 487 | RS |
| 7 | cyclohexane-methyl | $C_{15}H_{27}NO_2$ 254 | $C_{30}H_{44}N_4O_4$ 525 | d1 d2 |
| 8 | Ph(CH$_2$)$_2$— | $C_{16}H_{23}NO_2$ 261 (M+,EI-MS) | $C_{31}H_{40}N_4O_4$ 533 | d1 d2 |
| 9 | Ph(CH$_2$)$_3$— | $C_{17}H_{25}NO_2$ 275 (M+,EI-MS) | $C_{32}H_{42}N_4O_4$ 547 | d1 d2 |
| 10 | o-MeOBn— | $C_{16}H_{23}NO_3$ 278 | $C_{31}H_{40}N_4O_5$ 549 | d1 d2 |
| 11 | m-MeOBn— | $C_{16}H_{23}NO_3$ 278 | $C_{31}H_{40}N_4O_5$ 549 | d1 d2 |
| 12 | p-MeOBn— | $C_{16}H_{23}NO_3$ 278 | $C_{31}H_{40}N_4O_5$ 549 | d1 d2 |
| 13 | o-Me—Bn— | $C_{16}H_{23}NO_2$ 262 | $C_{31}H_{40}N_4O_4$ 533 | d1 d2 |
| 14 | m-Me—Bn— | $C_{16}H_{23}NO_2$ 262 | $C_{31}H_{40}N_4O_4$ 533 | d1 d2 |
| 15 | p-Me—Bn— | $C_{16}H_{23}NO_2$ 262 | $C_{31}H_{40}N_4O_4$ 533 | d1 d2 |
| 16 | o-Cl—Bn— | $C_{15}H_{20}NO_2Cl$ 282,284 (3:1) | $C_{30}H_{37}N_4O_4Cl$ 554,556 (3:1) | d1 d2 |
| 17 | m-Cl—Bn— | $C_{15}H_{20}NO_2Cl$ 282,284 (3:1) | $C_{30}H_{37}N_4O_4Cl$ 554,556 (3:1) | d1 d2 |
| 15 | p-Cl—Bn— | $C_{15}H_{20}NO_2Cl$ 282,284 (3:1) | $C_{30}H_{37}N_4O_4Cl$ 554,556 (3:1) | d1 d2 |
| 16 | 2,6-di-Cl—Bn— | $C_{15}H_{19}NO_2Cl_2$ 316,318,320 | $C_{30}H_{36}N_4O_4Cl_2$ 587,589,591 | |
| 17 | p-Br—Bn— | $C_{15}H_{20}NO_2Br$ 326,328 (1:1) | $C_{30}H_{37}N_4O_4Br$ 597,599 (1:1) | d1 d2 |
| 18 | m-Br—Bn— | $C_{15}H_{20}NO_2Br$ 326,328 (1:1) | $C_{30}H_{37}N_4O_4Br$ 597,599 (1:1) | d1 d2 |
| 19 | o-nitro-Bn— | $C_{15}H_{20}N_2O_4$ 293 | $C_{30}H_{37}N_5O_6$ 564 | d1 d2 |
| 20 | m-nitro-Bn— | $C_{15}H_{20}N_2O_4$ 293 | $C_{30}H_{37}N_5O_6$ 564 | d1 d2 |
| 21 | p-nitro-Bn— | $C_{15}H_{20}N_2O_4$ 293 | $C_{30}H_{37}N_5O_6$ 564 | d1 d2 |
| 22 | 1-naphthylmethyl | $C_{19}H_{23}NO_2$ 298 | $C_{34}H_{40}N_4O_4$ 569 | d1 d2 |
| 23 | (5-chloro-2-thienyl)methyl | $C_{13}H_{18}NO_2SCl$ 288,290 (3:1) | $C_{28}H_{35}N_4O_4SCl$ 559,561 (3:1) | d1 d2 |

TABLE I-continued

ADDITIONAL EXAMPLES

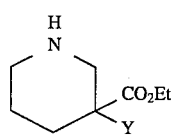
Intermediate

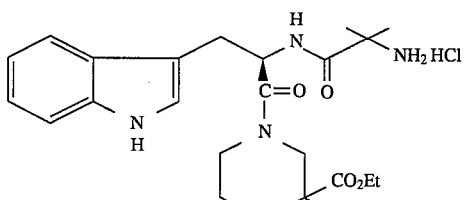
Product

| entry | Y | Intermediate MF FAB-MS (M + 1) | Product MF FAB-MS (M + 1) | isomer[a] |
|---|---|---|---|---|
| 24 | BnO$_2$C— | C$_{16}$H$_{21}$NO$_4$ 292 | C$_{31}$H$_{38}$N$_4$O$_6$ 563 | RS |
| 25 | EtO$_2$C— | C$_{11}$H$_{19}$NO$_4$ 230 | C$_{26}$H$_{36}$N$_4$O$_6$ 501 | RS |
| 26 | p-Ph—Bn— | C$_{21}$H$_{25}$NO$_4$ 324 | C$_{36}$H$_{42}$N$_4$O$_4$ 595 | d1 d2 |
| 27 | ![benzodioxole-Cl-CH2] | C$_{16}$H$_{20}$NO$_4$Cl 326,328 (3:1) | C$_{31}$H$_{37}$N$_4$O$_6$Cl 597,599 (3:1) | d1 d2 |
| 28 | ![phthalimido-CH2] | C$_{17}$H$_{20}$N$_2$O$_4$ 317 | C$_{32}$H$_{37}$N$_5$O$_6$ 588 | d1 d2 |

[a]: In this and in subsequent tables for isomer designation: R or S means the stereochemistry at the carbon atom to which X and Y are attached, RS means it is a mixture of the two isomers at this center; d1 or d2 means the two diastereomers were separated and are as defined in Example 1 step D.

The additional examples shown in Table Ia were prepared according to Example 1 Steps D and E, using Intermediate 1 and commercially available intermediates.

TABLE Ia
ADDITIONAL EXAMPLES

Intermediate: 3-X-piperidine (with NH)

Product: tryptophan-derived amide coupled to 2-amino-2-methyl group (NH$_2$·HCl) with C=O linked to N of 3-X-piperidine

| entry | X | Product MF FAB-MS (M + 1) | isomer |
|---|---|---|---|
| 1 | —OH | $C_{20}H_{28}N_4O_3$ 373 | RS |
| 2 | —CH2OH | $C_{21}H_{30}N_4O_3$ 387 | RS |
| 3 | —CO2Et | $C_{23}H_{32}N_4O_4$ 429 | RS |
| 4 | CO2Bn | $C_{28}H_{34}N_4O_4$ 491 | RS |
| 5 | CONMe2 | $C_{23}H_{33}N_5O_3$ 428 | RS |

The additional Products shown in Table Ib were prepared according to Example 1 Steps D and E, using Intermediate 3 and some of the intermediates shown in Table 1.

TABLE Ib
ADDITIONAL EXAMPLES

Structure: Ph(CH$_2$)$_3$-CH(NHC(=O)C(CH$_3$)$_2$NH$_2$·HCl)-C(=O)-N(piperidine with CO$_2$Et and Y at 3-position)

| entry | Y | Product MF FAB-MS (M + 1) | isomer |
|---|---|---|---|
| 1 | Bn | $C_{30}H_{41}N_3O_4$ 508 | R |
| 2 | Bn | $C_{30}H_{41}N_3O_4$ 508 | S |
| 3 | Ph(CH$_2$)$_2$ | $C_{31}H_{43}N_3O_4$ 522 | d1 d2 |
| 4 | Ph(CH$_2$)$_3$ | $C_{32}H_{45}N_3O_4$ 536 | d1 d2 |
| 5 | 1-naphthylmethyl | $C_{34}H_{43}N_3O_4$ 558 | RS |

TABLE Ib-continued
ADDITIONAL EXAMPLES

| entry | Y | MF FAB-MS (M + 1) | isomer |
|---|---|---|---|
| 6 | 5-chloro-2-thienyl-CH$_2$— | $C_{28}H_{38}N_3O_4SCl$ 548,550 (3:1) | RS |
| 7 | p-Ph—Bn— | $C_{36}H_{45}N_3O_4$ 584 | RS |
| 8 | BnO$_2$C— | $C_{31}H_{41}N_3O_6$ 552 | RS |
| 9 | 6-chloro-1,3-benzodioxol-5-yl-CH$_2$— | $C_{31}H_{40}N_3O_6Cl$ 586,588 (3:1) | d1 d2 |

The additional products shown in Table Ic were prepared according to Example 1 Steps D and E, using Intermediate 2 and some of the intermediates shown in Table I.

TABLE Ic
ADDITIONAL EXAMPLES

Structure: PhCH$_2$O-CH$_2$-CH(NHC(=O)C(CH$_3$)$_2$NH$_2$·HCl)-C(=O)-N(piperidine with CO$_2$Et and Y at 3-position)

| entry | Y | MF FAB-MS (M + 1) | isomer |
|---|---|---|---|
| 1 | Bn | C29H39N3O5 510 | R |
| 2 | Bn | C29H39N3O5 510 | S |
| 3 | Et | C24H37N3O5 448 | RS |
| 4 | Ph(CH$_2$)$_2$ | C30H41N3O5 524 | d1 d2 |
| 5 | Ph(CH$_2$)$_3$ | C31H43N3O5 538 | d1 d2 |
| 6 | H | C22H33N3O5 420 | RS |

TABLE Ic-continued

EXAMPLE 2

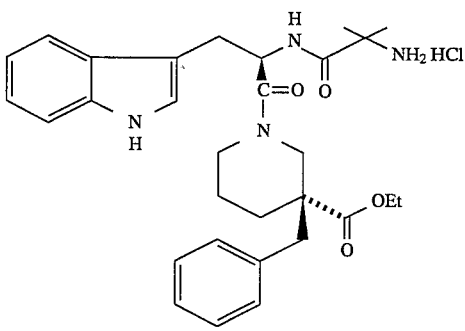

Step A:

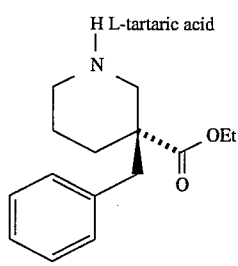

The intermediate from Example 1, Step C (50.8 g) was dissolved in dichloromethane and it was washed with 3N NaOH. The aqueous layer was extracted with dichloromethane and the combined solution was dried (MgSO₄) and evaporated to give the free amine as an oil. The ethyl 3-benzyl nipecotate and D-tartaric acid (31 g) were dissolved in 880 mL of water/acetone (1:4) solution with heating. The solution was left in the refrigerator overnight and the crystals which were formed were filtered off. Recrystallization in 470 mL of water/acetone (1:4) at room temperature gave the ethyl 3-(R)-benzyl nipecotate D-tartaric acid salt (21 g).

The structure of this compound was determined by X-Ray crystallographic analysis. With the configuration of D-tartaric acid known to be S,S, the configuration of the chiral site in this ethyl 3-benzylmipecotate salt was determined to be R.

The combined mother liquor was evaporated and to it was added 3N NaOH and dichloromethane, the mixture was stirred for 30 minutes and the organic layer was separated. The aqueous was extracted twice with dichloromethane and the combined organic extracts were dried over MgSO4 and evaporated to give 24.4 g of the S-isomer enriched compound. It was crystallized with L-tartaric acid (14.8 g) in 400 mL of water/acetone (1:4) at room temperature to give ethyl 3 (S)-benzyl nipecotate L-tartaric acid salt (27.3 g).

¹H NMR (CD₃OD, 400 MHz) δ7.31–7.22 (m, 3H), 7.12–7.09 (m, 2H), 4.40 (s, 2H, from tartaric acid), 4.30–4.10 (m, 2H), 3.49 (br. d, J=13 Hz, 1H), 3.06 (d, J=13.6 Hz, 1H), 2.98 (d, J=13 Hz, 1H), 2.92 (dt, J=3.3 Hz, 13 Hz, 1H), 2.82 (d, J=13.6 Hz, 1H), 2.30 (d, J=12.4 Hz, 1 H), 1.88 (td, J=3 Hz, 14.5 Hz, 1H), 1.69 (dt, J=3 Hz, 13 Hz, 1H), 1.63–1.51 (m, 1H), 1.25b (q, J=7.1 Hz, 3H).

Step B:

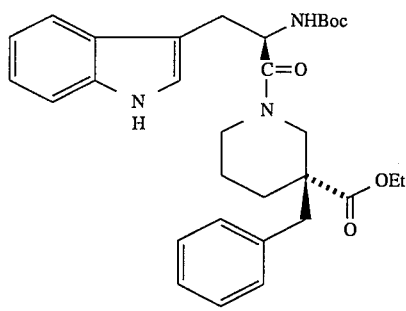

Ethyl 3 (S)-benzyl nipecotate L-tartaric acid salt (39.74 g) was suspended in 70 mL of 3N NaOH and 70 mL of water, followed by extraction with dichloromethane. The extracts were combined, dried, and evaporated to give a thick oil. To a stirred solution of the oil, N-t-Boc D-TrpOH (30.43 g) and HOBt (13.5 g) in dichloromethane (200 mL) at 0° C., was added EDC (23 g) in several portions. The mixture was stirred overnight and it was poured into water and 3N HCl and was extracted with dichloromethane. The organic layer was washed with brine, saturated sodium bicarbonate, dried over MgSO₄ and evaporated to give a crude product (67.7 g), which was used without further purification.

FAB-MS calc. for $C_{31}H_{39}N_3O_5$:533; Found 534 (M+H)

Step C:

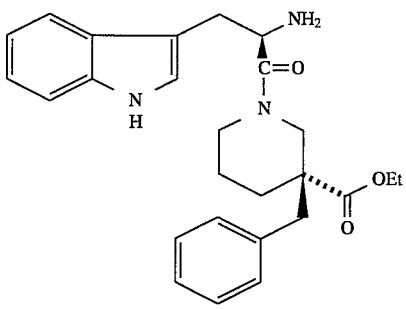

To a solution of the intermediate from the previous step (67.7 g crude) in ethyl acetate (100 mL) at 0° C., was bubbled HCl gas until it was saturated. The reaction mixture was stirred at 0° C. for 30 minutes and was evaporated to remove excess HCl and ethyl acetate. The residue was suspended in dichloromethane and was washed with a mixture of 3N NaOH (70 mL) and water (100 mL). The organic layer was dried (MgSO₄), evaporated to a small volume and used in next step without further purification.

FAB-MS calc. for $C_{26}H_{31}N_3O_3$:433; Found 434 (M+H)

Step D:

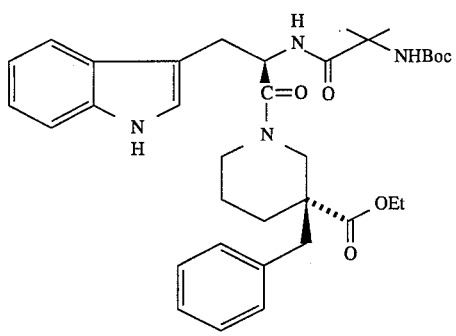

A solution containing the intermediate obtained in the last step, N-Boc-α-Me-AlaOH (20.3 g), and DMAP (200 mg) in dichloromethane (100 mL) was stirred at room temperature and to it was added EDC (24 g) in several portions. The reaction mixture was stirred for 3 hours and was worked up by diluting it with dichloromethane and washing with 3N HCl, brine, and saturated sodium bicarbonate solution. The organic layer was dried over MgSO₄, and evaporated to give a thick oil. This oil was passed through a pad of silica gel, eluting with 60% ethyl acetate in hexane to remove some very polar impurities, to give the desired compound (54.2 g)

FAB-MS calc. for $C_{35}H_{46}N_4O_6$:618; Found 619 (M+H)

Step F:

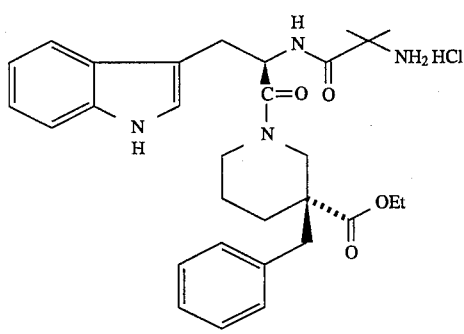

To a solution of the intermediate from the previous step (54.2 g) in ethyl acetate (100 mL) at 0° C., was bubbled HCl gas until it was saturated. The reaction mixture was stirred at 0° C. for 15 minutes and was evaporated to remove excess HCl and ethyl acetate. The residue was first dissolved in dichloromethane (100 mL) and then ethyl acetate (300 mL) was added. The mixture was stirred overnight and the solid was collected by filtration to give the title compound (34 g). Further evaporation of the mother liquor to a small volume gave the second crop of product (10.1 g).

MS and NMR identical with Example 1A.

The additional products shown in Table II were prepared according to Example 2, Steps B through F, using the readily available Boc protected amino acids instead of N-t-Boc-D-TrpOH.

TABLE II

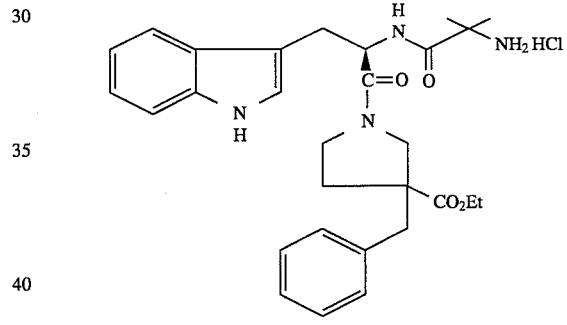

Product

| entry | R | MF<br>FAB-MS (M + 1) |
|-------|------|----------------------|
| 1 | 4-F | C30H37N4O4F<br>537 |
| 2 | 5-F | C30H37N4O4F<br>537 |
| 3 | 6-F | C30H37N4O4F<br>537 |
| 4 | 1-Me | C31H40N4O4<br>533 |
| 5 | 5-MeO | C31H40N4O5<br>549 |
| 6 | 5-HO | C30H38N4O5<br>535 |
| 7 | 6-MeO | C31H40N4O5<br>549 |

EXAMPLE 3

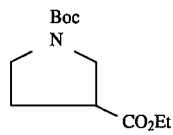

Step A:

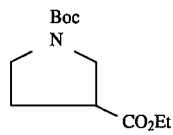

To a stirred solution of ethyl 3-pyrrolidinecarboxylate hydrochloride (J. Chem. Soc., 24, 1618–1619; 10 g, 69.8 mmol), triethylamine (7.75 mL) and DMAP (857 mg) in dichloromethane (40 mL), was slowly added di-t-butyl dicarboxylate (18.3 g, 83.7 mmol) and the resulting mixture was stirred at room temperature for three days. The mixture was then concentrated, washed with 3N HCl and dried and evaporated to give the intermediate.

Step B:

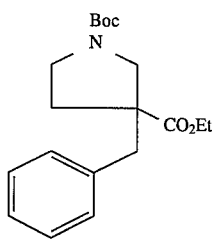

Prepared by the procedure described in Example 1, Step B from the intermediate obtained from previous step (500 mg, 2.05 mmol), KHMDS (512 mg, 2.57 mmol) and benzyl bromide (371 mg, 2.16 mmol). Purification by silica gel flash column eluting with 5–20% ethyl acetate in hexane provided the title compound (385 mg, 56%).

Step C:

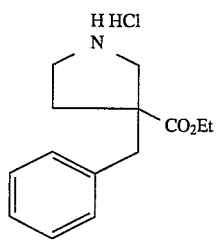

Prepared by the procedure described in Example 1, Step C from the intermediate from the previous step (385 mg, 1.16 mmol) in ethyl acetate (5 mL) and HCl gas at 0° C. for 15 minutes (306 mg, 98%).

Step D:

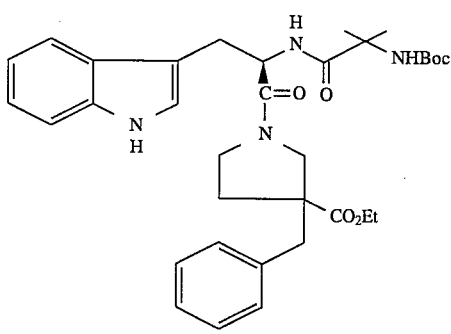

Prepared by the procedure described in Example 1, Step D from the intermediate prepared in the previous step (138 mg, 0.514 mmol), intermediate 1 (200 mg, 0.514 mmol), HOBT (1 eq.), N-methyl morpholine (1 eq.), and EDC (2 eq.). Purification by MPLC, eluting with 60% ethyl acetate in hexane gave the product (250 mg, 80%)

FAB-MS calc. for $C_{34}H_{44}N_4O_6$: 604; Found 605 (M+H).

Step E:

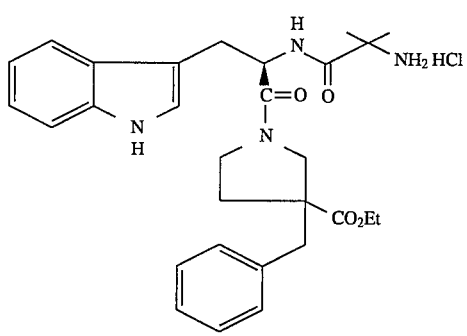

Prepared by the procedure described in Example 1, Step C from the intermediate from the previous step (250 mg, 0.036 mmol) in ethyl acetate (3 mL) and HCl gas at 0° C. for 10 minutes.

FAB-MS calc. for $C_{29}H_{36}N_4O_4$:504; Found 505 (M+H).

EXAMPLE 4

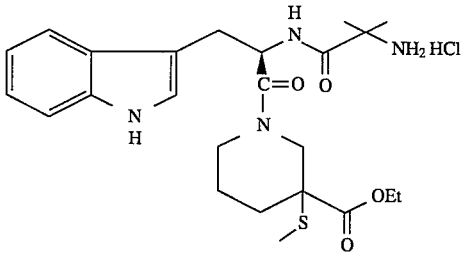

Step A:

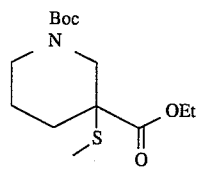

To a stirred solution of ethyl N-t-Boc nipecotate (4 g, 15.7 mmol)) in THF (100 mL) at −78° C. under argon was added LHMDS (1M, 32 mL, 32 mmol) over a 10 minute period. The solution was allowed to stir an additional 30 minutes at −78° C.; then methyl disulfide (1.92 g, 20.37 mmol) was added slowly to the solution. The reaction mixture was stirred overnight and allowed to warm to room temperature. The material was concentrated, then diluted with water, and extracted using ethyl acetate (2×200 mL). The organic layer was dried over anhydrous magnesium sulfate, filtered, and concentrated. Purification by silica gel flash column chromatography eluting with 20% ethyl acetate in hexane provided the title compound.

FAB-MS calc. for $C_{14}H_{25}NO_4S$:271; Found 272 (M+H)

Step B:

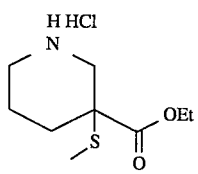

Prepared by the procedure described in Example 1, Step C from the intermediate from the previous step (1 g, 3.3 mmol) in ethyl acetate (25 mL) and HCl gas at 0° C. for 35 minutes to yield the product (783 mg, 99%).

FAB-MS calc. for $C_9H_{17}NO_2S$: 171; Found 271 (M+H)

Step C:

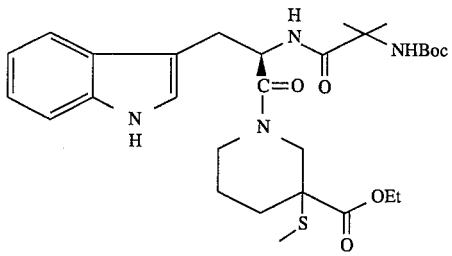

Prepared by the procedure described in Example 1, Step D from the intermediate prepared in the previous step (123 mg, 0.514 mmol), Intermediate 1 (1 eq.), HOBT (1 eq.), NMM (1 eq.), and EDC (197 mg, 1.028 mmol). Purification by MPLC provided diastereomers. The compound which came out first from the column was designated as d1 (109 mg, 37%); and the compound which came out of the column second was designated as d2 (88 mg, 30%), d1 FAB-MS calc. for $C_{29}H_{42}N_4O_6S$:574; Found 575 (M+H)

d2 FAB-MS calc. for $C_{29}H_{42}N_4O_6S$:574; Found 575 (M+H)

Step D:

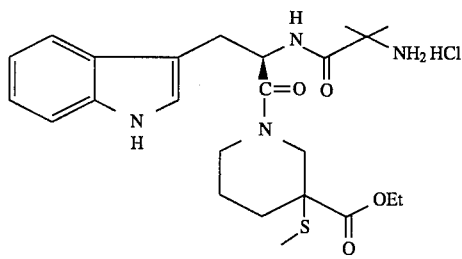

Prepared by the procedure described in Example 1, Step C from the intermediates d1 (80 mg) and d2 (80 mg) separately from the previous step in ethyl acetate (5 mL each) and HCl gas at 0° C. for 20 minutes.

d1: (71 mg, 99%)

d2: (70 mg, 98%)

d1 $^1$H NMR (CD$_3$OD,400 MHz): The compound exists in two rotamers in approximately a 1:1 ratio. δ7.71 (d,J=7.2 Hz, 1/2H), 7.56 (d,J=7.2 Hz, 1/2H), 7.38 (d,J=8.0 Hz, 1/2H), 7.33 (d,J=7.5 Hz, 1/2H), 7.14–7.01 (m,3H), 5.44 (dd,J=6 Hz, 8 Hz, 1/2H), 4.30–4.10 (m,5/2H), 3.92 (d,J=13.3 Hz, 1/2H), 3.81 (d,J=13.3 Hz, 1/2H), 3.67 (d,J=13.3 Hz, 1/2H), 3.48–3.40 (m, 1/2H), 3.28–3.09 (m, 7/2H), 2.55 (dt, 1/2H), 2.26–2.20 (br.d, 1/2H), 2.05 (s,3H), 1.80–1.70 (m, 1/2H), 1.67, 1.59, 1.55, 1.43 (4s, 6H), 1.27 (t,J=7.0 Hz, 3/2H), 1.19 (t,J=7.0 Hz, 3/2H), 0.90–0.85 (m, 1/2H).

d2 $^1$H NMR (CD$_3$OD, 400 MHz): The compound exists in two rotamers in approximately a 1:1 ratio. δ7.77 (d,J=7.5 Hz, 1/2H), 7.56 (d,J=7.9 Hz, 1/2H), 7.35–7.30 (m, 1H), 7.13–6.98 (m, 3H), 5.53 (dd,J=5.5 Hz, 8 Hz, 1/2H), 5.24 (app. t,J=7 Hz, 1/2H), 4.30 (br.d,J=14 Hz, 1/2H), 4.20–4.10 (m, 2H), 3.90–3.85 (m, 1/2H), 3.86 (d,J=13.2 Hz, 1/2H), 3.70 (d,J=13.7 Hz, 1/2H), 3.35–3.10 (m, 4H), 2.30–2.20 (m, 1/2H), 2.12, 2.04 (2s, 3H), 2.04–2.00 (m, 1/2H), 1.80–1.70 (m, 3/2H), 1.54, 1.50, 1.43, 1.26 (4s, 6H), 1.23 (t,J=6.7 Hz, 3H), 0.90–0.84 (m, 1/2H).

d1 FAB-MS calc. for $C_{24}H_{34}N_4O_4S$: 474; Found 475 (M+H)

d2 FAB-MS calc. for $C_{24}H_{34}N_4O_4S$: 474; Found 475 (M+H)

The additional intermediates shown in Table III were prepared according to the above established procedure as exemplified in Example 4 steps A and B. The final compounds were prepared according to Example 4 Steps C and D, using Intermediate 1.

TABLE III

| entry | Y | Intermediate MF FAB-MS (M + 1) | Product MF FAB-MS (M + 1) | isomer |
|---|---|---|---|---|
| 1 | PhS— | $C_{14}H_{19}NO_2S$ | $C_{29}H_{36}N_4O_4S$ | d1 |

TABLE III-continued

| | | 266 | 537 | d2 |
|---|---|---|---|---|
| 2 | BnS— | $C_{15}H_{21}NO_2S$ | $C_{30}H_{38}N_4O_4S$ | d1 |
| | | 280 | 551 | d2 |
| 3 | 2-pyridylthio- | $C_{13}H_{18}N_2O_2S$ | $C_{28}H_{35}N_5O_4S$ | RS |
| | | 267 | 538 | |
| 4 | —S—(structure with N, CH₃, S) | | $C_{27}H_{35}N_5O_4S2$ | RS |
| | | | 558 | |

EXAMPLE 5

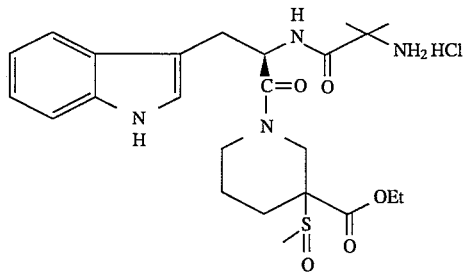

Step A:

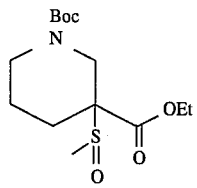

To a stirred solution of NaIO$_4$ (316.5 mg, 1.48 mmol) in water (5 mL) and ethanol (5 mL) was added the intermediate from Example 4, Step A (300 mg, 0.99 mmol). The mixture was stirred for 5 hours at room temperature, then concentrated to remove ethanol. The material was then extracted with ethyl acetate (2×10 mL). The organic layer was dried over magnesium sulfate and concentrated to give the title compound (286 mg, 90.5%).

FAB-MS calc. for $C_{14}H_{25}NO_5S$: 319; Found 320 (M+H)

Step B:

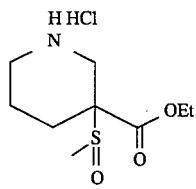

Prepared by the procedure described in Example 1, Step C from the intermediate from the previous step (230 g, 0.72 mmol) in ethyl acetate (10 mL) and HCl gas at 0° C. for 25 minutes (197 mg, 100%).

FAB-MS calc. for $C_9H_{17}NO_3S$: 219; Found 220 (M+H)

Step C:

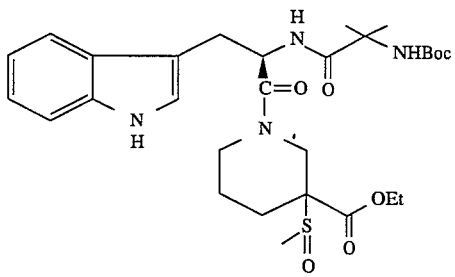

Prepared by the procedure described in Example 1, Step D from the intermediate prepared in the previous step (140 mg, 0.547 mmol), Intermediate 1 (1 eq.), HOBT (1 eq.), N-methyl morpholine (1 eq.), and EDC (210 mg, 1.094 mmol). Purification by MPLC provided a diastereomeric mixture of compounds (177 mg, 55%).

FAB-MS calc. for $C_{29}H_{42}N_4O_7S$: 590; Found 591 (M+H)

Step D:

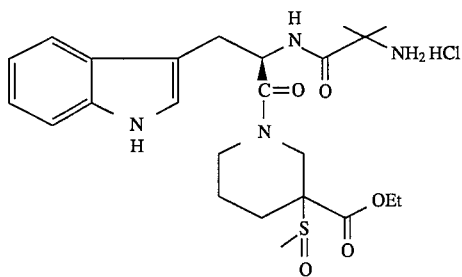

Prepared by the procedure described in Example 1, Step C from the intermediate from the previous step (150 mg, 0.254 mmol) in ethyl acetate (10 mL) and HCl gas at 0° C. for 20 minutes (118 mg, 90%).

FAB-MS calc. for $C_{24}H_{34}N_4O_5S$: 490; Found 491 (M+H)

EXAMPLE 6

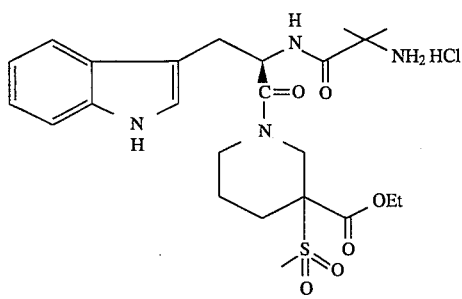

Step A:

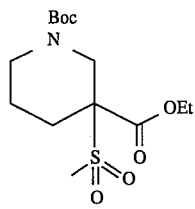

To a stirred solution of Oxone (910 mg, 1.48 mmol) in water (5 mL) and methanol (5 mL) was added the intermediate from Example 4, Step A (300 mg, 0.99 mmol). The mixture was stirred for 4 hours at room temperature, then concentrated to remove methanol. The residue was then extracted with ethyl acetate (2×10 mL). The organic layer was dried over magnesium sulfate and concentrated to give the title compound (321 mg, 97%).

FAB-MS calc. for $C_{14}H_{25}NO_6S$: 335; Found 336 (M+H) [Found 236 (M- t-Boc)]

Step B:

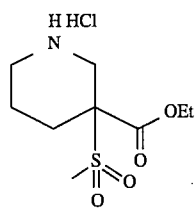

Prepared by the procedure described in Example 1, Step C from the intermediate from the previous step (221 mg, 0.66 mmol) in ethyl acetate (10 mL) and HCl gas at 0° C. for 25 minutes (192 mg, 99%).

FAB-MS calc. for $C_9H_{17}NO_4S$: 235; Found 236 (M+H)

Step C:

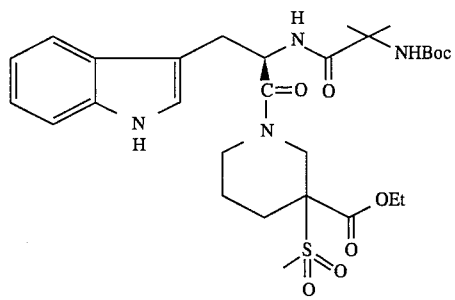

Prepared by the procedure described in Example 1, Step D from the intermediate prepared in the previous step (140 mg, 0.515 mmol), Intermediate 1 (1 eq.), HOBT (1 eq.), N-methyl morpholine (1 eq.), and EDC (197 mg, 1.03 mmol). Purification by MPLC provided a diastereomeric mixture of compounds (251 mg, 80%).

FAB-MS calc. for $C_{29}H_{42}N_4O_8S$: 606; Found 607 (M+H)

Step D:

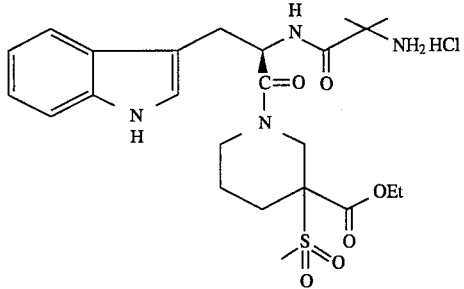

Prepared by the procedure described in Example 1, Step C from the intermediate from the previous step (210 mg, 0.317 mmol) in ethyl acetate (10 mL) and HCl gas at 0° C. for 30 minutes (193 mg, (98.5%) FAB-MS calc. for $C_{24}H_{34}N_4O_8S$: 506; Found 507 (M+H)

EXAMPLE 7

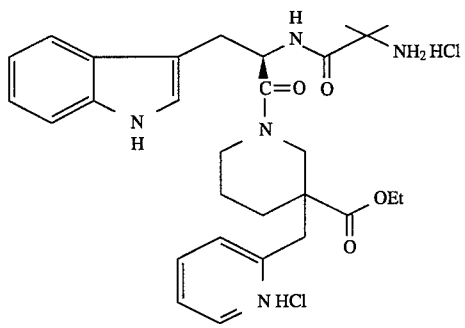

Step A:

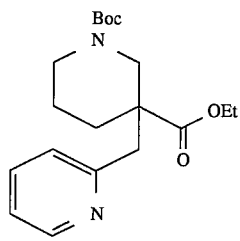

To a stirred solution of ethyl N-t-Boc nipecotate (50 g, 0.196 mol) in THF (600 mL) at −78° C. under argon was added KHMDS (0.5M in toluene, 298 mL, 0.298 mol) over a 30 minute period. The solution was allowed to stir an additional 30 minutes at −78° C. Meanwhile, a suspension of 2-picolyl chloride hydrochloride (25 g) in dichloromethane was washed with a mixture of 3N NaOH and brine to remove the hydrochloride. The organic layer was dried over MgSO$_4$ and evaporated to yield a brown oil and it was added slowly to the solution at −78° C. The reaction mixture was stirred overnight and allowed to warm to room temperature. The material was concentrated, then diluted with water, and extracted using ethyl acetate. The organic layer was dried over anhydrous magnesium sulfate, filtered, and concentrated. Purification by silica gel flash column chromatography eluting with a solvent gradient of 20–80% ethyl acetate in hexane provided the title compound. (54.8 g, 80%). $^1$H NMR (CD$_3$OD, 400 MHz) δ8.45 (dd,J=1.5 Hz, 5 Hz, 1H), 7.52 (app dt, J=2 Hz, 8 Hz, 1H), 7.07 (dd, J=5 Hz, 6.6 Hz, 1H), 7.05 (d, J=8 Hz, 1H), 4.09–4.04 (br.m, 2H), 3.92 (br.d, 1H), 3.46 (br.m, 1H), 3.30–3.10 (br.m, 1H), 3.06 (d, J=13.7 Hz, 1H),2.95(d, J=13.7 Hz, 1H), 2.01–1.91 (br.m, 1H), 1.63–1.50 (br.m, 3H), 1.36 (v.br.s, 9H), 1.13 (t, 7.1 Hz, 3H). FAB-MS calc. for C$_{19}$H$_{28}$N$_2$O$_4$: 348; Found 349 (M+H)

Step B

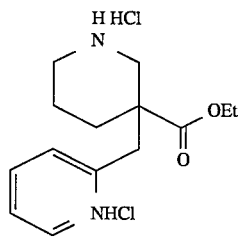

Prepared by the procedure described in Example 1, Step C from the intermediate from the previous step (6.36 g, 18.2 mmol) in ethyl acetate (100 mL) and HCl at 0° C. for 45 minutes (6.10 g, 100%.)

FAB-MS calc. for C$_{14}$H$_{20}$N$_2$O$_2$: 248; Found 249 (M+H)

Step C:

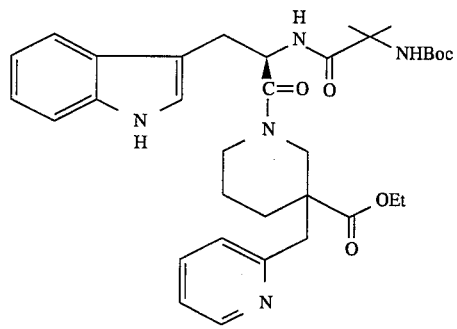

Prepared by the procedure described in Example 1, Step D from the compound prepared in the previous step (500 mg, 1.556 mmol), Intermediate 1 (1 eq.), HOBT (1 eq.), N-methyl morpholine (2 eq.), and EDC (597 mg, 3.11 mmol). Purification by MPLC eluting with ethyl acetate provided the title compound (883 mg, 91.5%).

FAB-MS calc. for C$_{34}$H$_{45}$N$_5$O$_6$: 619; Found 620 (M+H)

Step D:

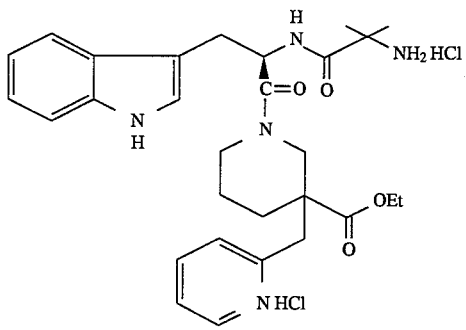

Prepared by the procedure described in Example 1, Step C from the intermediate from the previous step (250 mg, 0.404 mmol) in ethyl acetate (25 mL) and HCl gas at 0° C. for 25 minutes (204 mg, 85%)

FAB-MS calc. for C$_{29}$H$_{37}$N$_5$O$_4$: 519; Found 520 (M+H)

The additional intermediates shown in Table IV were prepared according to the above established procedure as exemplified in Example 7 step A and B. The final compounds were prepared according to Example 7 Steps C and D, using Intermediate 1.

TABLE IV

Intermediate: piperidine with NH, CO2Et, and Y substituent

Product: indole-tryptophan-amide-piperidine structure with CO2Et, Y, and NH2·HCl

| entry | Y | Intermediate MF FAB-MS (M + 1) | Product MF FAB-MS (M + 1) | isomer |
|---|---|---|---|---|
| 1 | 3-picolyl | C₁₄H₂₀N₂O₂ 249 | C29H37N5O4 520 | RS |
| 2 | 4-picolyl | C₁₄H₂₀N₂O₂ 249 | C29H37N5O4 520 | RS |
| 3 | 2-quinoline-methyl | C₁₈H₂₂N₂O₂ 298 | C33H39N5O4 569 | RS |
| 4 | benzimidazol-2-yl-CH₂— | C₁₆H₂₁N₃O₂ 288 | C31H38N6O4 559 | d1 d2 |
| 5 | 1-benzyl-imidazol-2-yl-CH₂— | C₁₉H₂₅N₃O₂ 328 | C34H42N6O4 599 | RS |
| 6 | 3-methyl-pyridin-2-yl-CH₂— | C₁₅H₂₂N₂O₂ 263 | C30H39N5O4 534 | RS |

The additional compounds shown in Table IVa were prepared according to Example 7 Steps C and D, using some of the intermediates shown in Table IV and Intermediate 3 instead of Intermediate 1.

TABLE IVa

ADDITIONAL EXAMPLES

Structure: Ph-(CH₂)₃-CH(NH-C(=O)-piperidine(CO2Et)(Y))-C(CH₃)₂-NH₂·HCl

| entry | Y | MF FAB-MS (M + 1) | isomer |
|---|---|---|---|
| 1 | 2-picolyl | C29H40N4O4 509 | d1 d2 |
| 2 | 3-picolyl | C29H40N4O4 509 | d1 d2 |
| 3 | 4-picolyl | C29H40N4O4 509 | d1 d2 |
| 4 | quinolin-2-yl-CH₂— | C33H42N4O4 559 | RS |
| 5 | benzimidazol-2-yl-CH₂— | C31H41N5O4 548 | d1 d2 |
| 6 | 3-methyl-pyridin-2-yl-CH₂— | C30H42N4O4 523, 545 (M + Na) | d1 d2 |

TABLE IVa-continued

EXAMPLE 8

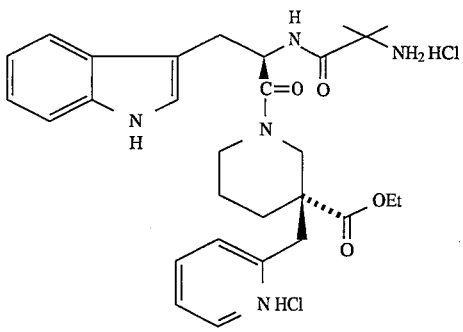

Step A:

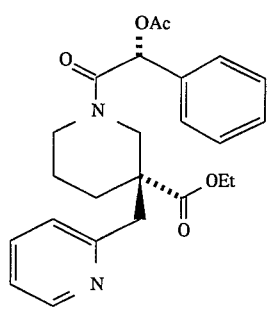

and

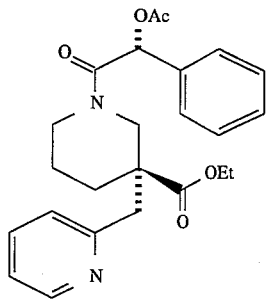

Prepared by the procedure described in Example 1, Step D from the intermediate (6 g, 18.67 mmol) prepared in Example 7, Step B, and using (R)-(–)-(O)-acetyl mandelic acid (1 eq.), HOBT (1 eq.), N-methyl morpholine (2 eq.), and EDC (7.16 g, 37.34 mmol). Purification by MPLC eluting with 80% ethyl acetate in hexane provided two enantiomerically pure compounds. The isomer which came out of the column first was designated as d1 (3.92 g, 99%) and the isomer which came out of the column second as d2 (3.69 g, 93%) FAB-MS calc. for $C_{24}H_{28}N_2O_5$ Found 425. The structure of intermediate $d_1$ was determined by x-ray crystallography. Given the absolute stereochemistry of (R) —O— acetylmandelic acid, the stereochemistry at the piperidine 3-position was assigned (S)— in $d_1$.

Step B:

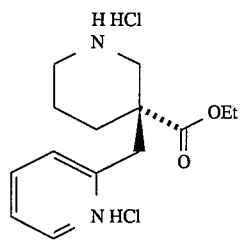

The intermediate d1 from the previous step (2.91 g, 6.86 mmol) in ethanol (30 mL) and concentrated HCl (25 mL) was refluxed for five hours. The reaction mixture was evaporated in vacuo and the residue was purified by silica gel flash column chromatography eluting with a solvent gradient of 1:10:90 to 2:20:80 ammonium hydroxide:methanol:chloroform to provide the compound (d1, 1.52 g, 70%). $^1$H NMR (CD$_3$OD, 400 MHz) δ8.84 (app. d,J=6 Hz, 1H), 8.60 (app. dt, J=1.5 Hz, 8 Hz, 1H), 8.04 (t, J=6 Hz, 1H), 7.94 (d, J=8 Hz, 1H), 4.34–4.27 (m, 1H), 4.23–4.17 (m, 1H), 3.75 (d, J=13 Hz, 1H), 3.46 (d, J=13.3 Hz, 1H), 3.40 (d, J=13.3 Hz, 1H), 3.31–3.29 (m, 2H), 3.20 (d, J=13 Hz, 1H), 3.03 (app dt, J=3.1 Hz, 12.8 Hz, 1H), 2.24 (br. d, 1H), 2.00–1.93 (m, 1H), 1.88 (dd, J=3.7 Hz, 13.5 Hz, 1H), 1.63–1.60 (m, 1H), 1.23 (t, 7.1 Hz, 3H). FAB-MS calc. for $C_{14}H_{20}N_2O_2$: 248; Found 249 (M+H)

Step C:

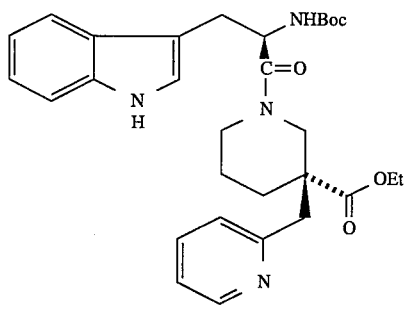

Prepared by the procedure described in Example 1, Step D from the intermediate prepared in Step B of this example (d1, 1.50 g, 4.67 mmol), N-t-Boc-D-Trp (1 eq.), HOBT (1 eq.), and EDC (1.53 g, 8.00 mmol). Purification by MPLC eluting with ethyl acetate provided the title compound (1.764 g, 71%). FAB-MS calc. for $C_{30}H_{38}N_4O_5$: 534; Found 535 (M+H)

Step D:

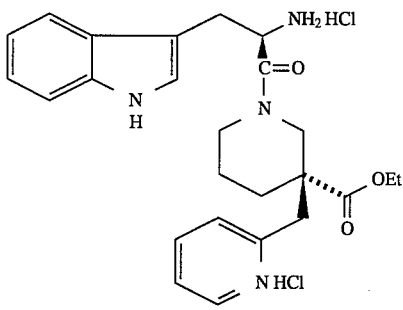

Prepared by the procedure described in Example 3, Step C from the intermediate from the previous step (1.658 g, 3.11 mmol) in ethyl acetate (50 mL) and HCl gas at 0° C. for 35 minutes (1.56 g, 99%).

FAB-MS calc. for $C_{25}H_{30}N_4O_3$: 434; Found 435 (M+H)

Step E:

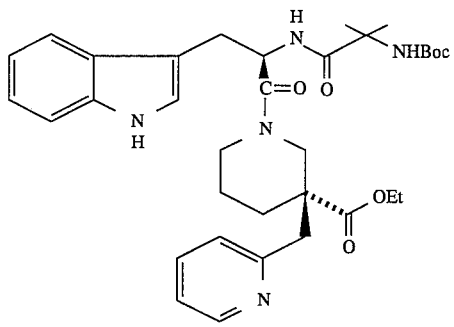

Prepared by the procedure described in Example 1, Step D from the intermediate prepared in Step D of this example (1.5 g, 2.96 mmol), N-t-Boc-α-methylalanine (1.1 eq.) DMAP (0.15 eq.), N-methyl morpholine (1 eq.), and EDC (1.135 g, 5.92 mmol). Purification by MPLC provided the title compound. (1.488 g, 81%)

FAB-MS calc. for $C_{34}H_{45}N_5O_6$: 619; Found 620 (M+H)

Step F:

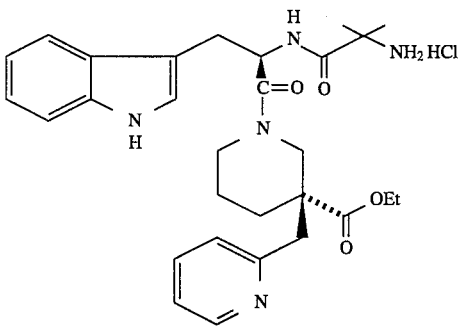

Prepared by the procedure described in Example 1, Step C from the intermediate from Step E (1.40 g, 2.26 mmol) in ethyl acetate (100 mL) and HCl gas at 0° C. for 1 hour (1.388 g, 100%).

1H NMR (CD$_3$OD, 400 MHz): 8.79–8.78 (M, 1H), 8.56–8.48 (M, 24), 8.0–7.96 (M, 1H), 7.72 (d, J=8.21 Hz, 1H) 7.53 (d, J=7.98, Hz, 1H) 7.25–7.22 (M, 2H) 6.89–6.86 (M, 1H) 5.48–5.43 (M, 1H) 3.89 (1, J=7.1 Hz, 2H) 2.30 (d, J=14.3 Hz, 1H) 1.85 (d, J=14.4 Hz, 1H) 1.01 (t, J=7.1 Hz, 3H) FAB-MS calc. for $C_{29}H_{37}N_5O_4$: 519; Found 520 (M+H)

EXAMPLE 9

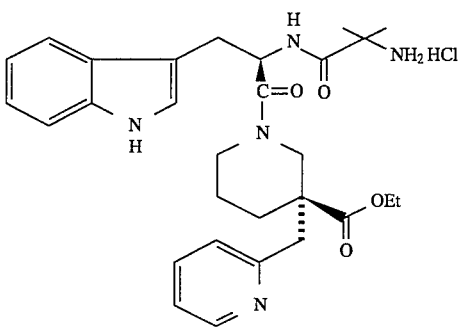

The title compound was similarly prepared from the intermediate d2 from Example 8, Step A. FAB-MS calc. for $C_{29}H_{37}N_5O_4$: 519; Found 520 (M+H)

EXAMPLE 10

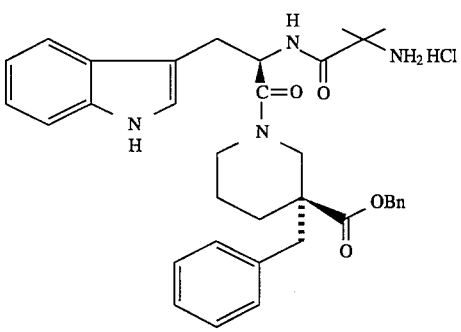

Step A:

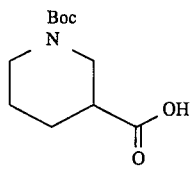

To a stirred solution of nipecotic acid (5 g, 38.7 mmol) in NaOH (2 eq.) in water was added di-tert-butyl dicarbonate (10 g, 46.44 mmol). The mixture was stirred at room temperature for 2 days. The mixture was then slowly acidified to pH=3 and stirred for two hours. The solution was extracted with ethyl acetate, dried, and concentrated to give white solid (6.25 g 70%).

Step B:

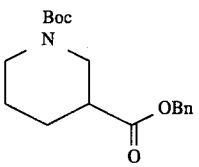

To a solution of the intermediate from the previous step (6.25 g, 27.3 mmol ), benzyl alcohol (3.4 mL, 32.7 mmol) and DMAP (33 mg, 0.273 mmol) in dichloromethane at 0° C., was added EDC (6.9 g, 35.4 mmol). The reaction mixture was stirred at room temperature for 7 hours. It was washed with a mixture of brine and 3N HCl, dried over anhydrous magnesium sulfate, filtered and concentrated. Purification by silica gel flash column eluting with a gradient of 10–30% ethyl acetate in hexane provided the benzyl ester (7.41 g, 85%).

Step C:

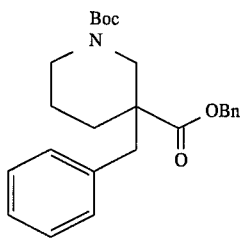

Prepared by the procedure described in Example 1, Step B from benzyl N-t-Boc-nipecotate (7.12 g, 22.2 mmol), LHMDS in THF (33.3 mL, 33.3 mmol) and benzyl bromide (4.0 g, 33.3 mmol). Purification by silica gel flash column chromatography eluting with 5–20% ethyl acetate in hexane provided the title compound. (9.10 g, 100%) $^1$H NMR (CDCl$_3$, 400 MHz) δ7.33–7.28(m, 3H), 7.23–7.17 (m, 5H), 7.01–6.98 (m, 2H), 5.00 (br. ABq, JAB=12 Hz, 2H), 4.00 (br.s, 1H), 3.55–3.50 (m, 1H), 3.18 (d, J=13 Hz) 3.14 (v.br.s, 1H), 2.92 (d, J=13.5 Hz), 2.74 (d, J=13.4 Hz), 2.03–1.99 (m, 1H), 1.63–1.50 (m, 3H), 1.39 (s, 9H).

Step D:

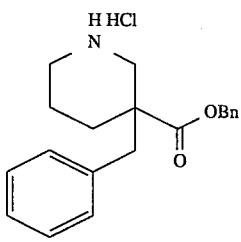

Prepared by the procedure described in Example 1, Step C from the intermediate from the previous step (3.08 g, 7.52 mmol) in ethyl acetate (40 mL) and HCl gas at 0° C. for 15 minutes (2.65 g, 100%).

FAB-MS calc. for C$_{20}$H$_{23}$NO$_2$: 309; Found 310 (M+H)

Step E:

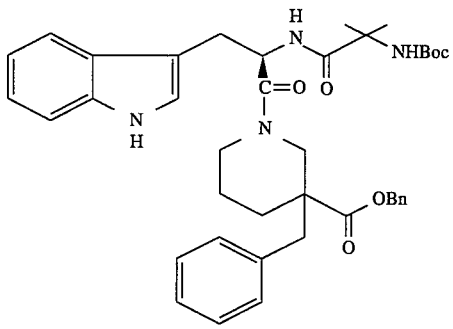

Prepared by the procedure described in Example 1, Step D from the intermediate prepared in the previous step (768 mg, 2.22 mmol), Intermediate 1 (720 mg, 1.85 mmol), HOBT (1 eq.), N-methyl morpholine (1 eq.), and EDC (2 eq.). Purification by MPLC, eluting with 50% ethyl acetate in hexane, provided two diasteromers. The isomer which came out first was designated as d1 (504 mg, 40%) and the one which eluted second was designated as d2 (474 mg, 38%)

d1 FAB-MS calc. for C$_{40}$H$_{48}$N$_4$O$_6$: 680; Found 681 (M+H)

d2 FAB-MS calc. for C$_{40}$H$_{48}$N$_4$O$_6$: 680 Found 681 (M+H)

Step F:

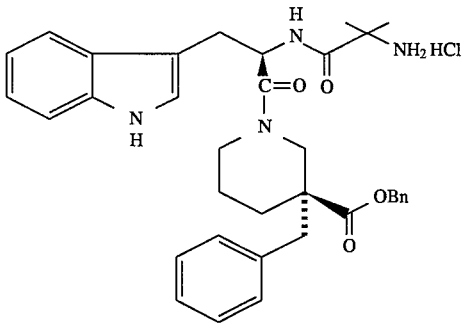

Prepared by the procedure described in Example 1, Step C from the intermediated d1 from Step E (25 mg, 0.036 mmol) in ethyl acetate (3 mL) and HCl gas at 0° C. for 10 minutes (20.2 mg, 91%).

FAB-MS calc. for C$_{35}$H$_{40}$N$_4$O$_4$: 580; Found 581 (M+H)

EXAMPLE 11

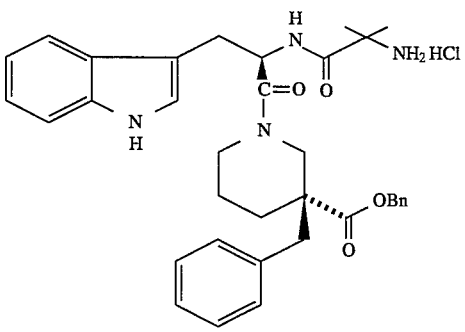

Prepared by the procedure described in Example 1, Step C from the intermediate d2 (20.1 mg, 0.03 mmol) of Example 10, Step E in ethyl acetate (3 mL) and HCl gas at 0° C. for 10 minutes (12.8 mg, 70%).

FAB-MS calc. for C$_{35}$H$_{40}$N$_4$O$_4$: 580; Found 581 (M+H)

EXAMPLE 12

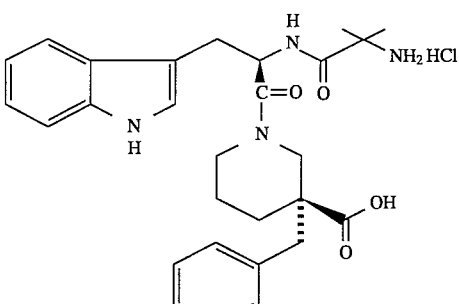

Step A:

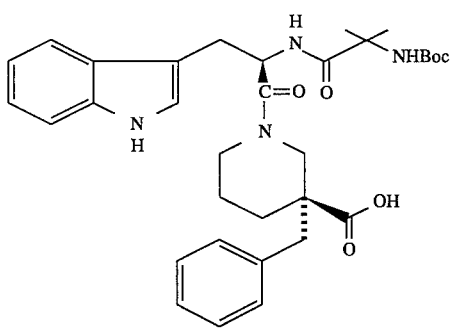

A suspension of 10% palladium on carbon (60 mg) and the intermediate (d1) from Example 10, Step E (442.6 mg, 0.65 mmol) in ethanol (20 mL) was vigorously stirred under a hydrogen atmosphere for 30 minutes. The reaction mixture was then filtered through celite and evaporated to give the product (376.0 mg, 98%).

d1 FAB-MS calc. for $C_{33}H_{42}N_4O_6$: 590; Found 591 (M+H)

Step B:

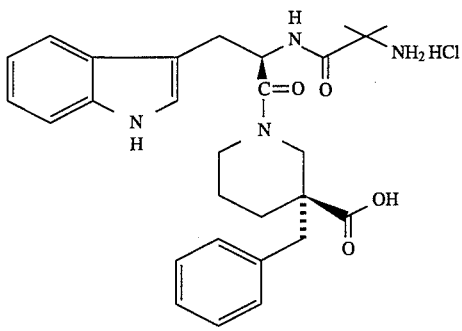

Prepared by the procedure described in Example 1, Step C from the intermediate from the previous step (211 mg, 0.357 mmol) and HCl gas in ethyl acetate (15 mL) at 0° C. for 10 minutes (175.6 mg, 93%).

$^1$H NMR (CD$_3$OD, 400 MHz): The compound exists in two rotamers in approximately a 1:1 ratio. δ7.57–7.54 (m, 1H), 7.38 (d, J=8.2 Hz, 1/2H), 7.33 (d, J=8.2 Hz, 1/2H), 7.25–7.00 (m, 8H), 6.81–6.79 (m, 1H), 5.36 (dd, J=6 Hz, 8.5 Hz, 1/2H), 5.18 (app t, J=7.5 Hz, 1/2H), 4.32 (br. d, J=13 Hz, 1/2H), 4.00 (br. d, J=13 Hz, 1/2H), 3.78 (br. d, J=13 Hz, 1/2H), 3.26–3.02 (m, 11/2H), 2.86 (d, J=13.4 Hz, 1/2H), 2.80 (d, J=13.4 Hz, 1/2H), 2.53 (d, J=13.4 Hz, 1/2H), 2.46 (d, J=13.4 Hz, 1/2H), 2.29 (dt, 1/2H), 2.09 (d, J=12.7 Hz, 1/2H), 1.92–1.88 (m, 1/2H), 1.55, 1.50, 1.44 (3s, 6H), 1.40–1.25 (m, 1H), 1.20–1.12 (m, 1/2H).

d1 FAB-MS calc. for $C_{28}H_{34}N_4O_4$: 490; Found 491 (M+H)

EXAMPLE 13

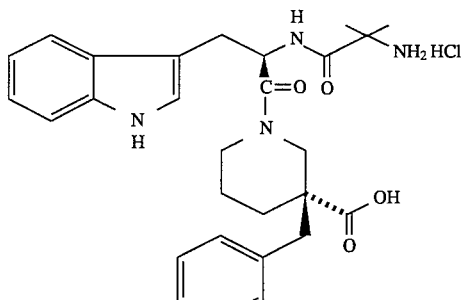

Step A:

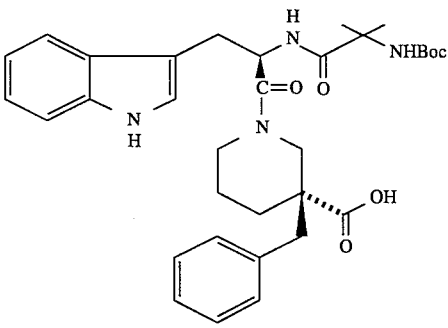

Prepared similarly from the intermediate d2 (224.2 mg, 0.33 mmol) from Example 10, Step E (169.3 mg, 87%).

d2 FAB-MS calc. for $C_{33}H_{42}N_4O_6$: 590; Found 591 (M+H)

Step B:

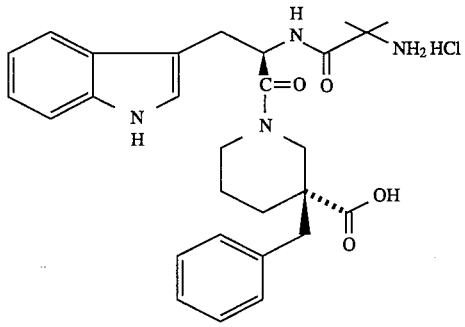

Prepared by the procedure described in Example 1, Step C from the intermediate from the previous step (139 mg, 0.235 mmol) and HCl gas in ethyl acetate (15 mL) at 0° C. for 10 minutes (122.7 mg, 99%). $^1$H NMR (CD$_3$OD, 400 MHz): The compound exists as two rotamers in approximately a 1:1 ratio. δ8.21 (d, J=7.4 Hz, 1/2H), 7.91 (d, J=7.4 Hz, 1/2H), 7.62 (d, J=7.9 Hz, 1/2H), 7.50 (d, J=7.9 Hz, 1/2H), 7.34–6.90 (m, 9H), 5.40–5.34 (m, 1H), 4.40 (d, J=13.7 Hz, 1/2H), 4.13 (d, J=12.6 Hz, 1/2H), 3.63 (d, J=13.3 Hz, 1/2H), 3.50 (d, J=13.3 Hz, 1/2H), 3.30–3.10 (m, 7/2H), 2.93 (ABq, 1H), 2.88 (v. br. d, 1/2H), 2.60 (d, J=13 Hz, 1/2H), 2.40 (d, J=13 Hz, 1/2H), 2.19–2.16 (m, 1/2H), 1.78–1.75 (m, 1H), 1.60–1.40 (m, 3/2H), 1.20–1.10 (m, 1/2H), 1.58, 1.50, 1.47, 1.15 (4s, 6H), 1.00–0.90 (m, 1/2H).

d2 FAB-MS calc. for $C_{28}H_{34}N_4O_4$: 490; Found 491 (M+H)

The additional examples shown in Table V were prepared according to Examples 10 through 12 using Intermediate 3 and the intermediate obtained in Example 10 Step D.

TABLE V

ADDITIONAL EXAMPLES

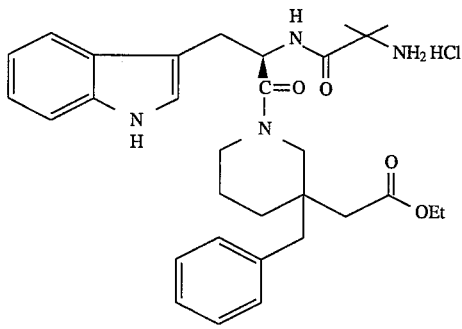

| entry | X | MF<br>FAB-MS (M + 1) | isomer |
|---|---|---|---|
| 1 | CO2Bn | C35H43N3O4<br>570 | RS |
| 2 | CO2H | C28H37N3O4<br>480 | RS |

EXAMPLE 14

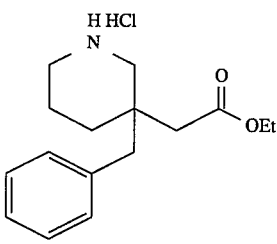

Step A:

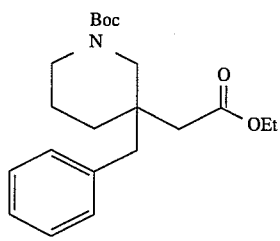

A solution of n-BuLi in hexane (4.9 mL, 12.36 mmol) was added to a stirred solution of 2,2,6,6-tetramethylpiperidine (TMP, 2.3 mL, 1.92 g, 13.5 mmol) in THF (25 mL) with ice-bath cooling. In a separate flask, a stirred mixture of ethyl N-t-Boc-3-benzyl-nipecotate (Example 1, Step B, 1.73 g 5 mmol) and $CH_2Br_2$ (0.78 mL, 2.15 g, 12.4 mmol) in THF (20 mL) was cooled to −78° C., and the Lithium salt solution of TMP solution just prepared was then added over a 15 minute period at a temperature below −65° C. After 10 minute, a solution of LHMDS (11.2 mL, 11.2 mmol) was added over a 10 minutes period at −78° C. Following the addition, the cooling bath was removed and the mixture was allowed to warm gradually to 0° C. The mixture was cooled with an ice bath, and a solution of n-BuLi in hexane (13.5 mL, 33.7 mmol) was added at a temperature below 5° C. over a 15 minutes period. The mixture was warmed to room temperature and stirred for 45 minutes. The mixture was cooled to −78° C. and quenched over a 50 minute period by adding it into a stirred solution of acidic ethanol (30 mL) at 0° C. The mixture was evaporated to dryness and suspension in dichloromethane (100 mL), to which was added triethylamine ( 0.7 mL, 5.0 mmol) and di-tert-butyl dicarbonate (1.09 g, 5.0 mmol) while stirring at room temperature, the material was washed with brine, dried, and concentrated. Purification by silica gel flash column chromatography, eluting with 10–30% ethyl acetate in hexane, provided the compound (1.44 g, 80%).

Step B:

Prepared by the procedure described in Example 1, Step C, from the intermediate from the previous step (1.30 g, 3.56 mmol) and HCl gas in ethyl acetate (50 mL) at 0° C. for 45 minutes (975 mg, 91%).

FAB-MS calc. for $C_{16}H_{23}NO_2$: 261; Found 262 (M+H)

Step C:

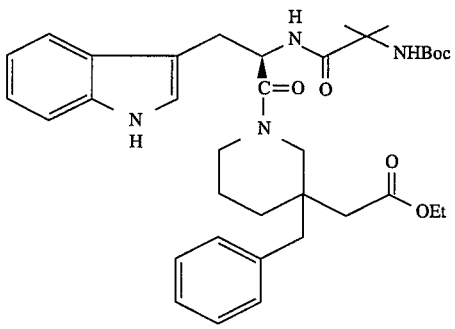

Prepared by the procedure described in Example 1, Step D from the intermediate prepared in the previous step (55 mg, 0.21 mmol), Intermediate 1 (1 eq.), HOBT (1 eq.), N-methyl morpholine (1 eq.), and EDC (80 mg, 0.42 mmol). Purification by MPLC eluting with 60% ethyl acetate in hexane provided the compound (77 mg, 61.5%).

Step E:

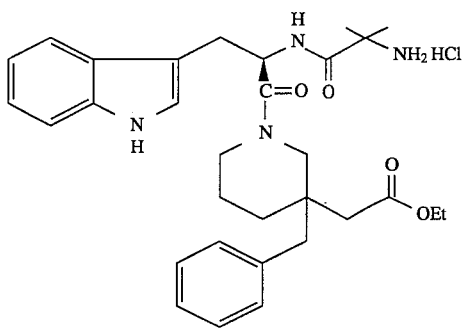

Prepared by the procedure described in Example 1, Step C from the intermediate from the previous step (77 mg, 0.13 mmol) and HCl gas in ethyl acetate (8 mL at 0° C. for 15 minutes (59 mg, 85%).

FAB-MS calc. for $C_{31}H_{40}N_4O_4$: 532; Found 533 (M+H)

EXAMPLE 15

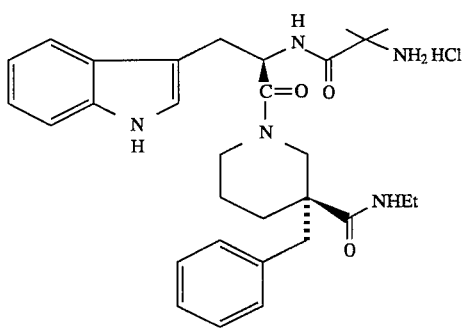

Step A:

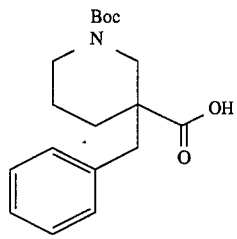

The intermediate from Example 10, Step C (1.85 g, 4.52 mmol) was hydrogenated over 1 atm of H2 and 10% palladium on carbon (150 mg) in ethanol (20 mL). Filtering through celite and evaporation yielded the acid (1.36 g. 94%). 1H NMR (CDCl$_3$, 400 MHz) δ7.27–7.19 (m, 3H), 7.14–7.10 (m, 2H), 4.08–3.59 (br. m, 1H), 3.63–3.59 (m, 1H), 3.15–3.05 (br. m, 2H), 4.08–3.59 (br. m, 1H), 3.63–3.59 (m, 1H), 3.15–3.05 (br. m, 2H), 2.9. (d, J=13.5 Hz, 1H), 2.79 (d, J=13.5 Hz, 1H), 2.05–1.95 (br. m, 1H), 1.70–1.45 (m, 3H), 1.42 (s, 9H). EI-MS calc. for $C_{18}H_{25}NO_4$: 319; Found 319 (M+,)

Step B:

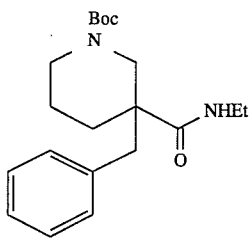

To a solution of the intermediate from the previous step (320.4 mg, 1.0 mmol) in dichloromethane containing ethyl amine hydrochloride (163 mg, 2.0 mmol), DMAP (1.0 eq.), and N-methyl morpholine (2 eq.), was added EDC (2 eq.). The reaction mixture was stirred at room temperature overnight. The solution was washed with 3N HCl and brine, dried over anhydrous magnesium sulfate, then filtered and concentrated. Purification by silica gel flash column eluting with a gradient of 60–100% ethyl acetate in hexane provided the title compound (262 mg, 76%). 1H NMR (CDCl$_3$, 400 MHz) δ7.21–7.13 (m, 3H), 7.03 (d, 2H), 6.68 (br. s, 1H), 4.18 (br. d, 1H), 3.96 (br. d, 1H), 3.12–3.00 (m, 4H), 2.70–2.40 (br. m, 5H), 1.60–1.50 (m, 1H), 1.37 (s, 9H), 1.20–1.30 (m, 1H), 0.90 (q, J=7.3 Hz, 3H). EI-MS calc. for $C_{20}H_{30}N_2O_3$: 346; Found 346 (M+)

Step C:

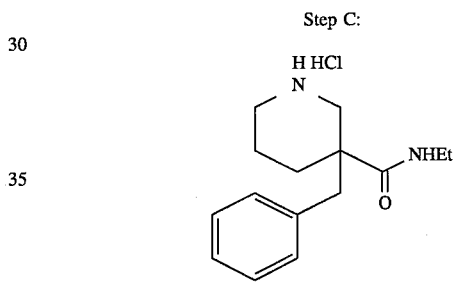

Prepared by the procedure described in Example 1, Step C from the intermediate from the previous step (262 mg, 0.76 mmol) and HCl gas in ethyl acetate (5 mL) at 0° C. for 1 hour (194 mg, 90%). $^1$H NMR (CD$_3$OD, 400 MHz) δ8.28 (br. s, 1H), 7.30–7.24 (m, 3H), 7.14–7.12 (m, 2H), 3.43 (d, J=12 Hz, 1H), 3.34–3.28 (m, 2H), 3.26–3.20 (br. d, 1H), 3.11 (d, J=14 Hz, 1H), 2.88 (dt, J=3.2 Hz, 13 Hz, 1H), 2.81 (d, J=12.5 Hz, 1H), 2.77 (d, J=14 Hz, 1H), 2.24 (d, J=13 Hz, 1H), 1.87 (td, J=2.8 Hz, 14 Hz, 1H), 1.75 (dt, J=3.3 Hz, 13.5 Hz, 1H), 1.64–1.55 (m, 1H), 1.17 (t, J=7 Hz, 3H).

Step D:

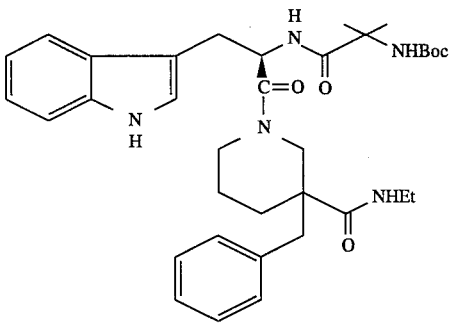

Prepared by the procedure described in Example 1, Step D from intermediate prepared in the previous step (62.2 mg, 0.22 mmol), Intermediate 1 (1 eq.), HOBT (1 eq.), N-methyl morpholine (1 eq.), and EDC (2 eq.). Purification by MPLC eluting with ethyl acetate provided two diastereomers, the one which was eluted out of the column first was designated as d1 (35.8 mg, 26%) and the one came out second was designated as d2 (43.8 mg, 31%).

d2. $^1$H NMR (CD3OD, 400 MHz): The compound exists in two rotamers in approximately a 1:1 ratio. δ8.16 (br. s, 1/2H), 7.53 (d,J=8.7 Hz, 1H), 7.32 (d,J=8.1 Hz, 1H), 7.25–6.96 (m, 8H), 6.69 (br. s, 1/2H), 5.28–5.12 (m, 1/2H), 4.94 (v. br. m, 1/2H), 4.31 (br. d,J=14.6 Hz, 1/2H), 3.49 (v. br. d, J=13 Hz, 1/2H), 3.22 (dd,J=4.7 Hz, 14.3 Hz, 1/2H), 3.03–2.97 (m, 2H), 2.90 (d,J=13.4 Hz, 1/2H), 2.40 (br. d, 1/2H), 2.36 (d,J=13.3 Hz, 1/2H), 2.10 (d,J=13.5 Hz, 1/2H), 1.92–1.82 (br. m, 3/2H), 1.47 (s, 3H), 1.41 (s, 9 H), 1.38 (s, 3H), 1.32–1.20 (m), 1.10–1.00 (dt, 1/2H), 0.85 (t,J=7.2 Hz, 3H).

d1 FAB-MS calc. for $C_{35}H_{47}N_5O_5$: 617; Found 618 M+H)

d2 FAB-MS calc. for $C_{35}H_{47}N_5O_5$: 618; Found 618 (M+H)

Step E:

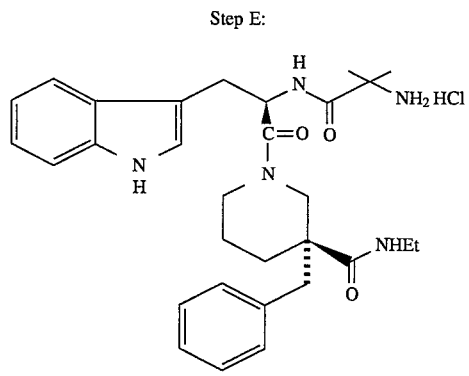

Prepared by the procedure described in Example 1, Step C from the Intermediate d1 from the previous step (35 mg, 0.057 mmol) and HCl gas in ethyl acetate (3 mL) at 0° C. for 30 minutes (32.5 mg, 100%). FAB-MS calc. for $C_{30}H_{39}N_5O_3$: 517; Found 518 (M+H)

EXAMPLE 16

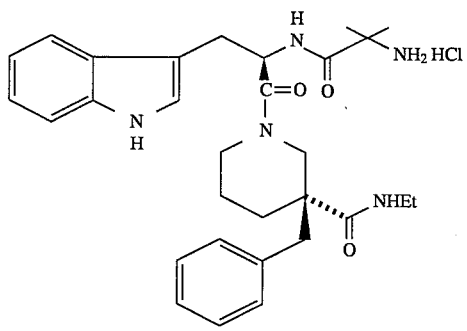

Prepared by the procedure described in Example 1, Step C from the intermediate d2 from Example 15, Step D (41 mg, 0.066 mmol) and HCL gas in ethyl acetate (3 mL) at 0° C. for 30 minutes (36.5 mg, 100%). $^1$H NMR (CD3OD, 400 MHz): The compound exists in two rotamers in approximately a 4:1 ratio. δ8.21 (d,J=7.4 Hz, 4/5H), 8.02 (d,J=7.4 Hz, 1/5H), 7.68 (d,J=7.8 Hz, 4/5H), 7.35 (d,J=7.1 Hz, 4/5H), 7.31 (d,J=7.1 Hz, 1/5H), 7.26–6.98 (m, 8H), 5.46–5.40 (m, 1/5H), 5.25–5.20 (m, 4/5H), 4.00 (br. d, 4/5H), 3.85 (br. d, 1/5H), 3.65 (br. d,J=13.2 Hz, 4/5H), 3.60–3.54 (m, 1/5H), 3.36 (br. d, 1/5H), 3.30–3.03 (m), 2.82–2.62 (m), 2.46 (d,J=13.3 Hz, 8/5H), 2.08 (br. d, 4/5H), 1.09–1.84 (m, 1/5H), 1.76–1.65 (m), 1.51, 1.49 (2s, 6H), 1.40–1.20 (m), 100 (t,J=7.2 Hz, 3/5H), 0.88 (t,J=7.2 Hz, 12/5H). FAB-MS calc. for $C_{30}H_{39}N_5O_3$: 517; Found 518 (M+H)

EXAMPLE 17

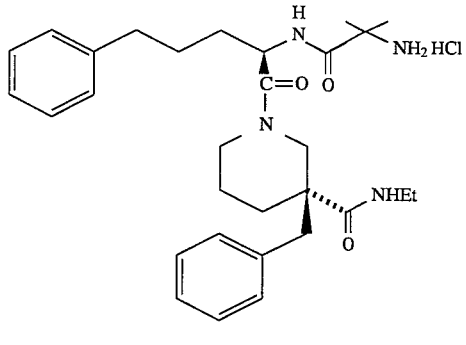

Step A

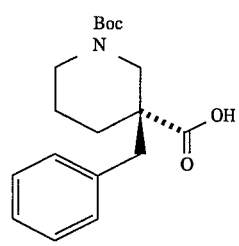

To a suspension of the S-isomer intermediate of Step A of Example 2 (27.3 g, 68.8mmol) in 3 N sodium hydroxide (25 mL), dichloromethane (200 mL) and water (100 mL), was slowly added di-t-butyl dicarbonate (18 g, 1.2 equiv.). The mixture was stirred for an additional 5 hours after the addition, it was acidified to PH 3 carefully and then extracted with ethyl acetate three times. The organic extracts were combined, dried, and concentrated to give a white solid (23.7 g). A solution of this intermediate (11.5 g, 33.1 mmol) and 3 N NaOH (30 mL) in ethanol (200 mL) and water (10 mL) was refluxed for one day. The solution was evaporated to remove ethanol, and then acidified with 3 N HCL to pH=3 and extracted with ethyl acetate. The extract was dried, evaporated and purified by a short silica gel column, initially eluting with 20% ethyl acetate in hexane, then with ethyl acetate to give the product (8.76 g, 83%). NMR and MS were identical to Example 15 step A.

Step B

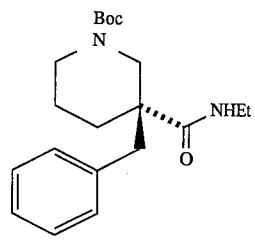

To a mixture of the intermediate from the previous step (660 mg, 2.07 mmol), ethylamine hydrochloride (251 mg, 1.5 equiv.), NMM (0.23 mL, 1 equiv.) and HOBT (1 eq) in dichloromethane and DMF (1:1, 10 mL) was added EDC. The mixture was stirred at room temperature for two days, heated at reflux for 2 hours, and was poured into a dilute HCL and brine mixture. It was extracted with ethyl acetate, and the organic layer was washed with dilute NaOH, dried and evaporated. Purification by flash column eluting with 20–80% ethyl acetate in hexane gave the product (540 mg, 75%). NMR and MS were identical to Example 15 Step B.

Step C

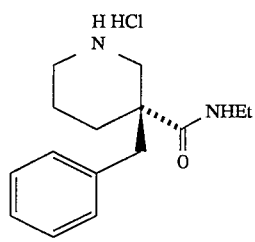

Prepared by the procedure described in Example 1, Step C from the intermediate from the previous step (0.33 g, 0.95 mmol) in ethyl acetate (5 mL) and HCl gas at 0° C. for 15 minutes 0.279 mg, 100%). FAB-MS calc. for $C_{15}H_{22}N_2O$: 246; Found 247 (M+H)

Step D

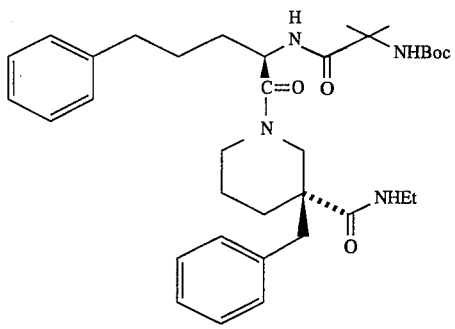

Prepared from the procedure described in the Example 1Step D from the intermediate prepared in the previous step (100 mg, 0.354 mmol), Intermediate 3 (134 mg, 0.354 mmol), HOBT (48 mg, 1 eq.), N-methyl morpholine (0.039 mL, 1 eq.), and EDC (102 mg, 1.5 eq.). Purification by MPLC, eluting with ethyl acetate, provided the intermediate (140 mg, 65%). FAB-MS calc. for $C_{35}H_{50}N_4O_5$: 606; Found 607 (M+H)

Step E

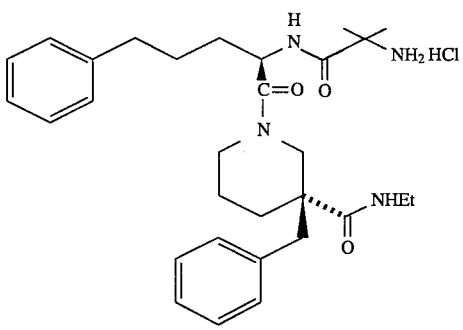

Prepared by the procedure described in Example 1, Step C from the intermediate from the previous step (132 mg, 0.217 mmol) and HCL gas in ethyl acetate (5 mL) at 0° C. for 10 minutes (113.3 mg, 96%).

d1 FAB-MS calc. for $C_{30}H_{42}N_4O_3$ 506, (M+H)

The additional intermediates shown in Table VIa were prepared according to the above established procedure as exemplified in Example 15, and Example 17 steps A through C,. The final compounds were prepared according to Example 17 Steps D and E, using Intermediate 1.

TABLE VIa

ADDITIONAL EXAMPLES

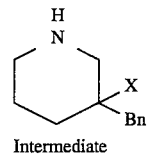

Intermediate

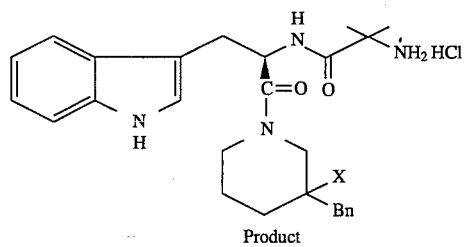

Product

| entry | X | Intermediate MF FAB-MS (M + 1) | Product MF FAB-MS (M + 1) | isomer |
|---|---|---|---|---|
| 1 | —CO(morpholino) | $C_{17}H_{24}N_2O_2$ 288 (M+,EI) | $C_{32}H_{41}N_5O_4$ 560 | S |
| 2 | —CONHCH$_3$ | $C_{14}H_{20}N_2O$ 233 | $C_{29}H_{37}N_5O_3$ 504 | S |
| 3 | —CONH— | $C_{17}H_{24}N_2O_3$ | $C_{32}H_{41}N_5O_5$ | S |

TABLE VIa-continued
ADDITIONAL EXAMPLES

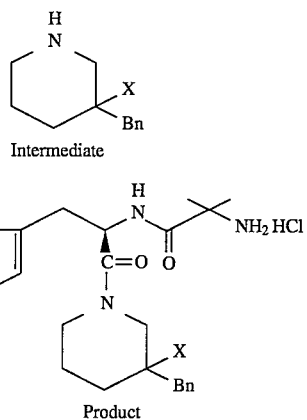

Intermediate

Product

| entry | X | Intermediate MF FAB-MS (M + 1) | Product MF FAB-MS (M + 1) | isomer |
|---|---|---|---|---|
|   | $CH_2CO_2Et$ | 304 (M+,EI) | 576 |   |
| 4 | $-CO_2CH_2CO_2Et$ | $C_{17}H_{23}NO_4$ | $C_{32}H_{40}N_4O_6$ | R |
|   |   | 306 | 577 | S |
| 5 | $-CO_2(CH_2)_2SMe$ | $C_{16}H_{23}NO_2S$ | $C_{31}H_{40}N_4O_4S$ | R |
|   |   | 294 | 565 | S |
| 6 | $-CON(CH3)2$ | C15H22N2O | C30H39N5O3 | d1 |
|   |   | 247 | 518 | d2 |
| 7 | $-CONH-$ | $C_{15}H_{22}N_2O_2$ | $C_{30}H_{39}N_5O_4$ | S |
|   | $(CH_2)_2OH$ | 263 | 534 |   |

Likewise using 3-aminopropanol or 2-(ethylthio)ethylamine it is possible to prepare the compounds shown in Table VIb using Intermediate 1.

TABLE VIb

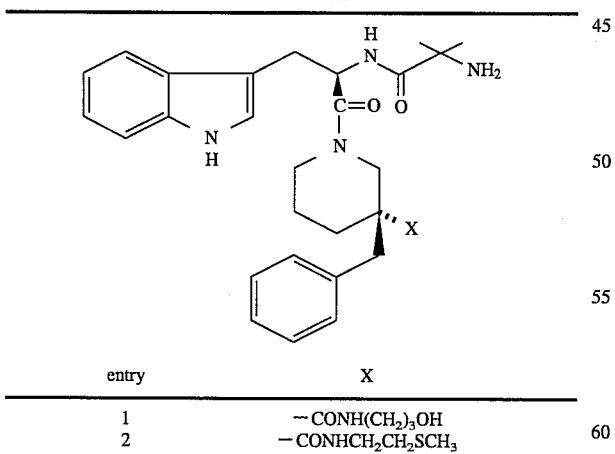

| entry | X |
|---|---|
| 1 | $-CONH(CH_2)_3OH$ |
| 2 | $-CONHCH_2CH_2SCH_3$ |

The additional compounds shown in Table VIc were prepared according to Example b 17Steps C and D, using some of the intermediates shown in Table VIa and Intermediate 3.

TABLE VIc
ADDITIONAL EXAMPLES

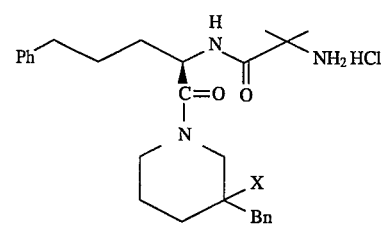

| entry | Y | MF FAB-MS (M + 1) | isomer |
|---|---|---|---|
| 1 | $-CO$(morpholino) | $C_{32}H_{44}N_4O_4$ 549 | S |
| 2 | $-CONHCH_3$ | $C_{29}H_{40}N_4O_3$ 493 | S |
| 3 | $-CONH-$ $CH_2CO_2Et$ | $C_{32}H_{44}N_4O_5$ 565 | S |
| 4 | $-CONH-$ $(CH_2)_2OH$ | $C_{30}H_{42}N_4O_4$ 523 | S |

Likewise using 3-aminopropanol and 2-(methylthio)-ethylamine it is possible to prepare the compounds shown in Table VId.

TABLE VId

[Structure shown]

| entry | X |
|---|---|
| 1 | —CONH(CH$_2$)$_3$OH |
| 2 | —CONHCH$_2$CH$_2$SCH$_3$ |

The additional compounds shown in Table VIe were prepared according to Example 17 Steps C and D, using some of the intermediates shown in Table VI and Intermediate 2.

TABLE VIe

ADDITIONAL EXAMPLES

[Structure shown]

| entry | Y | MF FAB-MS (M + 1) | isomer |
|---|---|---|---|
| 1 | —CO(morpholino) | C$_{31}$H$_{42}$N$_4$O$_5$ 551 | S |
| 2 | —CONHCH$_3$ | C$_{28}$H$_{38}$N$_4$O$_4$ 495 | S |
| 3 | —CONH—CH$_2$CO$_2$Et | C$_{31}$H$_{42}$N$_4$O$_6$ 567 | S |

EXAMPLE 18

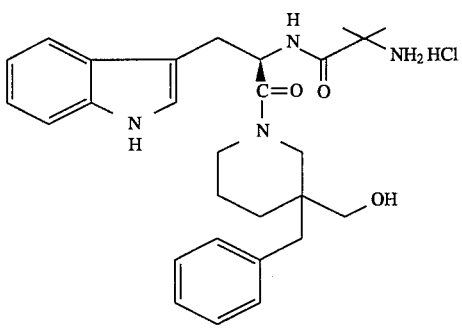

TABLE VIe-continued

Step A:

[Structure shown]

To a stirred solution of ethyl N-t-Boc-3-phenylmethyl nipecotate (10.4 g, 29.93 mmol) in dichloromethane (100 mL) at −78° C. was added DIBAL (1M, 45 mL). The reaction was stirred at −78° C. for 4 hours and quenched by the addition of methanol (5 mL). The reaction mixture was washed carefully with tartaric acid water solution and brine, dried over MgSO$_4$ and evaporated. Silica gel flash chromatography eluting with a gradient of 40–80% ethyl acetate in hexane yielded the product (6.81 g, 75%).

EI-MS calc. for C$_{18}$H$_{27}$NO$_3$: 305; Found 305 (M+)

Step B: 3-Phenylmethyl-3-piperidinemethanol hydrochloride

[Structure shown]

A solution of the intermediate from the previous step (770 mg, 2.52 mmol) in ethanol (20 mL) and concentrated HCl (1 mL) was refluxed for 3 hours. The reaction mixture was cooled to room temperature and evaporated to give the title compound as a white solid. (609.0 mg, 100%)

$^1$H NMR (CD$_3$OD, 400 MHz) δ7.31–7.19 (m, 5H), 3.45 (ABq, J=11 Hz, 2H), 3.18 (d, J=13 Hz, 1H), 3.19–3.13 (m, 1H), 3.03–2.99 (m, 1H), 2.96 (d, J=13 Hz, 1H), 2.72 (s, 1H), 1.92–1.84 (m, 2H), 1.60–1.50 (m, 2H).

EI-MS calc. for C$_{12}$H$_{17}$NO: 191; Found 191 (M+,)

Step C:

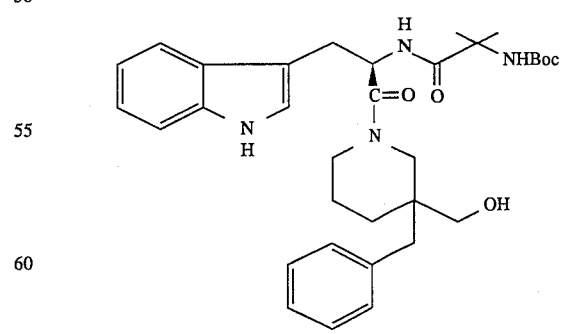

Prepared by the procedure described in Example 1, Step D from the intermediate prepared in the previous step (142 mg, 0.587 mmol), Intermediate 1 (0.8 eq.), HOBT (1 eq.), N-methyl morpholine (1 eq.), and EDC (2 eq.). Purification by MPLC eluting with ethyl acetate gave two compounds; the compound which came out of the column first is designated as d1 (98.5 mg, 58%) and the compound which came out of the column next as d2 (34.5 mg, 12%)

d1 FAB-MS calc. for $C_{32}H_{42}N_4O_5$: 562; Found 563 (M+H)

d2 FAB-MS calc. for $C_{32}H_{42}N_4O_5$: 562; Found 563 (M+H)

Step D:

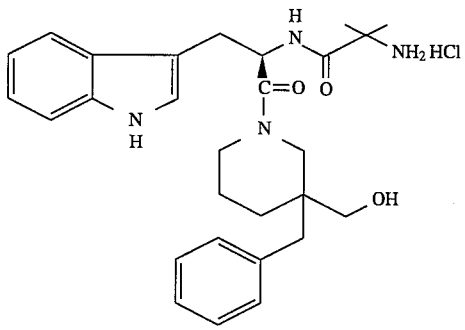

The intermediate (d1) from the previous step (60 mg, 0.104 mmol) was treated with HCl gas at 0° C. in ethyl acetate (3 mL) for five minutes. Evaporation gave the diastereomer 1 of the title compound.

d1 FAB-MS calc. for $C_{28}H_{36}N_4O_3$: 476; Found 477 (M+H)

The intermediate (d2) from Step C (20 mg) was treated with HCl gas at 0° C. in ethyl acetate (3 mL) for five minutes. Evaporation gave the diastereomer 2 of the title compound.

d2 FAB-MS calc. for $C_{28}H_{36}N_4O_3$: 476; Found 477 (M+H)

EXAMPLE 19

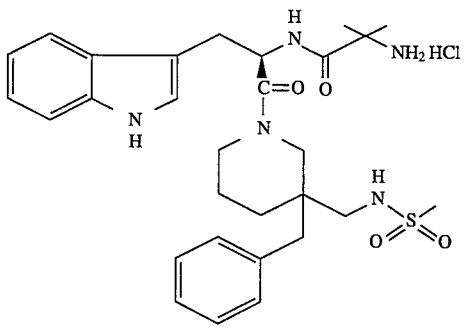

Step A:

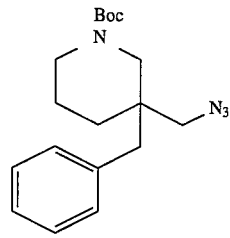

To a stirred solution of intermediate from Example 18, Step A (5.12 g, 16.8 mmol), and triethylamine (4.7 mL) in dichloromethane at 0° C. was added mesyl chloride (1.95 mL). The reaction mixture was stirred for 2 hours. The solution was poured into a mixture of brine and 3N HCl and extracted with ethyl acetate. The organic layer was washed with saturated sodium bicarbonate, dried over magnesium sulfate and evaporated to yield the mesylate. The mesylate was heated with sodium azide (2.2 g, 33.6 mmol) in DMSO (20 mL) at 80° C. for two weeks. The mixture was poured into ice water and extracted with ethyl acetate. The organic layer was washed with saturated sodium bicarbonate and brine; it was dried, and evaporated. Purification by silica gel flash column chromatography provided the azide (4.14 g, 75%).

$^1$H NMR (CDCl$_3$, 200 MHz) δ7.29 –7.13 (m, 5H), 3.61–3.57 (br. m, 1H), 3.47 (d, J=12 Hz, 1 H), 3.20–3.10 (v. br. s, 2H), 3.10–2.96 (v. br. d, 1H), 2.60–2.45 (br. m, 2H), 1.65–1.48 (m, 4H), 1.44 (s, 9H), 1.41–1.35 (m, 1H).

FAB-MS calc. for $C_{18}H_{26}N_4O_2$: 330; Found 331 (M+H)

Step C:

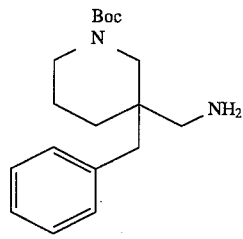

The azide from the previous step (1.60 g, 4.84 mmol) was hydrogenated over 10% palladium on carbon (160 mg) in ethanol (25 mL) under a 1 atm hydrogen balloon for 2 hours. The reaction mixture was filtered through celite and evaporated to give the amine (1.42 g, 96). FAB-MS calc. for $C_{18}H_{28}N_2O_2$: 304; Found 305 (M+H)

Step D:

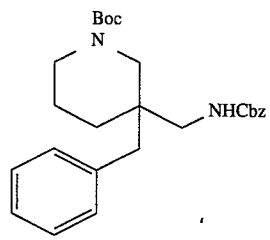

To a stirred solution of the amine from the previous step (1.30 g, 4.27 mmol) in dichloromethane (20 mL) which also contained DMAP (20 mg) and triethylamine (1 mL) at 0° C., was added CbzCl (0.73 mL, 5.12 mmol). The reaction mixture was stirred for 2 hours. The solution was poured into a mixture of brine and 3 N HCl and extracted with ethyl acetate. The organic layer was washed with saturated sodium bicarbonate, dried over magnesium sulfate and evaporated to give a residue which was purified by flash chromatography, eluting with 20% ethyl acetate in hexane, to yield the product (1.52 g).

FAB-MS calc. for $C_{26}H_{34}N_2O_4$: 438; Found 439 (M+H)

Step E:

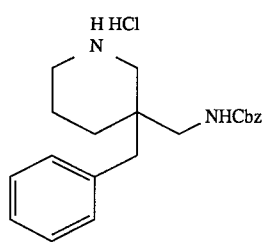

To a stirred solution of the intermediate from the previous step (1.50 g, 3.42 mmol) in ethyl acetate (50 mL) at 0° C. was bubbled HCl until it was saturated. The reaction mixture was stirred for one hour and evaporated to yield the salt (1.32 g, 100%).

$^1$H NMR (CD$_3$OD, 400 MHz) δ7.40–7.18 (m, 10H), 5.14 (s, 2H), 3.43, 3.42 (2 d, J=14.8 Hz, 1H), 3.23 (td, J=4 Hz, 12.1 Hz, 1H), 3.00 (d, J=13 Hz, 1H), 2.94 (d, J=14.7 Hz, 1H), 2.83 (dt, J=3.4 Hz, 12 Hz, 1H), 2.74 (d, J=13 Hz, 1H), 2.68 (d, J=13.6 Hz, 1H), 2.62 (d, J=13.6 Hz, 1H), 2.00–1.90 (m, 1H), 1.92–1.88 (m, 1H), 1.59–1.52 (m, 1H), 1.47–1.44 (m, 1H).

FAB-MS calc. for C$_{21}$H$_{26}$N$_2$O$_2$: 338; Found 339 (M+H)

Step F:

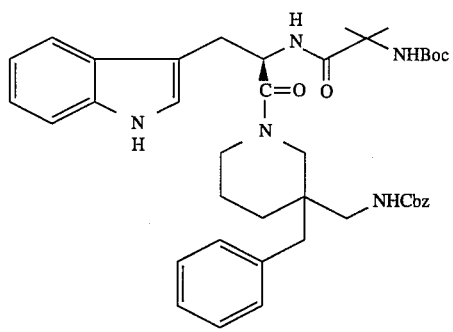

Prepared by the procedure described in Example 1, Step D from the intermediate prepared in the previous step (1.00 g, 2.67 mmol), Intermediate 1 (1.04 g, 1 eq.), HOBT (1 eq.), N-methyl morpholine (2 eq.), and EDC (820 mg, 4.27 mmol). Purification by MPLC, eluting with 60% ethyl acetate in hexane, provided the compound. (1.54 g, 81%)

Step G:

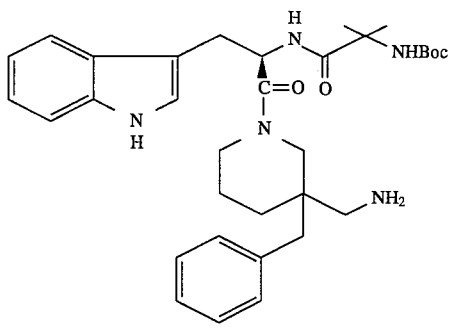

The intermediate from the previous step (1.30 g, 1.83 mmol) was hydrogenated over 10% palladium on carbon (100 mg) in ethanol (15 mL) under a hydrogen balloon. The reaction mixture was filtered through celite and evaporated to yield the amine (1.20 g, 100%).

FAB-MS calc. for C$_{33}$H$_{45}$N$_5$O$_4$: 575; Found 576 (M+H)

Step H:

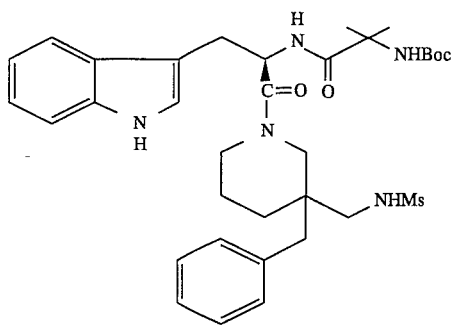

To a stirred solution of the intermediate prepared the previous step (286 mg, 0.497 mmol), DMAP (10 mg) and N-methyl morpholine (0.109 mL) in dichloromethane (10 mL) at 0° C. was added mesyl chloride (0.042 mL). The reaction mixture was stirred for 2 hours. The solution was poured into a mixture of brine and 3 N HCl and extracted with ethyl acetate. The organic layer was washed with saturated sodium bicarbonate dried over magnesium sulfate and evaporated to give a residue which was purified by flash chromatography, eluting with 90% ethyl acetate in hexane, to give the product (285.9 mg, 88%). FAB-MS calc. for C$_{34}$H$_{47}$N$_5$O$_6$S: 653; Found 654 (M+H)

Step I:

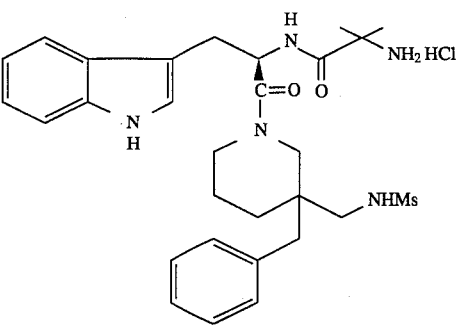

Prepared by the procedure described in Example 1, Step C from the intermediate from the previous step (265 mg, 0.405 mmol) and HCl gas in ethyl acetate (8 mL) at 0° C. for 30 minutes (189 mg, 79%)

FAB-MS calc. for C$_{29}$H$_{39}$N$_5$O$_4$S: 553; Found 554 (M+H)

EXAMPLE 20

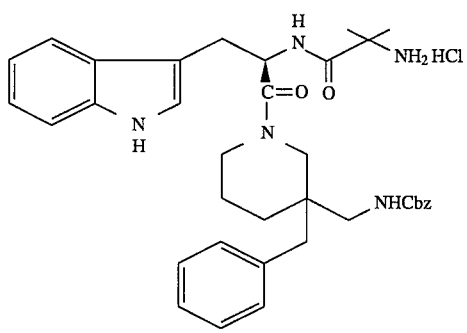

Prepared by the procedure described in Example 1, Step C from the intermediate from Example 19, Step F (109 mg, 0.154 mmol) and HCl gas in ethyl acetate (4 mL) at 0° C. for 30 minutes (90 mg, 90%).

FAB-MS calc. for $C_{36}H_{43}N_5O_4$: 609; Found 610 (M+H)

EXAMPLE 21

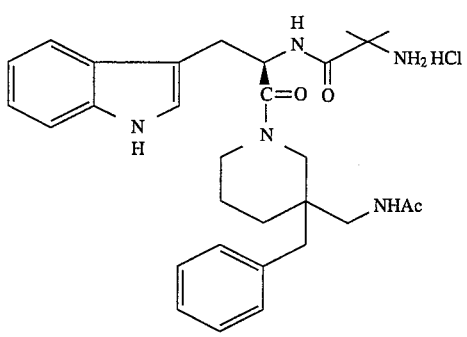

Step A:

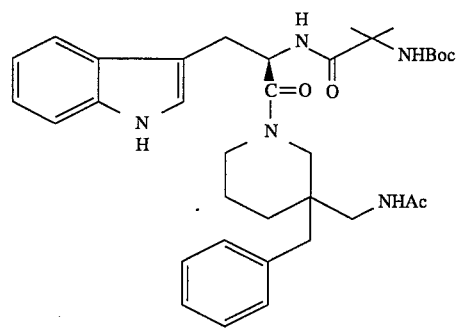

The mixture of the intermediates from Example 19, Step G (208 mg, 0.362 mmol) and pyridine (2 mL) and acetic anhydride (2 mL) was heated at 60° C. for 30 minutes. The mixture was then evaporated under vacuum. MPLC purification eluting with 80% ethyl acetate in hexane yielded the product (202 mg, 90%).

FAB-MS calc. for $C_{35}H_{47}N_5O_5$: 617; Found 618 (M+H)

Step B:

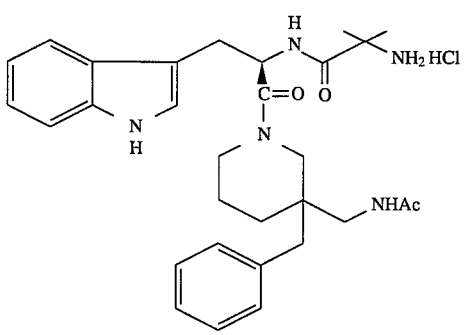

Prepared by the procedure described in Example 1, Step C from the intermediate from the previous step (192 mg, 0.311 mmol) and HCl gas in ethyl acetate (4 mL) at 0° C. for 30 minutes (168.1 mg, 98.5%).

FAB-MS calc. for $C_{30}H_{39}N_5O_3$: 517; Found 518 (M+H)

EXAMPLE 22

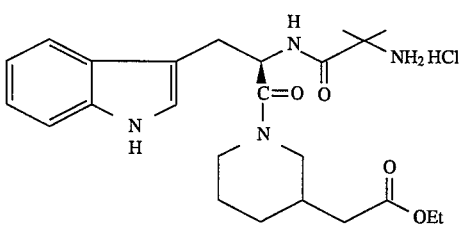

Step A:

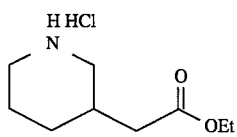

A suspension of platinum (IV) oxide (200 mg), ethyl 3-pyridylacetate (5.0 g, 30.3 mmol) and concentrated hydrochloric acid (10 mL) in ethanol (50 mL) was stirred under a hydrogen balloon overnight. The mixture was filtered through celite and evaporated to yield a residue, which was refluxed with anhydrous acidic ethanol for 30 minutes. Evaporation yielded the product (6.28 g, 100%).

$^1$H NMR (CD$_3$OD, 400 MHz) δ4.13 (q, J=7.2 Hz, 2H), 3.40 (dd, J=3.5 Hz, 12 Hz, 1H), 3.35 (br. d, 1H), 2.90 (br. t, 1H), 2.73 (t, J=12 Hz, 1H), 2.35 (d, J=7.5 Hz, 2H), 2.26–2.17 (m 1H), 1.96–1.80 (br. m, 2H), 1.80–1.70 (m, 1H), 1.37–1.26 (m, 1H), 1.24 (t, J=7.1 Hz, 3H).

Step B:

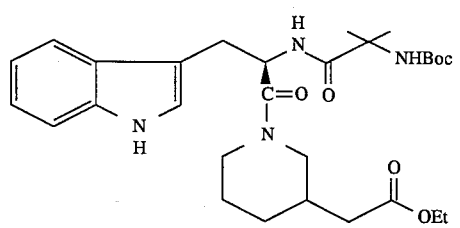

Prepared by the procedure described in Example 1, Step D from the intermediate prepared in the previous step (128 mg, 0.617 mmol), Intermediate 1 (200 mg, 0.514 mg, mmol), HOBT (1 eq.), N-methyl morpholine (1 eq.), and EDC (200 mg). Purification by MPLC eluting with 80% ethyl acetate in hexane provided the compound. (247 mg, 89%)

Step C:

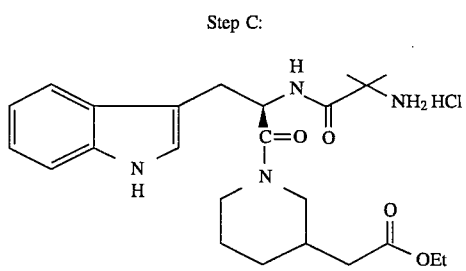

Prepared by the procedure described in Example 1, Step C from the intermediate from the previous step (225 mg, 0.415 mmol) and HCl gas in ethyl acetate (5 mL) at 0° C. for 15 minutes (184 mg, 100%).

FAB-MS calc. for $C_{24}H_{34}N_4O_4$: 442; Found 443 (M+H)

EXAMPLE 23

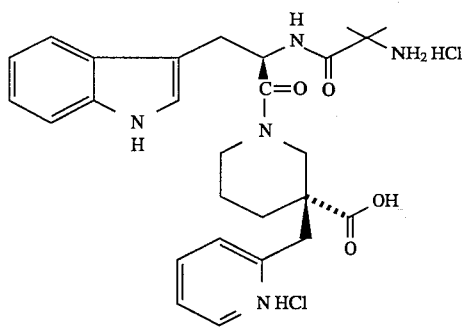

Step A:

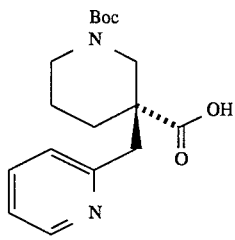

The less polar (d1) intermediate from Example 8 step A (7.25 g, 17.08 mmol) was refluxed for 8 hours in ethanol (20 ml) and 10N NaOH (8.5 mL). The mixture was then cooled to room temperature and slowly treated with 3N HCl to pH=11. To this stirred solution was added di-tert-butyl dicarbonate in dioxane (20 mL) and stirred for two hours. The solution was acidified to pH 4 and then neutralized to pH 7 and extracted with ethyl acetate three times. The organic extracts were combined, dried, and concentrated to give white solid (6.80 g).

FAB-MS calc. for $C_{17}H_{24}N_2O_4$: 320, Found: 321 (M+H)

Step B:

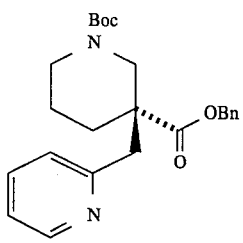

To a solution of the intermediate from the last step (6.5 g), benzyl alcohol (2 equiv.), and DMAP (20 mg) in dichloromethane (100 mL), was added EDC (1.2 equiv.). The mixture was stirred at room temperature for three days, and was poured into dilute NaHCO3 solution. It was extracted with ethyl acetate three times, and dried over MgSO4. Evaporation and purification by a flash column eluting with 40% ethyl acetate in hexane gave the desired product. (6.53 g, 78%).

FAB-MS calc. for $C_{24}H_{30}N_2O_4$: 410; Found 411 (M+H); 311 (M+-Boc(100)).

Step C:

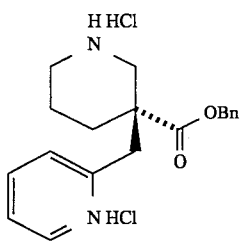

Prepared by the procedure described in Example 1, Step C from the intermediate from the previous step (1.0 g, 2.44 mmol) in ethyl acetate (40 mL) and HCl gas at 0° C. for 15 minutes (935 mg, 99%).

FAB-MS calc. for $C_{19}H_{22}N_2O_2$; 310; Found 311 (M+H)

Step D:

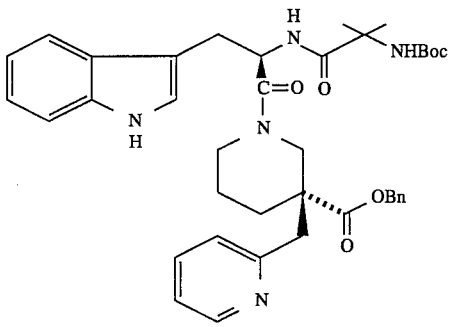

Prepared by the procedure described in Example 1, Step D from the intermediate prepared in the previous step (800 mg, 2.09 mmol), intermediate 1 (812 mg, 2.09 mmol), HOBT (1 eq.), N-methyl morphline (1 eq.), and EDC (2 eq.). Purification by MPLC, eluting with 80% ethyl acetate in hexane, provided the Intermediate (1.10 g, 77%)

d1 FAB-MS calc. for $C_{39}H_{47}N_5O_6$: 681; Found 682 (M+H)

95

Step E:

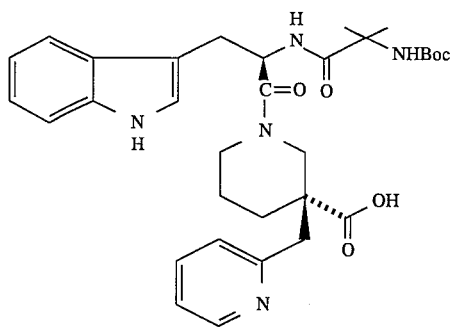

A suspension of 10% palladium on carbon (150 mg) and the intermediate from previous step (1.05 g, 1.54 mmol) in ethanol (20 mL) was vigorously stirred under a hydrogen atmosphere for 30 minutes. The reaction mixture was then filtered through celite and evaporated to give the product (828 mg, 91%). d1 FAB-MS calc. for $C_{32}H_{41}N_5O_6$: 591; Found 592 (M+H)

Step F:

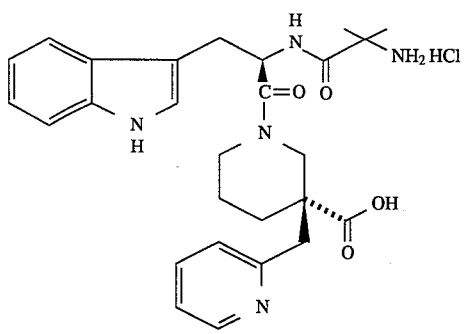

Prepared by the procedure described in Example 1, Step C from the intermediate from the previous step (211 mg, 0.357 mmol) and HCl gas in ethyl acetate (15 mL) at 0° C. for 10 minutes (175.6 mg, 93%).

d1 FAB-MS calc. for $C_{27}H_{33}N_5O_4$:491 Found 492 (M+H)

EXAMPLE 24

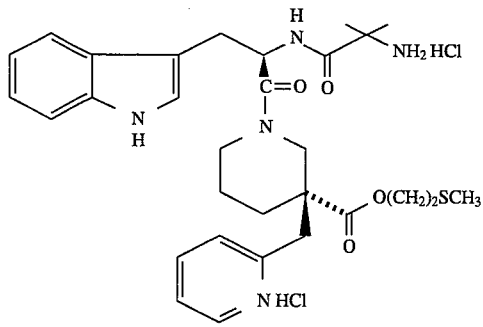

96
-continued
Step A:

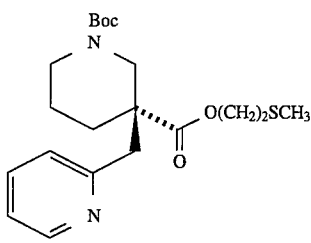

To a stirred solution of the product from Example 23, step A (5.79 g, 18.1 mmol), 2-(methylthio)ethanol (2.49 g, 27.1 mmol), DMAP (220 mg) in dichloromethane (100 mL) was added EDC and the mixture was stirred for one day. The reaction mixture was washed with brine, dried, evaporated, and purified on silica gel column eluting with 60% ethyl acetate in hexane to give the desired compound (6.64 g, 94%)

FAB-MS calc. for $C_{20}H_{30}N_2O_4S$: 394, Found: 395 (M+H)

Step B:

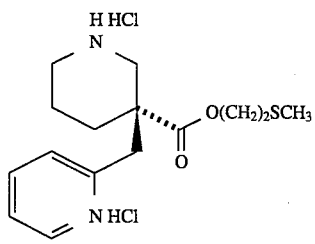

Prepared by the procedure described in Example 1, Step C from the intermediate from the previous step (6.12 g, 15.5 mmol) in ethyl acetate (30 mL) and HCl gas at 0° C. for 30 minutes (5.38 g, 95%).

FAB-MS calc. for $C_{15}H_{22}N_2O_2S$: 294 ; Found 295 (M+H)

Step C:

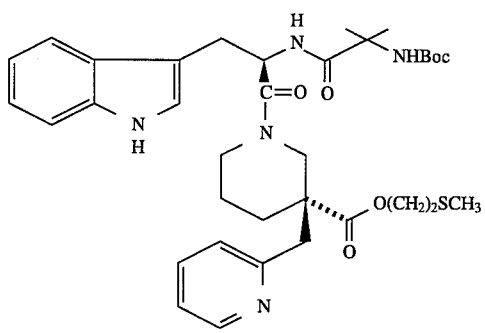

Prepared by the procedure described in Example 1, Step D from the intermediate prepared in the previous step (2.0 g, 5.44 mmol), Intermediate 1 (2.12, 5.44 mmol), HOBT (1 eq.), N-methyl morpholine (1 eq.), and EDC (1.5 eq.). Purification by MPLC, eluting with 80–100% ethyl acetate in hexane, provided the intermediate (3.44g, 95%)

FAB-MS calc. for $C_{35}H_{47}N_5O_6S$: 665; Found 666(M+H)

Step D:

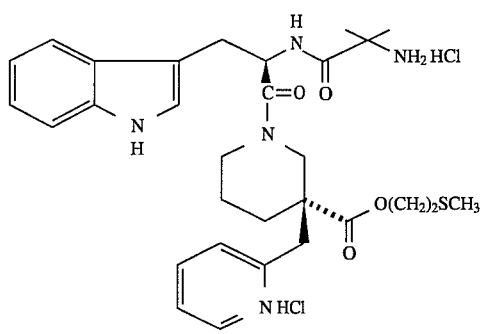

Prepared by the procedure described in Example 1, Step C from the intermediate from the previous step (2.94 g, 4.42 mmol) in ethyl acetate (10 mL) and HCl gas at 0° C. for 20 minutes (2.80 g, 99%).

FAB-MS calc. for $C_{30}H_{39}N_5O_4S$: 565; Found 566(M+H)

The additional intermediates shown in Table VII were prepared according to the above established procedure as exemplified in Example 24, steps A and B,. The final compounds were prepared according to Example 17 Steps D and E, using Intermediate 1.

TABLE VII

| entry | X | Intermediate MF FAB-MS (M + 1) | Final Product MF FAB-MS (M + 1) | isomer |
|---|---|---|---|---|
| 1 | $CO_2(CH_2)_2SMe$ | $C_{15}H_{22}N_2O_2S$ 295 | $C_{30}H_{39}N_5O_4S$ 566 | R |
| 2 | $CO_2Bn$ | $C_{19}H_{22}N_2O_2$ 311 | $C_{34}H_{39}N_5O_4$ 582 | R |
| 3 | $CO_2Bn$ | $C_{19}H_{22}N_2O_2$ 311 | $C_{34}H_{39}N_5O_4$ 582 | S |
| 4 | $CO_2(CH_2)_3CH_3$ | $C_{16}H_{24}N_2O_2$ 277 | $C_{31}H_{41}N_5O_4$ 548 | RS |
| 5 | $CO_2(CH_2)_2CH_3$ | $C_{15}H_{22}N_2O_2$ 263 | $C_{30}H_{39}N_5O_4$ 534 | RS |
| 6 | $CO_2CH(CH_3)_2$ | $C_{15}H_{22}N_2O_2$ 263 | $C_{30}H_{39}N_5O_4$ 534 | RS |
| 7 | $CONH(CH_2)_3CH_3$ | $C_{16}H_{25}N_3O$ 276 | $C_{31}H_{42}N_6O_3$ 547 | RS |
| 8 | $CONHCH(CH_3)_2$ | $C_{15}H_{23}N_3O$ 262 | $C_{30}H_{40}N_6O_3$ 533 | RS |
| 9 | $CO_2CH_2CO_2Et$ | $C_{16}H_{22}N_2O_4$ 306 | $C_{31}H_{39}N_5O_6$ 578 | RS |
| 10 | CONHEt | $C_{14}H_{21}N_3O$ 248 | $C_{29}H_{38}N_6O_3$ 519 | RS |
| 11 | $CONHCH_2CO_2Et$ | $C_{16}H_{23}N_3O_3$ 307 | $C_{31}H_{40}N_6O_5$ 577 | RS |

Note: RS compounds were prepared by using racemic intermediates instead of chiral ones.

TABLE VII-continued

EXAMPLE 24A

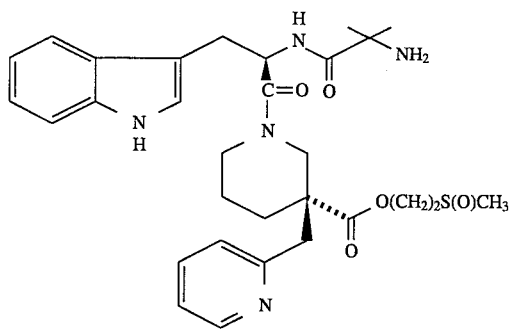

To a stirred solution of the final product from Example 24 (120 mg, 0.188 mmol) in ethanol/water (3/2 mL), was added sodium periodate (100 mg, 0.467 mmol) and the resulting mixture was stirred at room temperature for six hours. The reaction mixture was then poured into saturated sodium bicarbonate solution (10 mL) and extracted with dichloromethane (10 mL, 3 times). The organic extracts were combined and evaporated to give the desired compound (89 mg, 81%).

FAB-MS calc. for $C_{30}H_{39}N_5O_5S$: 581; Found 582(M+H)

EXAMPLE 25

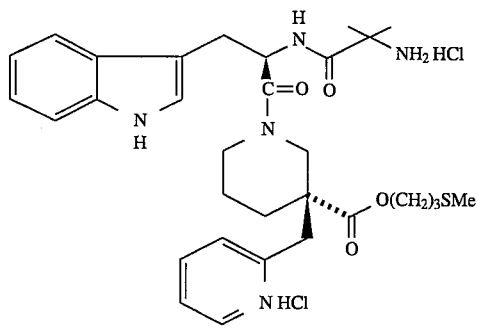

Step A:

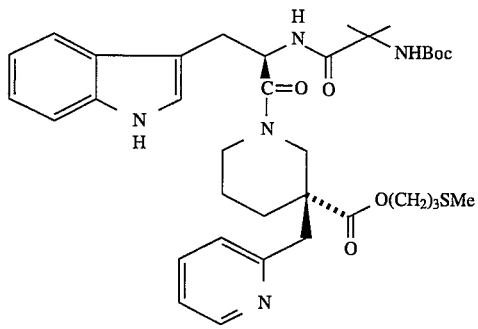

To a stirred solution of the intermediate from Example 23, step E (100 mg, 0.17 mmol), 3-(methylthio) propanol (18 mg, 0.17 mmol) and DMAP (3 mg) in dichloromethane (15 mL) was added EDC (1.5 equiv.), and the mixture was stirred at room temperature for one day. The reaction mixture was washed with water and brine, dried, evaporated and purified by MPLC eluting with 80% ethyl acetate in hexane to give the desired compound (88 mg). FAB-MS calc. for $C_{36}H_{49}N_5O_6S$: 679; Found 680(M+H)

Step B:

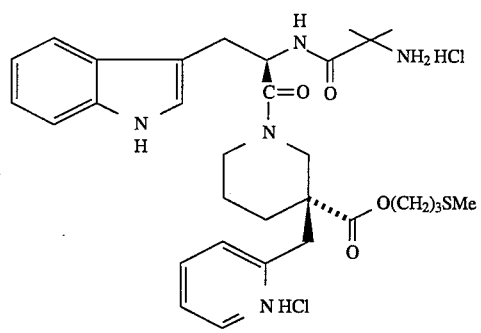

Prepared by the procedure described in Example 1, Step C from the intermediate from the previous step (85 mg, 0.125 mmol) in ethyl acetate (3 mL) and HCl gas at 0° C. for 20 minutes (74 mg, 95%).

FAB-MS calc. for $C_{31}H_{41}N_5O_4S$: 579; Found 580(M+H)

The compounds shown in Table VIII were prepared according to the above established procedure as exemplified in Example 25 using appropriate amines and alcohols.

TABLE VIII

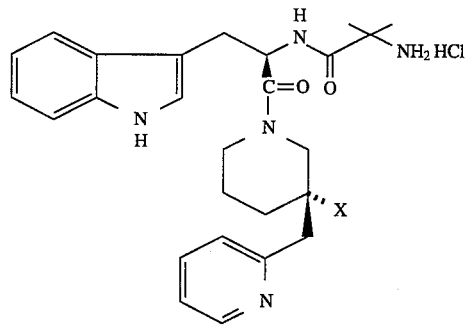

| entry | X | MF<br>FAB-MS (M + 1) |
|---|---|---|
| 1 | CO(morpholine) | $C_{31}H_{40}N_6O_4$<br>560 (M+, EI MS) |
| 2 | $CO_2(CH_2)_4SMe$ | $C_{32}H_{43}N_5O_4S$<br>594 |

TABLE VIII-continued

[Structure: Indole-CH2-CH(NH-C(=O)-C(CH3)2-NH2·HCl)-C(=O)-N-piperidine with X and CH2-pyridine substituents]

| entry | X | MF FAB-MS (M + 1) |
|---|---|---|
| 3 | CONH(CH2)2SMe | $C_{30}H_{40}N_6O_3S$ 565 |
| 4 | CONHEt | $C_{29}H_{38}N_6O_3$ 519 |
| 5 | CONH(CH2)2OH | $C_{29}H_{38}N_6O_4$ 535 |

Likewise using the intermediate from Example 23, Step C and following the procedures described in Step D and E using Intermediate 3 instead of Intermediate 1, the compounds shown in Table VIIIa were prepared according to the established procedures as exemplified in Example 25 using appropriate amines.

TABLE VIIIa

[Structure: Ph-(CH2)3-CH(NH-C(=O)-C(CH3)2-NH2·HCl)-C(=O)-N-piperidine with X and CH2-pyridine substituents]

| entry | X | MF FAB-MS (M + 1) |
|---|---|---|
| 1 | CONHEt | $C_{29}H_{41}N_5O_3$ 508 |
| 2 | CONH(CH2)2OH | $C_{29}H_{41}N_5O_4$ 524 |

Likewise using the intermediate from Example 23, Step E and following the procedure described above; or the intermediate from Example 23, step A and following the procedure described in Example 24 steps A through D using Intermediate 1 or Intermediate 3 the compounds shown in Table VIIIb may be prepared.

TABLE VIIIb

[Structure: R1-CH(NH-C(=O)-C(CH3)2-NH2)-C(=O)-N-piperidine with X and CH2-pyridine substituents]

| entry | R1 | X |
|---|---|---|
| 1 | indol-3-yl-CH2— | —CONHCH3 |
| 2 | Ph-(CH2)3— | —CONHCH3 |
| 3 | indol-3-yl-CH2— | —CONH(CH2)3OH |
| 4 | Ph-(CH2)3— | —CONH(CH2)3OH |
| 5 | Ph-(CH2)3— | —CONHCH2CH2SCH3 |

EXAMPLE 26

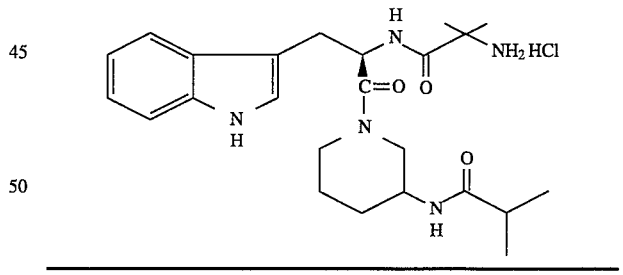

Step A: 3-Carbobenzyloxyaminopyridine

To a solution of 3-aminopyridine (10 g, 0.106 mol) and triethyl amine (16.3 mL, 0.117 mol) in dichloromethane (100 mL) at 0° C., was added benzyl chloroformate (15.2 mL, 0.106 mol) slowly. The reaction mixture was stirred overnight and was washed with water, saturated NaHCO3, dried over MgSO4, and evaporated. The residue was purified on a silica gel column to give the product (9.51 g)

FAB-MS calc. for $C_{13}H_{12}N_2O_2$: 228; Found 229(M+H)

Step B: 3-Carbobenzyloxyaminopiperidine

A solution of the intermediate from the previous step (9.51 g, 41.7 mmol) and hydrochloric acid (3.5 mL, 41.7 mmol) in ethanol (300 mL) was hydrogenated over PtO2 (0.9 g) and hydrogen (1 atm) overnight. Filtration and evaporation gave the product as a brown solid.

FAB-MS calc. for $C_{13}H_{18}N_2O_2$: 234; Found 235(M+H)

Step C:

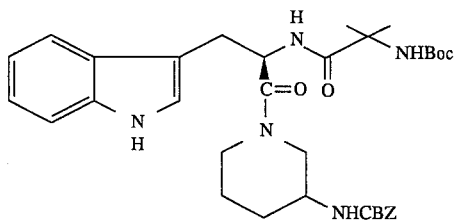

To a solution of the intermediate from the previous step (4.65 g, 17.2 mmol), Intermediate 1 (6.68 g, equiv.), HOBT (2.32 g, 1 equiv.) and NMM (2.1 mL, 1 equiv.) in dichloromethane (100 mL), was added EDC (3.94 g, 1.2 equiv.). The reaction mixture was stirred overnight and worked up by washing with water, saturated NaHCO3, dried over MgSO4 and evaporated. Purification on a $SiO_2$ column gave 2.5 g of the desired product.

FAB-MS calc. for $C_{33}H_{43}N_5O_6$: 605; Found 606(M+H)

Step D:

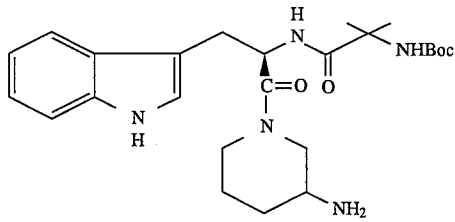

A suspension of the intermediate from the previous step (2.5 g) and $Pd(OH)_2/C$ (250 mg, 10%) in methanol (60 mL) was stirred under H2 (1 atm) for three days. The reaction mixture was filtered through celite and evaporated to give the desired material.

FAB-MS calc. for $C_{25}H_{37}N_5O_4$: 471; Found 472(M+H)

Step E:

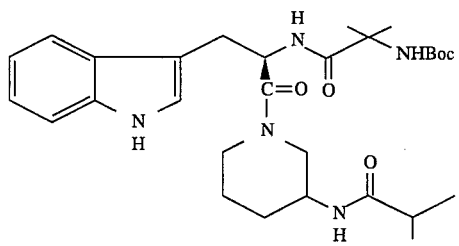

To a solution of the intermediate from the previous step (236 mg, 0.5 mmol) and N,N-diisopropylethylamine (0.11 mL, 0.6 mmol) in dichloromethane (10 mL), was added isobutyryl chloride (0.053 mL, 0.5 mmol) at 0°. The reaction mixture was stirred for 2 hours and was washed with water, brine, dried over MgSO4 and evaporated. $SiO_2$ flash column chromatography eluting with 90–100% ethyl acetate in hexane yielded the product.

FAB-MS calc. for $C_{29}H_{43}N_5O_5$: 541; Found 542(M+H)

Step F:

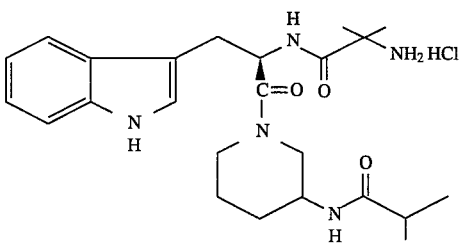

To a solution of the intermediate from the previous step in ethyl acetate (5 mL) at 0° C. was bubbled HCl until it was saturated. The mixture was stirred for 30 minutes and evaporated to dryness to give the product. FAB-MS calc. for $C_{24}H_{35}N_5O_3$: 441; Found 442(M+H)

Similarly the following compounds were prepared according to the same procedure as described above, but using different acylating reagents.

TABLE IX

| entry | Acylating agent | Y | MF FAB-MS (M + 1) |
|---|---|---|---|
| 1 | Ac2O | AcNH | $C_{22}H_{31}N_5O_3$ 414 |
| 2 | ChxCOCl | ChxCONH | $C_{27}H_{39}N_5O_3$ 482 |
| 3 | ChxCH2COCl | ChxCH2CONH | $C_{28}H_{41}N_5O_3$ 496 |
| 4 | BzCl | BzNH | $C_{27}H_{33}N_5O_3$ 476 |
| 5 | PhSO2Cl | PhSO2NH | $C_{26}H_{33}N_5O_4S$ 512 |
| 6 | iso-PrNCO | iso-PrNHCONH | $C_{24}H_{36}N_6O_3$ 457 | note: Chx: cyclohexyl, Bz: benzoyl

EXAMPLE 27

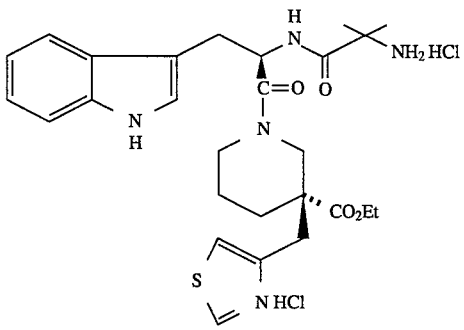

TABLE IX-continued

Step A:

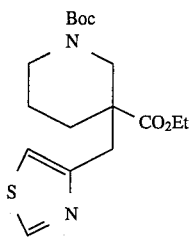

To a stirred solution of KHMDS (27.4 g, 0.138 mol) in THF (500 mL) at −78° C. under argon was added ethyl N-t-Boc nipecotate (28.3 g, 0.11 mol) in THF (100 mL) over a 20 minute period. The solution was allowed to stir an additional 30 minutes at −78° C. Then, a solution of 4-bromomethylthiazole or 4-chloromethylthiazole in THF (100 mL) was added slowly to the reaction mixture. 4-Bromomethylthiazole was prepared by refluxing 4-methylthiazole (10 mL, 0.11 mmol), N-bromosuccinimide (19.6 g, 0.11 mol) and AIBN (0.2 g) in CCl$_4$ (300 mL) for 2 hours, cooled to room temperature, filtered and evaporated; 4-chloromethylthiazole can be prepared as described by Hsiao, C-H et al, Synthetic Communications, 20 (22), 3507–3417 (1990) and Caldwell, W and Fox, S. M. J. Am. Chem. Soc. 73,2935 (1955). The resulting black mixture was stirred overnight and allowed to warm to room temperature. The material was concentrated, then diluted with water, and extracted using ethyl acetate. The organic layer was dried over anhydrous magnesium sulfate, filtered, and concentrated. Purification by silica gel flash column chromatography eluting with a solvent gradient of 30–65% ethyl acetate in hexane provided the title compound. (7.58 g, 20%).

FAB-MS calc. for $C_{17}H_{26}N_2O_4S$ 354; Found 355 (M+H)

Step B:

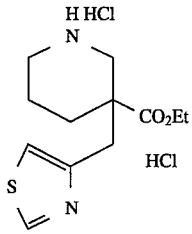

To a solution of the intermediate from the previous step (7.0 g, 19.8 mmol) in ethyl acetate (100 mL) at 0° C., was bubbled hydrogen chloride gas until saturation occurred. The reaction was stirred for 30 minutes, and then concentrated to remove the ethyl acetate to afford the product (5.3 g, 93%). $^1$H NMR (CDCl$_3$, 400 MHz) δ9.67 (s, 1H), 7.75 (s, 1H), 4.34–4.15 (2 m, 2H), 3.67 (d,J=12.8 Hz, 1H), 3.34 (d,J=15 Hz, 1H), 3.28 (d,J=12.5 Hz, 1H), 3.21 (d,J=15 Hz, 1H), 3.01 (dt,J=3.0, 12.5 Hz, 1H), 2.26 (br.d,J=13.7 Hz, 1.97–1.92 (m, 1H), 1.80 (dt, J=3.5, 13 Hz, 1H), 1.78–1.58 (m, 1H), 1.26 (t,J=7.2 Hz, 3H). FAB-MS calc. for $C_{12}H_{18}N_2O_2S$: 254; Found 255 (M+H)

Step C:

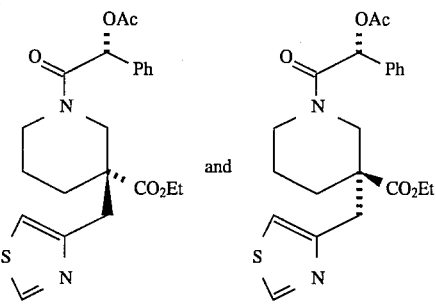

To a stirred solution of the intermediate (6 g, 18.67 mmol) prepared in Step B, (R)-(−)-(O)-acetyl mandelic acid (1 eq.), HOBT (1 eq.) and NMM (2 eq.) at 0° C. was added EDC (7.16 g, 37.34 mmol). The reaction mixture was stirred overnight during which time it was allowed to warm to room temperature. The solution was poured into brine and extracted with CH2C12. The organic layer was dried over MgSO4, evaporated and purified with a SiO$_2$ flash column eluting with 40–80% ethyl acetate in hexane to provided two enantiomerically pure compounds. The isomer which came out of the column first was designated as d1 (2.17 g, 30%) and the isomer which came out of the column second as d2 (0.87 g, 12%) and mixed fraction (700 mg). The stereochemistry assignment was made by NMR comparison of these compounds with the intermediates obtained in Example 8 Step A. The absolute stereochemistry of those intermediates was established by X-ray analysis. FAB-MS calc. for $C_{22}H_{26}N_2O_5S$: 430; Found 431(M+H)

d1: $^1$H NMR (CDCl$_3$, 400 MHz) indicated the compound exists as a mixture of two conformers. δ8.77, 8.65 (2 s, 1H) 7.46–7.34 (m, 5H), 7.07, 7.02 (2 s, 1H), 6.64, 6.23 (2 s, 1H), 4.29 (br. d, J=13.9 Hz, 1/2H), 4.10–4.02 (m, 3/2H), 3.92–3.87 (m, 3/2H), 3.61 (d, J=13.5 Hz, 1/2H), 3.46 (d, J=14 Hz, 1/2H), 3.40–3.32 (m, 1/2H), 3.25–3.21 (m, 1/2H), 3.18 (d, J=14 Hz, 1/2H), 3.06 (d, J=14 Hz, 1/2H), 2.96 (d, J=14 Hz, 1/2H), 2.84 (d, J=14 Hz, 1/2H), 2.85–2.75 (br. m, 1/2H), 2.14,2.11 (2 s, 3H), 1.90–1.82 (m, 1/2H), 1.80–1.75 (m, 1H), 1.61–1.55 (m, 1H), 1.50–1.40 (br. m, 1/2H), 1.14 (t, J=7 Hz, 3/2H), 1.03 (t, J=7 Hz, 3/2H).

d2: $^1$H NMR (CDCl$_3$, 400 MHz) indicated the compound exists as a mixture of two conformers. δ8.71, 8.68 (2d, J=1.8 Hz, 1H), 7.41–7.34 (m, 5H, 7.06, 6.83 (2 d, J=1.8 Hz, 1H), 6.41 6.20 (2s, 1H), 4.46 (br. d, J=13.4 Hz, 1/2H), 4.24–3.93 (m, 3H), 3.41 (d, J=13.5 Hz, 1/2H), 3.31–3.28 m, 1H), 3.13 (d, J=14.2 Hz, 1/2H), 3.04 (d, J=14.2 Hz, 1/2H), 3.04 (d, J=14.2 Hz, 1/2H), 2.92 (d, J=14 Hz, 1/2H), 2.73 (d, J=14 Hz, 1/2H), 2.54 (d, J=13.8 Hz, 1H), 2.30 (br. d, J=13 Hz), 2.15, 2.09 (2 s, 3H), 2.00–1.95 (m, 1/2H), 1.65–1.49 (m, 2H), 1.37 (dt, J=4, 12.8 Hz, 1/2H), 1.17–1.10 (m, 3H).

Step D:

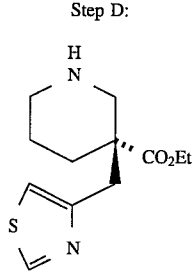

A solution of the intermediate d1 from the previous step (2.0 g, 4.65 mmol) concentrated hydrochloric acid (25 mL) and ethanol (25 mL) was refluxed for 3 hours and was evaporated to dryness. The residue was neutralized by ammonium hydroxide and extracted by dichloromethane, and then was purified by SiO2 flash column eluting with 1:10:90 NH4OH:MeOH:CHCl3 to yield the product (0.72 g, 61%).

$^1$H NMR (CD$_3$OD, 400 MHz) δ8.88 (d, J=2 Hz, 1H), 7.21 (d, J=2 Hz, 1H), 4.20–4.07 (m, 2H), 3.28 (br. d, 1H), 3.06 (d, JAB=14 Hz, 1H), 2.97 (d, JBA=14 Hz, 1H), 2.92–2.80 (md, 1H), 2.61–2.57 (m, 2H), 2.21–2.16 (br. d, 1H), 1.66–1.40 (m, 3H), 1.20 (t, J=7.3 Hz, 3H).

FAB-MS calc. for $C_{12}H_{18}N_2O_2S$: 254; Found 255 (M+H)

Step E:

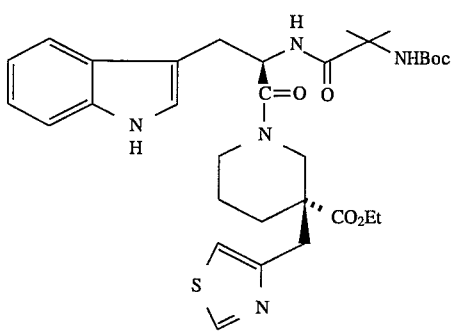

To a stirred solution of the intermediate from the previous step (163 mg, 0.642 mmol), Intermediate 1 (250 mg, 0.642 mmol) and HOBT (87 mg, 0.642 mmol) in dichloromethane (20 mL) was added EDC (247 mg, 1.28 mmol) at 0° C. The reaction mixture was stirred overnight and allowed to warm to room temperature. The solution was washed with saturated sodium chloride, dried over anhydrous magnesium sulfate; then filtered and concentrated. Purification by MPLC eluting with 60% ethyl acetate in hexane provided the desired compound (285 mg, 71%). FAB-MS calc. for $C_{32}H_{43}N_5O_6S$: 625; Found 626 (M+H); 526 (M$^+$-Boc(100)).

Step F:

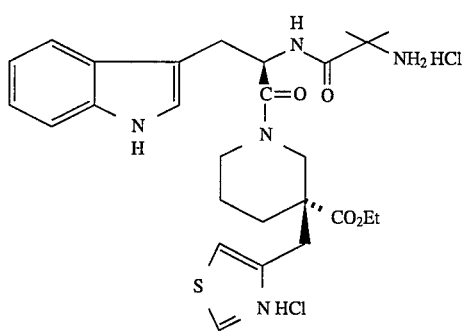

Hydrogen chloride gas was bubbled into a solution of the intermediate from the previous step (270 mg, 0.43 mmol) in ethyl acetate (10 mL) at 0° C. until it was saturated. The reaction was stirred for 30 minutes, and evaporated to remove the ethyl acetate to afford the product (226 mg, 93%). $^1$H NMR (CD3OD, 400 MHz): 9.90 (d, J=2.2 Hz, 4/5H), 9.5 (d, J=2.2 Hz, 1/5H), 8.48 (d, J=7.15, 4/5H), 8.15 (d, 7.15, 1/5H), 7.70 (d, J=2.2 Hz, 4/5H), 7.68 (d, J=2.2, 1/5H), 7.55 (d, J=7.89 Hz, 1H), 7.27 (d, J=8.0 Hz, 1H), 7.06–6.95 (M, 1H), 3.94 (q, J=7.1 Hz, 2H), 3.94 (q, J=7.1 Hz, 2H), 2.37 (d, J=14.9, 1H), 1.90 (d, J=14.9, 1H), 1.60(s, 6H), 1.07 (t, J=7.1 Hz, 3H), FAB-MS calc. for $C_{27}H_{35}N_5O_4S$: 525; Found 526 (M+H)

EXAMPLE 27A

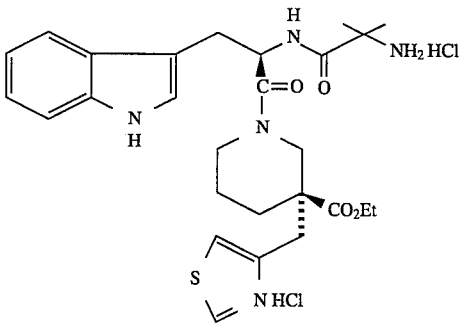

Following the same procedures as in Example 27 and using the product d2 from step C, the title compound was prepared.

FAB-MS calc. for $C_{27}H_{35}N_5O_4S$: 525; Found 526 (M+H)

The additional intermediates shown in Table X were prepared with the corresponding alkylating agents according to the above established procedure as exemplified in Example 27 steps A and B. The final compounds were prepared according to Example 1 Steps D and E, using Intermediate 1.

TABLE X

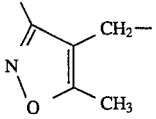

| entry | Y | Intermediate MF FAB-MS (M + 1) | Product MF FAB-MS (M + 1) | isomer |
|---|---|---|---|---|
| 1 | H3C-C(=N-O)-C(CH2—)=C(CH3) (isoxazolyl) | $C_{14}H_{22}N_2O_3$ 267 | $C_{29}H_{39}N_5O_5$ 538 | RS |
| 2 | 2-thiazolylmethyl | $C_{12}H_{18}N_2O_2S$ 255 | $C_{27}H_{35}N_5O_4S$ 526 | RS |
| 3 | 4-thiazolylmethyl | $C_{12}H_{18}N_2O_2S$ 255 | $C_{27}H_{35}N_5O_4S$ 526 | RS |
| 4 | 5-thiazolylmethyl | $C_{12}H_{18}N_2O_2S$ 255 | $C_{27}H_{35}N_5O_4S$ 526 | RS |
| 5 | (4-methyl-2-thiazolyl)methyl | $C_{13}H_{20}N_2O_2S$ 269 | $C_{28}H_{37}N_5O_4S$ 540 | RS |
| 6 | (2-methyl-4-thiazolyl)methyl | $C_{13}H_{20}N_2O_2S$ 269 | $C_{28}H_{37}N_5O_4S$ 540 | RS |
| 7 | (4-methyl-5-thiazolyl)methyl | $C_{13}H_{20}N_2O_2S$ 269 | $C_{28}H_{37}N_5O_4S$ 540 | RS |
| 8 | (5-methyl-4-thiazolyl)methyl | $C_{13}H_{20}N_2O_2S$ 269 | $C_{28}H_{37}N_5O_4S$ 540 | RS |

EXAMPLE 28

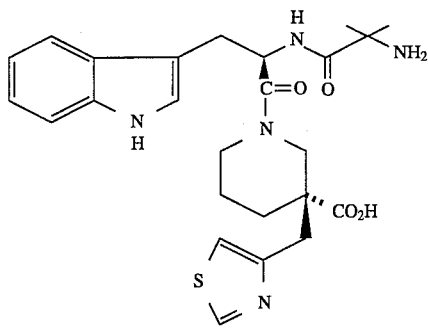

A solution of the final product of Example 27 (50 mg), NaOH (3N, 5 equiv.) in an mixture of ethanol/water (3:1, 5 mL) was stirred at 60° C. for two days. The reaction mixture as then evaporated in vacuo to remove ethanol. The residue was acidified by hydrochloric acid to pH=1 and then evaporated to dryness. The white residue was purified by silica gel column eluting with 3/30/70 NH4OH/MeOH/CHCl3 to give the desired product (25 mg). FAB-MS calc. for $C_{25}H_{31}N_5O_4S$: 497; Found 498(M+H)

EXAMPLE 29

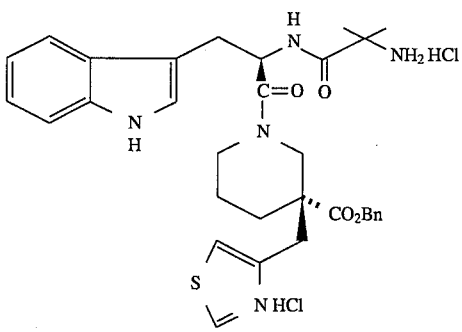

Step A:

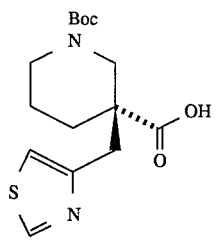

The less polar (d1) intermediate from Example 27 step C (1.5 g, 3.48 mmol) was refluxed for 2 hours in ethanol (10 ml) and 5N NaOH (3.5 mL). The mixture was then cooled to room temperature and slowly treated with 3N HCl to pH=11. To this stirred solution was added di-tert butyl dicarbonate (1.52 g, 7 mmol) and stirred for two hours. The solution was acidified to pH 4 and then neutralized to pH 7 and extracted with ethyl acetate three times. The organic extracts were combined, dried, and concentrated to give white solid (810 mg).

Step B:

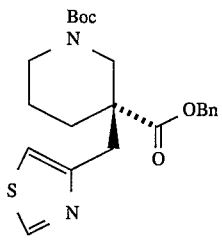

To a solution of the intermediate from the last step (800 mg), benzyl alcohol (1.27 mL), and DMAP (30 mg) in dichloromethane (40 mL), was added EDC (935 mg, 4.9 mmol). The mixture was stirred at room temperature for three days, and was poured into dilute $NaHCO_3$ solution. It was extracted with ethyl acetate three times, and dried over $MgSO_4$. Evaporation and purification by a flash column eluting with 20–40% ethyl acetate in hexane gave the desired product.(145 mg).

Step C:

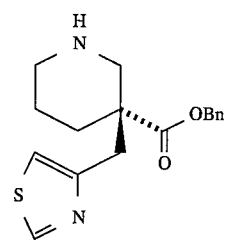

Prepared by the procedure described in Example 1, Step C from the intermediate from the previous step (140 mg) in ethyl acetate (20 mL) and HCl gas at 0° C. for 15 minutes. After evaporation, the residue was dissolved in dichloromethane and the solution was washed with NH4OH. The organic layer was dried evaporated to give the product.

Step D:

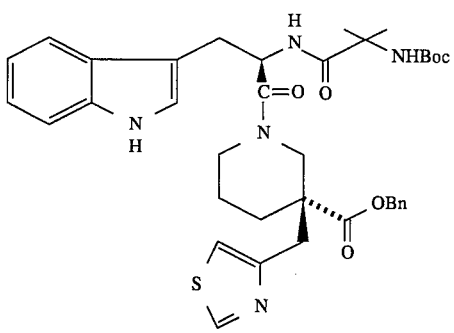

Prepared by the procedure described in Example 1, Step D from the intermediate prepared in the previous step (140 mg, 0.443 mmol), Intermediate 1 (172 mg, 0.443 mmol), HOBT (60 mg.) and EDC (170 mg). Purification by MPLC, eluting with 80% ethyl acetate in hexane, provided the intermediate (210 mg).

Step E:

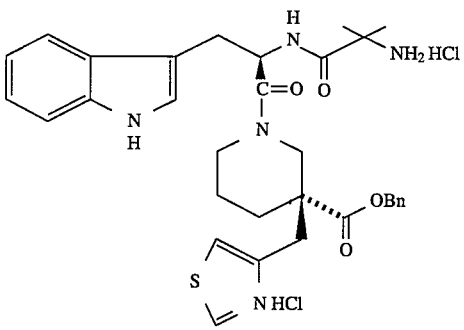

Prepared by the procedure described in Example 1, Step C from the intermediate from the previous step (12 mg, 0.018 mmol) and HCl gas in ethyl acetate (3 mL) at 0° C. for 10 minutes.

Likewise it is possible to prepare the compounds shown in Table Xa according to this example by reacting the intermediate from Example 29, Step A, with methylamine, ethylamine, ethanolamine, 3-aminopropanol or 2-(methylthio)ethylamine instead of benzyl alcohol in Step B, and using Intermediate 1 or Intermediate 3 in Step D.

TABLE Xa

Structure: R₁-CH(NHC(=O)C(CH₃)₂NH₂)-C(=O)-N(piperidine with X substituent and thiazole-CH₂ group)

| entry | R1 | X |
|---|---|---|
| 1 | (1H-indol-3-yl)-CH₂— | —CONHCH₃ |
| 2 | phenyl-(CH₂)₃— | —CONHCH₃ |
| 3 | (1H-indol-3-yl)-CH₂— | —CONHCH₂CH₃ |
| 4 | phenyl-(CH₂)₃— | —CONHCH₂CH₃ |
| 5 | (1H-indol-3-yl)-CH₂— | —CONHCH₂CH₂OH |
| 6 | phenyl-(CH₂)₃— | —CONHCH₂CH₂OH |
| 7 | (1H-indol-3-yl)-CH₂— | —CONH(CH₂)₃OH |
| 8 | phenyl-(CH₂)₃— | —CONH(CH₂)₃OH |
| 9 | (1H-indol-3-yl)-CH₂— | —CONH(CH₂)₂SCH₃ |
| 10 | phenyl-(CH₂)₃— | —CONH(CH₂)₂SCH₃ |

TABLE Xa-continued

EXAMPLE 30

[Structure of final product with phenyl-(CH₂)₃—, NH₂·HCl group, piperidine with CO₂Et and thiazole-CH₂ substituent, N·HCl]

Step A:

[Structure of BOC-protected intermediate with NHBOC, piperidine with CO₂Et and thiazole-CH₂]

Prepared by the procedure described in Example 1, Step D from the intermediate prepared in Example 27 Step D (134 mg, 0.528 mmol), Intermediate 3 (200 mg, 0.528 mmol), HOBT (71 mg, 1 eq.), and EDC (200 mg, 2 eq.). Purification by MPLC, eluting with 60% ethyl acetate in hexane provided the intermediate (160 mg, 49%)

FAB-MS calc. for $C_{32}H_{46}N_4O_6S$: 606; Found 607 (M+H)

Step B:

[Structure of deprotected product with NH₂·HCl, piperidine with CO₂Et and thiazole-CH₂, N·HCl]

Prepared by the procedure described in Example 1, Step C from the intermediate from the previous step (155 mg, 0.252 mmol) and HCl gas in ethyl acetate (5 mL) at 0° C. for 10 minutes (142 mg, 96%).

FAB-MS calc. for $C_{27}H_{38}N_4O_4S$: 506; Found 507 (M+H)

EXAMPLE 31

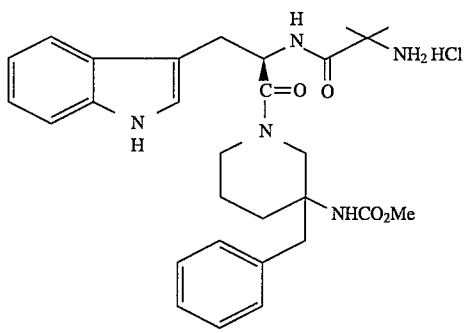

Step A:

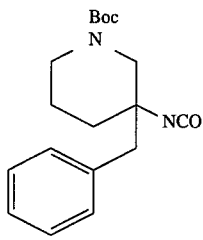

To a stirred solution of the product from example 15 step A (2.00 g, 6..26 mmol) and DMF (3 drops) in benzene (20 mL) at 0° C., was added oxalyl chloride (0.89 g, 6.89 mmol) slowly. The reaction was stirred at 0° C. for 10 minutes and another 20 minutes at room temperature. The reaction mixture was evaporated in vacuo to give the acyl chloride and it was used for the next reaction without further purification. To a stirred solution of the residue in acetone (20 mL) at 5° C., was added sodium azide (1.22 g, 18.8 mmol) in water (3 mL) and the resulting mixture was stirred at room temperature for 30 minutes. The reaction mixture was evaporated to remove acetone, and was diluted with water and extracted with ether. The other extracts were combined and dried over MgSO4. Filtration and evaporation gave the crude azide and it was used without further purification. The resulting material was dissolved in toluene (70 mL) and was refluxed overnight to give the isocyanate toluene solution. FAB-MS calc. for $C_{18}H_{24}N_2O_3$: 316; Found 217 (M+H-BOC(100)).

Step B:

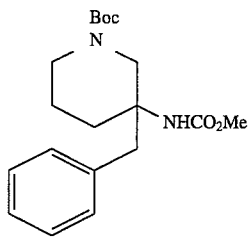

A solution of methanol (5 mL) and the solution obtained from the last step (15 mL out of 70 mL total, 1.3 mmol) was refluxed overnight. The reaction mixture was evaporated to give a white solid (331 mg). FAB-MS calc. for $C_{19}H_{28}N_2O_4$: 348; Found 349 (M+H).

Step C:

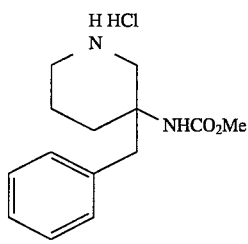

To a solution of the intermediate from the previous step (271 mg) in ethyl acetate (15 mL) at 0° C., was bubbled hydrogen chloride gas until saturation occurred. The reaction was stirred for 30 minutes, until TLC analysis indicated that the reaction was complete. The solution was then concentrated to remove the ethyl acetate to afford the product (284 mg). FAB-MS calc. for $C_{14}H_{20}N_2O_2$: 248; Found 249 (M+H)

Step D:

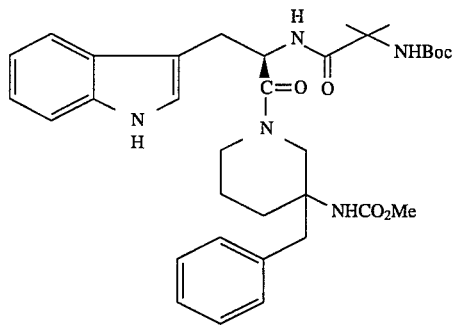

Prepared by the procedure described in Example 1, Step D from the intermediate prepared in the previous step (0.284 g, 1 mmol), Intermediate 1 (0.388 g, 1 mmol), HOBT (1 eq.), N-methyl morpholine (1 eq.), and EDC (1.5 eq.). Purification by MPLC, eluting with 60% ethyl acetate in hexane, provided the intermediate (0.35 g).

FAB-MS calc. for $C_{34}H_{45}N_5O_6$: 619; Found 620 (M+H)

Step E:

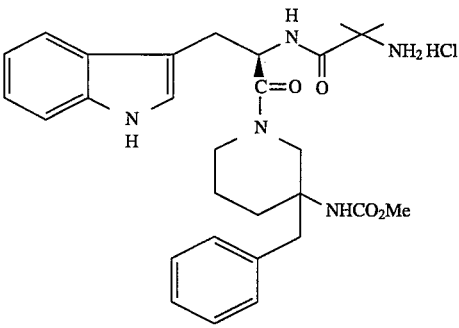

To a solution of the intermediate from the previous step (200 mg, mmol) in ethyl acetate (10 mL) at 0° C., was bubbled hydrogen chloride gas until saturation occurred. The reaction was stirred for 30 minutes, and then concentrated to remove the ethyl acetate to afford the product (158 mg). FAB-MS calc. for $C_{29}H_{37}N_5O_4$: 519; Found 520 (M+H)

EXAMPLE 32

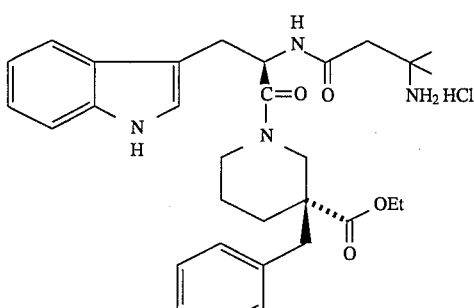

Step A:

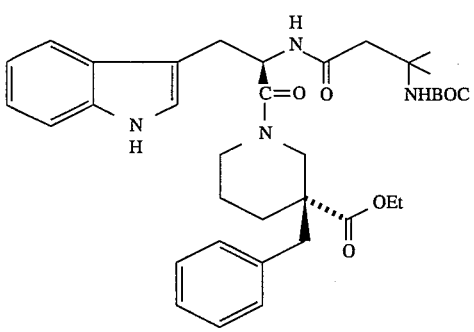

To a stirred suspension of the intermediate obtained in Example 2, step C (HCl salt, 2.51 g, 5.34 mmol), N-Boc-β-amino-β-Me-butyric acid (1.16 g, 1 equiv.), NMM (0.6 mL, 1 equiv.) and DMAP (33 mg, 0.05 equiv.) in dichloromethane (30 mL), was added EDC (1.55 g, 1.5 equiv.) in several portions. The reaction mixture quickly became clear and it was stirred for 3 hours and was worked up by diluting it with dichloromethane and washing with 3N HCl, brine, and saturated sodium bicarbonate solution. The organic layer was dried over MgSO4, evaporated and purified by silica gel column chromatography, eluting with 60% ethyl acetate in hexane to give the desired compound (3.40 g, 100%). FAB-MS calc. for $C_{36}H_{48}N_4O_6$:632; Found 633 (M+H)

Step B:

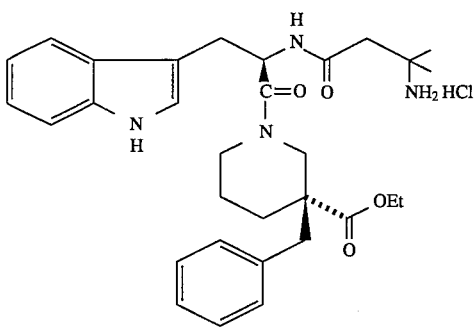

To a stirred solution of the intermediate from the previous step (3.28 g, 5.18 mmol) in ethyl acetate (30 mL) at 0° C., was bubbled HCl gas until it was saturated. The reaction was stirred for 10 minutes, and was evaporated to dryness. The residue was dissolved in dichloromethane, and to which ether was added. The solid which formed was collected by filtration, and it was air dried and left under high vacuum overnight to give the product (2.44 g, 83%).

FAB-MS calc. for $C_{31}H_{40}N_4O_4$:532; Found 533 (M+H)

Similarly the following compounds were prepared according to the same procedure as described above, but using different Boc protected amino acids which were subsequently deprotected as described above.

TABLE XI

| entry | $R_{11}$ | MF<br>FAB-MS (M + 1) |
|---|---|---|
| 1 | D-Ala— | $C_{29}H_{36}N_4O_4$<br>505 |
| 2 | L-Ala— | $C_{29}H_{36}N_4O_4$<br>505 |
| 3 | β-Ala— | $C_{29}H_{36}N_4O_4$<br>505 |
| 4 | DL-α-Me—Ser— | $C_{30}H_{38}N_4O_5$<br>535 |
| 5 | 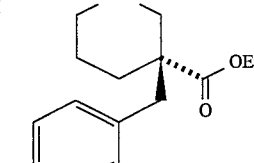 | $C_{30}H_{36}N_4O_4$<br>517 |
| 6 | 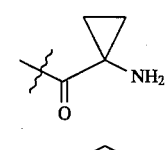 | $C_{33}H_{42}N_4O_4$<br>559 |
| 7 | D-Pro— | $C_{31}H_{38}N_4O_4$<br>531 |
| 8 | N-Me—Aib— | $C_{31}H_{40}N_4O_4$<br>533 |

EXAMPLE 33

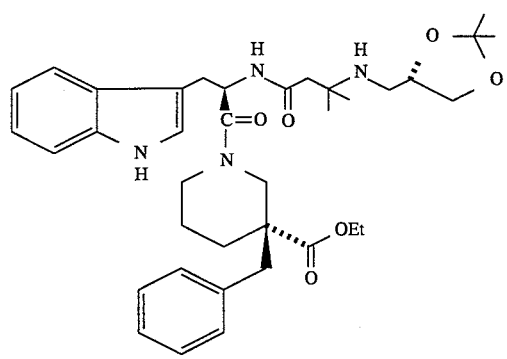

To a stirred solution of the product from Example 32 (808 mg, 1.42 mmol), (R)-glyceraldehyde acetonide (923 mg, 5 equiv.) and sodium acetate (582 mg, 5 equiv.) in methanol (15 mL) at 0° C., was slowly added sodium cyanoborohydride (134 mg, 1.5 equiv.) and the resulting mixture was stirred at room temperature overnight. The mixture was evaporated to remove methanol and partitioned between sodium bicarbonate solution and dichloromethane. The organic layer was separated and the aqueous layer was extracted two more times with dichloromethane. The combined organic extracts were dried over magnesium sulfate and purified by a silica gel column, eluting with 5–10% methanol in dichloromethane to give the product (835 mg, 91%)

FAB-MS calc. for $C_{37}H_{50}N_4O_6$:646; Found 647 (M+H)

EXAMPLE 34

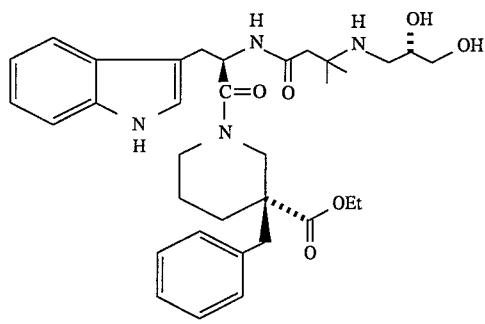

To a solution of the product from Example 33 (367 mg, 0.566 mmol) in methanol (10 mL) was added hydrochloric acid (3N, 1 mL) and the resulting mixture was stirred at room temperature for one day. The reaction mixture was evaporated in vacuo, and toluene was added and evaporated in vacuo again to remove the residual water to give the product (350 mg, 99%). FAB-MS calc. for $C_{34}H_{46}N_4O_6$:606; Found 607 (M+H)

EXAMPLE 35

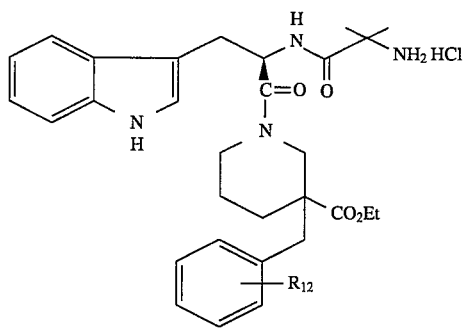

Additional benzyl substituted intermediates and products as shown in Table XII were prepared according to procedures described in Example 1 Steps A and B using appropriately substituted benzyl halides in the alkylation step. Functional groups changes as needed were made at the intermediate Step B stage to convert as needed cyano groups to carboxamides, esters and tetrazoles, nitro groups to amines and acetylamines and esters to acids (at step D) according to standard literature procedures.

TABLE XII

ADDITIONAL EXAMPLES

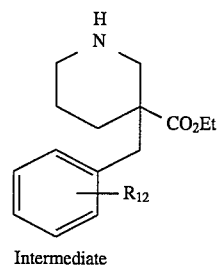

Intermediate

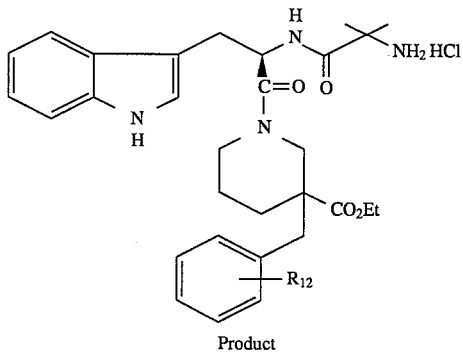

Product

| entry | $R_{12}$ | Intermediate MF FAB-MS (M + 1) | Product MF FAB-MS (M + 1) | isomer |
|---|---|---|---|---|
| 1 | o-cyano- | $C_{16}H_{20}N_2O_2$ 273 | $C_{31}H_{37}N_5O_4$ 544 | d1 d2 |
| 2 | m-cyano- | $C_{16}H_{20}N_2O_2$ 273 | $C_{31}H_{37}N_5O_4$ 544 | d1 d2 |
| 3 | p-cyano- | $C_{16}H_{20}N_2O_2$ | $C_{31}H_{37}N_5O_4$ | d1 |

TABLE XII-continued

ADDITIONAL EXAMPLES

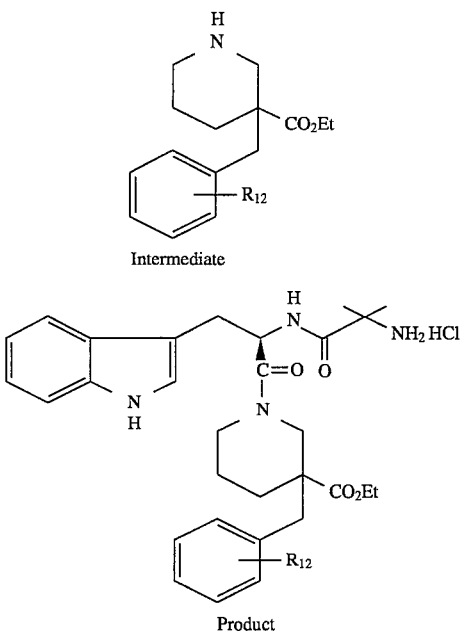

Intermediate

Product

| entry | R$_{12}$ | Intermediate MF FAB-MS (M + 1) | Product MF FAB-MS (M + 1) | isomer |
|---|---|---|---|---|
| 4 | p-NH$_2$OC— | 273 C$_{16}$H$_{22}$N$_2$O$_3$ 291 | 544 C$_{31}$H$_{37}$N$_5$O$_4$ 562 | d2 RS |
| 5 | p-EtO$_2$C— | C$_{18}$H$_{25}$NO$_4$ 320 | C$_{33}$H$_{42}$N$_4$O$_6$ 591 | d1 d2 |
| 6 | p-HO$_2$C— | | C$_{31}$H$_{38}$N$_4$O$_6$ 563 | d1 d2 |
| 7 | p-(1H-tetrazole-5-yl) | C$_{16}$H$_{21}$N$_5$O$_2$ 316 | C$_{31}$H$_{38}$N$_8$O$_4$ 587 | RS |
| 8 | m-NH$_2$OC— | C$_{16}$H$_{22}$N$_2$O$_3$ 291 | C$_{31}$H$_{37}$N$_5$O$_4$ 562 | RS |
| 9 | m-EtO$_2$C— | C$_{18}$H$_{25}$NO$_4$ 320 | C$_{33}$H$_{42}$N$_4$O$_6$ 591 | d1 d2 |
| 10 | m-HO$_2$C— | | C$_{31}$H$_{38}$N$_4$O$_6$ 563 | d1 d2 |
| 11 | m-(1H-tetrazole-5-yl) | C$_{16}$H$_{21}$N$_5$O$_2$ 316 | C$_{31}$H$_{38}$N$_8$O$_4$ 587 | RS |
| 12 | o-NH$_2$OC— | C$_{16}$H$_{22}$N$_2$O$_3$ 291 | C$_{31}$H$_{37}$N$_5$O$_4$ 562 | RS |
| 13 | o-EtO$_2$C— | C$_{18}$H$_{25}$NO$_4$ 320 | C$_{33}$H$_{42}$N$_4$O$_6$ 591 | d1 d2 |
| 14 | o-HO$_2$C— | | C$_{31}$H$_{38}$N$_4$O$_6$ 563 | d1 d2 |
| 15 | o-(1H-tetrazole-5-yl | C$_{16}$H$_{21}$N$_5$O$_2$ 316 | C$_{31}$H$_{38}$N$_8$O$_4$ 587 | RS |
| 16 | p-AcNH— | C$_{17}$H$_{24}$N$_2$O$_3$ 305 | C$_{32}$H$_{41}$N$_5$O$_5$ 576 | RS |
| 17 | m-AcNH— | C$_{17}$H$_{24}$N$_2$O$_3$ 305 | C$_{32}$H$_{41}$N$_5$O$_5$ 576 | RS |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A compound of the formula:

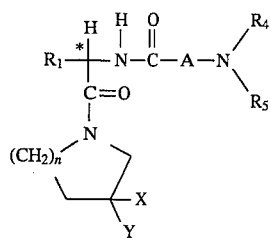

wherein:

$R_1$ is selected from the group consisting of: $C_1-C_{10}$ alkyl, aryl, aryl($C_1-C_6$ alkyl), ($C_3-C_7$ cycloalkyl)($C_1-C_6$ alkyl)-, ($C_1-C_5$ alkyl)-K—($C_1-C_5$ alkyl)-, aryl($C_0-C_5$ alkyl)-K—($C_1-C_5$ alkyl)-, and ($C_3-C_7$ cycloalkyl)($C_0-C_5$ alkyl)-K—($C_1-C_5$ alkyl)-, where K is O, $S(O)_m$, $N(R_2)C(O)$, $C(O)N(R_2)$, $OC(O)$, $C(O)O$, —$CR_2=CR_2$—, or —C≡C—, where aryl is selected from: phenyl, naphthyl, indolyl, azaindole, pyridyl, benzothienyl, benzofuranyl, thiazolyl, and benzimidazolyl, and $R_2$ and alkyl may be further substituted by 1 to 9 halogen, $S(O)_mR_{2a}$, 1 to 3 of $OR_{2a}$ or $C(O)OR_{2a}$, and aryl may be further substituted by 1 to 3 of $C_1-C_6$ alkyl, 1 to 3 of halogen, 1 to 2 of $OR_2$, methylenedioxy, —$S(O)_mR_2$, 1 to 2 of —$CF_3$, —$OCF_3$, nitro, —$N(R_2)C(O)(R_2)$, —$C(O)OR_2$, —$C(O)N(R_2)(R_2)$, -1H-tetrazol-5-yl, —$SO_2N(R_2)(R_2)$, —$N(R_2)SO_2$ phenyl, or —$N(R_2)SO_2R_2$;

$R_2$ is selected from: hydrogen, $C_1-C_6$ alkyl, and $C_3-C_7$ cycloalkyl, and where two $C_1-C_6$ alkyl groups are present on one atom, they may be optionally joined to form a $C_3-C_8$ cyclic ring;

X is selected from: —C≡N, —$(CH_2)_qN(R_2)C(O)R_2$, —$(CH_2)_qN(R_2)C(O)(CH_2)_t$aryl, —$(CH_2)_qN(R_2)SO_2(CH_2)_t$aryl, —$(CH_2)_qN(R_2)SO_2R_2$, —$(CH_2)_qN(R_2)C(O)N(R_2)(CH_2)_t$aryl, —$(CH_2)_qN(R_2)C(O)N(R_2)(R_2)$, —$(CH_2)_qC(O)N(R_2)(R_2)$, —$(CH_2)_qC(O)N(R_2)(CH_2)_t$aryl, —$(CH_2)_qC(O)OR_2$, —$(CH_2)_qC(O)O(CH_2)_t$aryl, —$(CH_2)_qOR_2$, —$(CH_2)_qOC(O)R_2$, —$(CH_2)_qOC(O)(CH_2)_t$aryl, —$(CH_2)_qOC(O)N(R_2)(CH_2)_t$aryl, —$(CH_2)_qOC(O)N(R_2)(R_2)$, —$(CH_2)_qC(O)R_2$, —$(CH_2)_qC(O)(CH_2)_t$aryl, —$(CH_2)_qN(R_2)C(O)OR_2$, —$(CH_2)_qN(R_2)SO_2N(R_2)(R_2)$, —$(CH_2)_qS(O)_mR_2$, and —$(CH_2)_qS(O)_m(CH_2)_t$aryl, where an $R_2$, $(CH_2)_q$ and $(CH_2)_t$ group may be optionally substituted by 1 to 2 $C_1-C_4$ alkyl, hydroxyl, $C_1-C_4$ lower alkoxy, carboxyl, $CONH_2$, $S(O)_mCH_3$, carboxylate $C_1-C_4$ alkyl esters, or 1H-tetrazol-5-yl, and aryl is phenyl, naphthyl, pyridyl, thiazolyl, or 1H-tetrazol-5-yl groups which may be optionally substituted by 1 to 3 halogen, 1 to 3 —$OR_2$, —$CON(R_2)(R_2)$, —$C(O)OR_2$, 1 to 3 $C_1-C_4$ alkyl, —$S(O)_mR_2$, or 1H-tetrazol-5-yl;

Y is selected from: $C_1-C_{10}$ alkyl, —$(CH_2)_t$aryl, —$(CH_2)_q(C_3-C_7$ cycloalkyl), —$(CH_2)_q$-K—($C_1-C_6$ alkyl), —$(CH_2)_q$-K—$(CH_2)_t$aryl, —$(CH_2)_q$-K—$(CH_2)_t(C_3-C_7$ cycloalkyl containing O, $NR_2$, S), and —$(CH_2)_q$-K—$(CH_2)_t(C_3-C_7$ cycloalkyl), where K is O, $S(O)_m$, $C(O)NR_2$, CH=CH, C≡C, $N(R_2)C(O)$, $C(O)NR_2$, $C(O)O$, or $OC(O)$, and where the alkyl, $R_2$, $(CH_2)_q$ and $(CH_2)_t$ groups may be optionally substituted by $C_1-C_4$ alkyl, hydroxyl, $C_1-C_4$ lower alkoxy, carboxyl, —$CONH_2$ or carboxylate $C_1-C_4$ alkyl esters, and aryl is phenyl, naphthyl, pyridyl, 1-H-tetrazol-5-yl, thiazolyl, imidazolyl, indolyl, pyrimidinyl, thiadiazolyl, pyrazolyl, oxazolyl, isoxazolyl, thiophenyl, quinolinyl, or isothiazolyl which is optionally substituted by 1 to 3 halogen, 1 to 3 —$OR_2$, —$C(O)OR_2$, —$C(O)N(R2)(R2)$, nitro, cyano, benzyl, 1 to 3 $C_1-C_4$ alkyl, —$S(O)_mR_2$, or 1H-tetrazol-5-yl;

$R_4$ and $R_5$ are independently hydrogen, $C_1-C_6$alkyl, or substituted $C_1-C_6$ alkyl where the substituents may be 1 to 5 halo, 1 to 3 hydroxy, 1 to 3 $C_1-C_{10}$ alkanoyloxy, 1 to 3 $C_1-C_6$ alkoxy, phenyl, phenyloxy, 2-furyl, $C_1-C_6$ alkoxycarbonyl, $S(O)_m(C_1-C_6$ alkyl), or $R_4$ and $R_5$ may be taken together to form —$(CH_2)_d$—$L_a(CH_2)_e$— where $L_a$ is —$C(R_2)_2$—, O, $S(O)_m$ or $N(R_2)$, d and e are independently 1 to 3 and $R_2$ is as defined above;

A is:

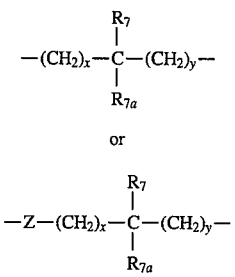

Where x and y are independently 0, 1, 2 or 3;

Z is N—$R_{6a}$ or O, where $R_{6a}$ is hydrogen or $C_1-C_6$ alkyl;

$R_7$ and $R_{7a}$ are independently hydrogen, $C_1-C_6$ alkyl, trifluoromethyl, phenyl, or substituted $C_1-C_6$alkyl where the substituents are imidazolyl, phenyl, indolyl, p-hydroxyphenyl, $OR_2$, $S(O)_mR_2$, $C(O)OR_2$, $C_3-C_7$ cycloalkyl, $N(R_2)(R_2)$, $C(O)N(R_2)(R_2)$, or $R_7$ and $R_{7a}$ may independently be joined to one or both of $R_4$ and $R_5$ groups to form an alkylene bridge between the terminal nitrogen and the alkyl portion of the $R_7$ or $R_{7a}$ groups, wherein the bridge contains 1 to 5 carbons atoms, or $R_7$ and $R_{7a}$ can be joined to one another to form $C_3-C_7$ cycloalkyl; with the proviso that if X or Y is unsubstituted phenyl, $R_4$ is hydrogen, and $R_5$ is hydrogen, then $R_7$ and $R_{7a}$ are other than hydrogen or unsubstituted $C_1-C_6$ alkyl;

m is 0, 1 or 2;

n is 2;

q is 0, 1, 2, 3, or 4;

t is 0, 1, 2, or 3;

and pharmaceutically acceptable salts and individual diastereomers thereof.

2. The compound of claim 1 wherein:

$R_1$ is selected from the group consisting of: $C_1-C_{10}$ alkyl, aryl ($C_1-C_4$ alkyl)-, $C_3-C_6$ cycloalkyl ($C_1-C_4$ alkyl)-, ($C_1-C_4$ alkyl)-K—($C_1-C_2$ alkyl)-, aryl ($C_0-C_2$ alkyl)-K—($C_1-C_2$ alkyl)-, and ($C_3-C_7$ cycloalkyl)($C_0-C_2$ alkyl)-K—($C_1-C_2$ alkyl)-, where K is O, $S(O)_m$, $OC(O)$, or $C(O)O$, and the alkyl groups may be further substituted by 1 to 7 halogen, $S(O)_mR_2$, 1 to 3 $OR_2$, and aryl is phenyl, naphthyl, indolyl, pyridyl, benzimidazolyl, azaindoleyl, benzothienyl or benzofuranyl which may be further substituted by 1–2 $C_1-C_4$ alkyl, 1 to 2halogen, 1 to 2—$OR_2$, —$S(O)_mR_2$, or —$C(O)OR_2$;

$R_2$ is hydrogen, $C_1-C_6$ alkyl, or $C_3-C_7$ cycloalkyl, and where two $C_1-C_6$ alkyl groups are present on one atom they may be optionally joined to form a $C_4$-$C_7$ cyclic ring;

X is selected from: —$(CH_2)_qN(R_2)C(O)R_2$—$(CH_2)_qN(R_2)C(O)(CH_2)_t$aryl, —$(CH_2)_qN(R_2)C(O)OR_2$, —$(CH_2)_qN(R_2)SO_2(CH_2)_t$aryl, —$(CH_2)_qN(R_2)SO_2R_2$, —$(CH_2)_qN(r_2)C(O)N(R_2)_t$aryl, —$(CH_2)_qN(R_2)C(O)N(R_2)(R_2)$, —$(CH_2)_qC(O)N(R_2)(R_2)$, —$(CH_2)_qC(O)N(R_2)(CH_2)_t$aryl, —$(CH_2)_qC(O)OR_2$, —$(CH_2)_qC(O)O(CH_2)_t$aryl, —$(CH_2)_qOC(O)R_2$, —$(CH_2)_qOC(O)(CH_2)_t$aryl, —$(CH_2)_qS(O)mR_2$, and —$(CH_2)_qS(O)m(CH_2)_t$aryl, where an $R_2$ group may be optionally substituted by hydroxyl, carboxyl, $CONH_2$, $S(O)_mCH_3$, carboxylate $C_1$-$C_4$ alkyl esters, or tetrazole, and aryl is phenyl, napthyl, pryidyl or 1-H-tetrazolyl which may be optionally substituted by 1 to 2 halogen, 1 to 2 —$OR_2$, —$CONH_2$, —$C(O)OR_2$, 1 to 3 $C_1$-$C_4$ alkyl, —$S(O)_mR_2$, or 1H-tetrazole-5-yl;

Y is selected from: $C_1$-$C_8$ alkyl, $(CH_2)_t$aryl, —$(CH_2)_q(C_5$-$C_6$ cycloalkyl), —$(CH_2)_q$—K—$(C_1$-$C_6$ alkyl), —$(CH_2)_q$—K—$(CH_2)_t$aryl, —$(CH_2)_q$—K—$(CH_2)_t(C_3$-$C_7$ cycloalkyl containing O, $NR_2$or S), and —$(CH_2)_q$—K—$(CH_2)_t(C_5$-$C_6$ cycloalkyl), where K is O or $S(O)m$ and where the alkyl groups may be optionally substituted by hydroxyl, carboxyl, $CONH_2$, carboxylate $C_1$-$C_4$ alkyl esters or 1H-tetrazole-5-yl and aryl is phenyl, naphthyl, pyridyl, 1-H-tetrazol, thiazolyl, imidazolyl, indolyl, pyrimidinyl, thiadiazolyl, pyrazolyl, oxazolyl, isoxazolyl, or thiopheneyl which is optionally substituted by 1 to 3 halogen, 1 to 3 —$OR_2$, —$C(O)OR_2$, —$C(O)N(R_2)$, cyano, 1 to 2 $C_1$-$C_4$ alkyl, benzyl, —$S(O)_mR_2$, or 1H-tetrazol-5-yl;

$R_4$ and $R_5$ are independently hydrogen, $C_1$-$C_6$ alkyl, or substituted $C_1$-$C_6$ alkyl where the substituents may be 1 to 5 halo, 1 to 3 hydroxyl, $S(O)m$ ($C_1$-$C_6$ alkyl) or phenyl;

A is:

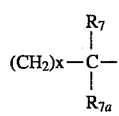

where x is 0, or 1;

$R_7$ and $R_{7a}$ are independently hydrogen $C_1$-$C_6$ alkyl, trifluoromethyl, phenyl, substituted $C_1$-$C_6$ alkyl where the substituents are imidazolyl, phenyl, indolyl, p-hydroxyphenyl, $OR_2$, $S(O)mR_2$, $C(O)OR_2$, $C_5$-$C_7$ cycloalkyl, —$N(R_2)(R_2)$, —$C(O)N(R_2)(R_2)$;

or $R_7$ and $R_{7a}$ can independently be joined to one of $R_4$ or $R_5$ to form an alkylene bridge between the terminal nitrogen and the alkyl portion of $R_7$ or $R_{7a}$ groups to form 5 or 6 membered rings; or $R_7$ and $R_{7a}$ can be joined to one another to form a $C_3$ cycloalkyl;

with the proviso that if X or Y is unsubstituted phenyl, $R_4$ is hydrogen, and $R_5$ is hydrogen, then $R_7$ and $R_{7a}$ are other than hydrogen or unsubstituted $C_1$-$C_6$ alkyl;

n is 2;

m is 0, 1, or 2;

q is 0, 1, 2, or 3;

t is 0, 1, 2, or 3;

and pharmaceutically acceptable salts and individual diastereomers thereof.

3. The compound of claim 1 of the formula:

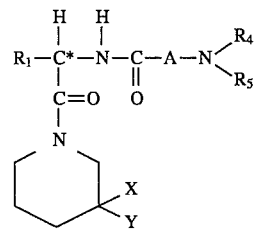

wherein:

$R_1$ is selected from the group consisting of: $C_1$-$C_{10}$ alkyl, aryl ($C_1$-$C_3$ alkyl)-, ($C_3$-$C_7$ cycloalkyl)($C_1$-$C_3$ alkyl)-, and aryl ($C_0$-$C_1$ alkyl)—K—($C_1$-$C_2$ alkyl)-, where K is O or $S(O)_m$ and the aryl is phenyl, pyridyl, naphthyl, indolyl, azaindolyl, or benzimidazolyl which is optionally substituted by 1–2 $C_1$-$C_4$ alkyl, 1 to 2 halogen, 1 to 2 $OR_2$, $S(O)_m$ $R_2$, or $C(O)OR_2$;

$R_2$ is hydrogen, $C_1$-$C_6$ alkyl, or $C_3$-$C_7$ cycloalkyl, and where two $C_1$-$C_6$ alkyl groups are present on one atom they may be optionally joined to form a $C_5$-$C_7$ cyclic ring;

X is selected from: —$(CH_2)_qN(R_2)C(O)R_2$, —$(CH_2)_qN(R_2)C(O)(CH_2)_t$aryl, —$(CH_2)_qN(R_2)SO_2(CH_2)_t$aryl, —$(CH_2)_qN(R_2)SO_2R_2$, —$(CH_2)_qN(R_2)C(O)N(R_2)$ $(CH_2)_t$aryl, —$(CH_2)_qN(R_2)C(O)N(R_2)(R_2)$, —$(CH_2)_qC(O)N(R_2)(R_2)$, —$(CH_2)_qN(R_2)C(O)OR_2$, —$(CH_2)_qC(O)N(R_2)$ $(CH_2)_t$aryl, —$(CH_2)_qC(O)OR_2$, —$(CH_2)_qC(O)O(CH_2)_t$aryl, —$(CH_2)_qOC(O)R_2$, —$(CH_2)_qOC(O)(CH_2)_t$aryl, —$(CH_2)_qS(O)_mR_2$, and —$(CH_2)_qS(O)_m(CH_2)_t$aryl, where an $R_2$ group may be optionally substituted by hydroxyl, carboxyl, —$CONH_2$, —$S(O)_mCH_3$, carboxylate $C_1$-$C_4$ alkyl esters or tetrazole and aryl is phenyl, naphthyl or pyridyl which may be further substituted by 1–2 halogen, 1 to 2 $OR_2$, $C(O)OR_2$, 1 to 3 $C_1$-$C_4$ alkyl, $S(O)_mR_2$, or 1H-tetrazole-5-yl;

Y is selected from: $C_1$-$C_8$ alkyl, $(CH_2)_t$aryl, —$(CH_2)_qC_5$-$C_7$ cycloalkyl, —$(CH_2)_q$—K—$(C_1$-$C_6$ alkyl), —$(CH_2)_q$—K—$(CH_2)_t$aryl, and —$(CH_2)_q$—K—$(CH_2)_t(C_5$-$C_6$ cycloaklyl), where K is $S(O)_m$ and where the alkyl groups may be optionally substituted by hydroxyl, carboxyl, $CONH_2$, carboxylate $C_1$-$C_4$ alkyl esters or 1H-tetrazole-5-yl and aryl is phenyl, napthyl, pyridyl, thiazolyl, thiopheneyl, pyrazolyl, oxazolyl, isoxazolyl or imidazolyl which may be optionally substituted by 1 to 2 halogen, 1 to 2 $OR_2$, 1 to 2—$N(R_2)$ $(R_2)$, $CO(OR_2)$, 1 to 2 $C_1$-$C_4$ alkyl, $S(O)_mR_2$, or 1H-tetrazol-5-yl;

$R_4$ and $R_5$ are independently hydrogen, $C_1$-$C_4$ alkyl, or substituted $C_1$-$C_3$ alkyl where the substituents may be 1 to 2 hydroxyl;

A is

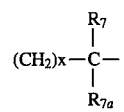

where x is 0, or 1;

$R_7$ and $R_{7a}$ are independently hydrogen, $C_1$-$C_6$ alkyl, phenyl, substituted $C_1$-$C_6$ alky wherein the substitutent is imidixolyl, phenyl, indolyl, p-hydroxyphenyl, $OR_2$, $S(O)_mR_2$, or $R_7$ and $R_{7a}$ may be joined to one another to form a $C_3$ cycloalkyl; with the proviso that if X or Y is unsubstituted phenyl, $R_4$ is hydrogen, and $R_5$ is hydrogen, then $R_7$ and $R_{7a}$ are other than hydrogen or unsubstituted $C_1$-$C_6$ alkyl;

m is 0, 1, or 2:

q is 0, 1, 2, or 3;

t is 0, 1, 2, or 3;

and pharmaceutically acceptable salts and individual diastereomers thereof.

4. The stereospecifically defined compound of claim 1 of the formula:

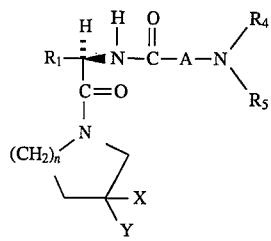

wherein $R_1$, $R_4$, $R_5$, A, X, Y, and n are as defined in claim 1.

5. A compound of the formula:

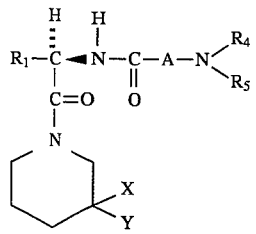

wherein:

$R_1$ is selected from the group consisting of:

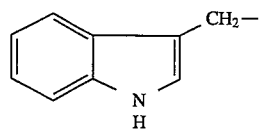

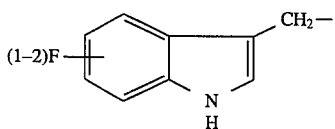

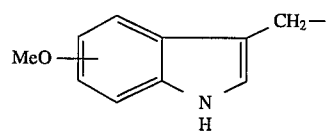

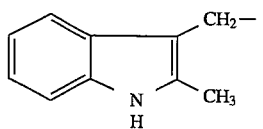

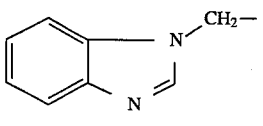

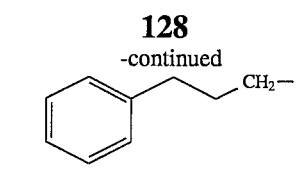

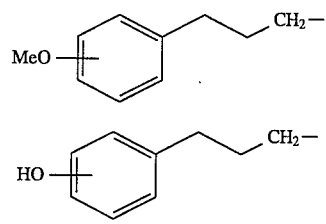

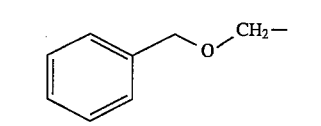

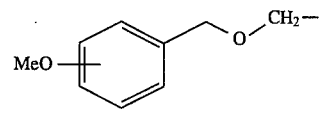

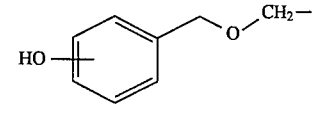

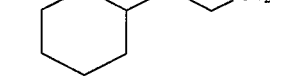

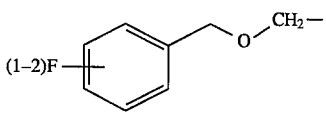

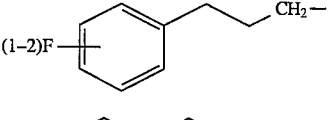

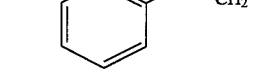

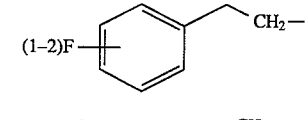

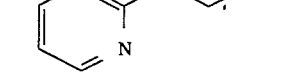

or their regioisomers where not specified;

$R_2$ is hydrogen, $C_1$-$C_6$ alkyl, or $C_3$-$C_7$ cycloalkyl and where two $C_1$-$C_6$ alkyl groups are present on one atom they may be optionally joined to form a $C_5$-$C_7$ cyclic ring;

X is selected from the group consisting of:

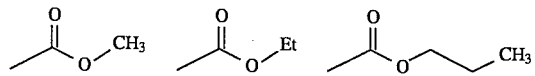

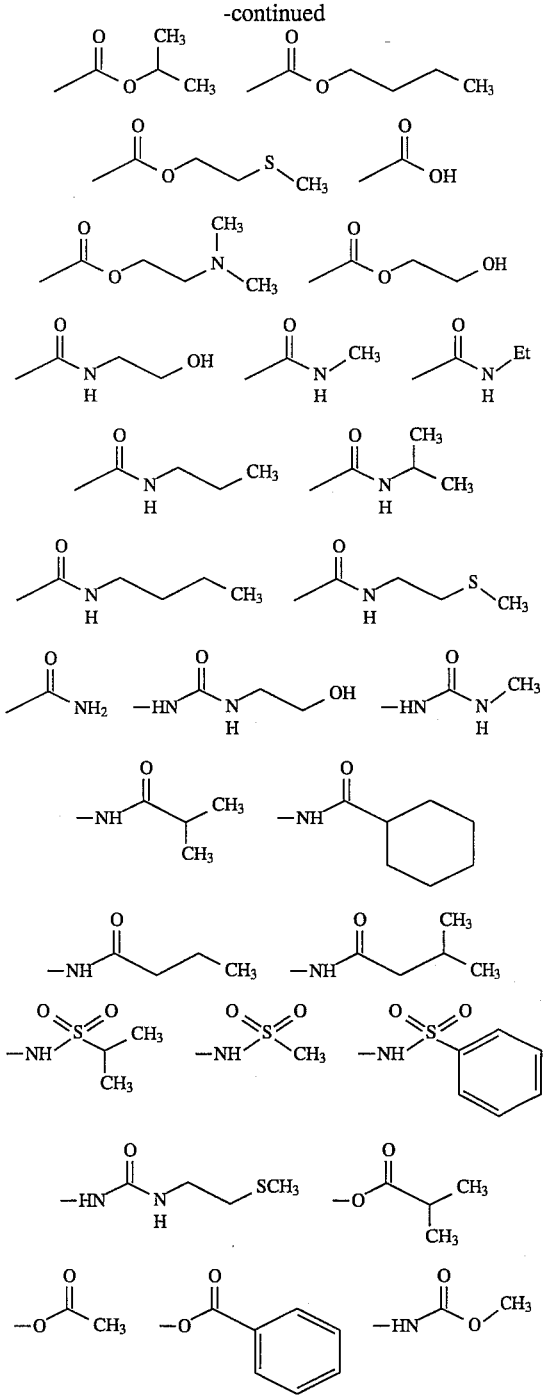
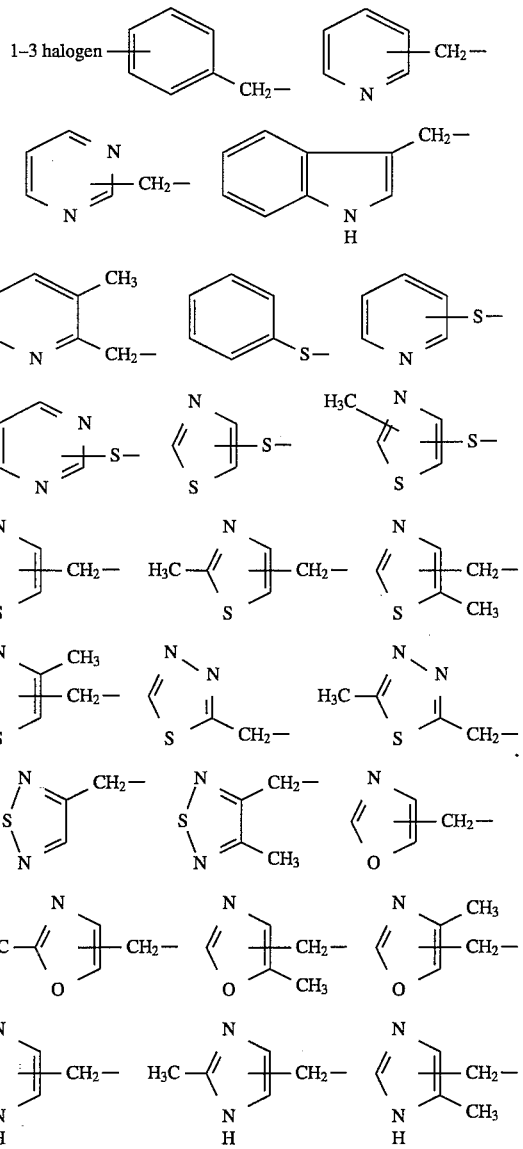
or their regioisomers whereof where not specified
A is selected from the group consisting of:
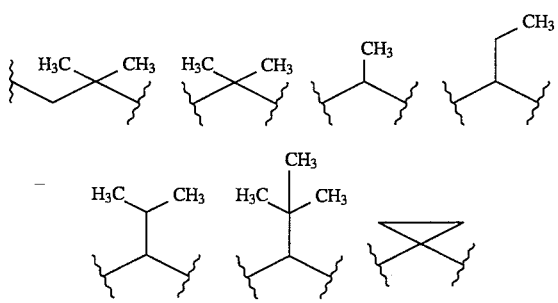
Y is selected from the group consisting of: hydrogen
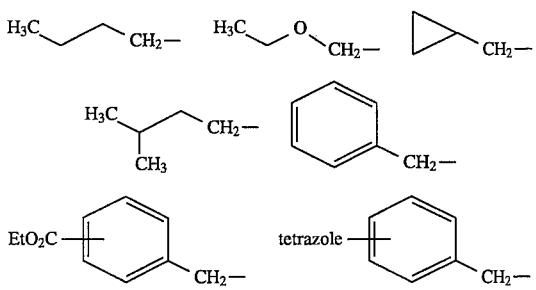

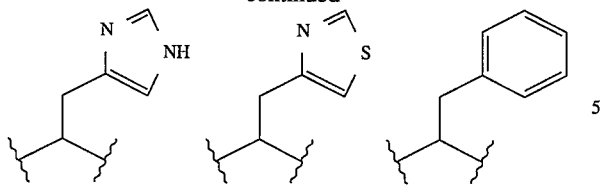
$R_4$ and $R_5$ are independently selected from the group consisting of:
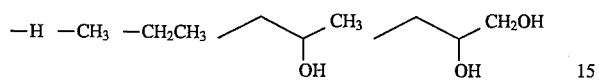
and pharmaceutically acceptable salts and individual diastereomers thereof.
6. A compound which is selected from the group consisting of:
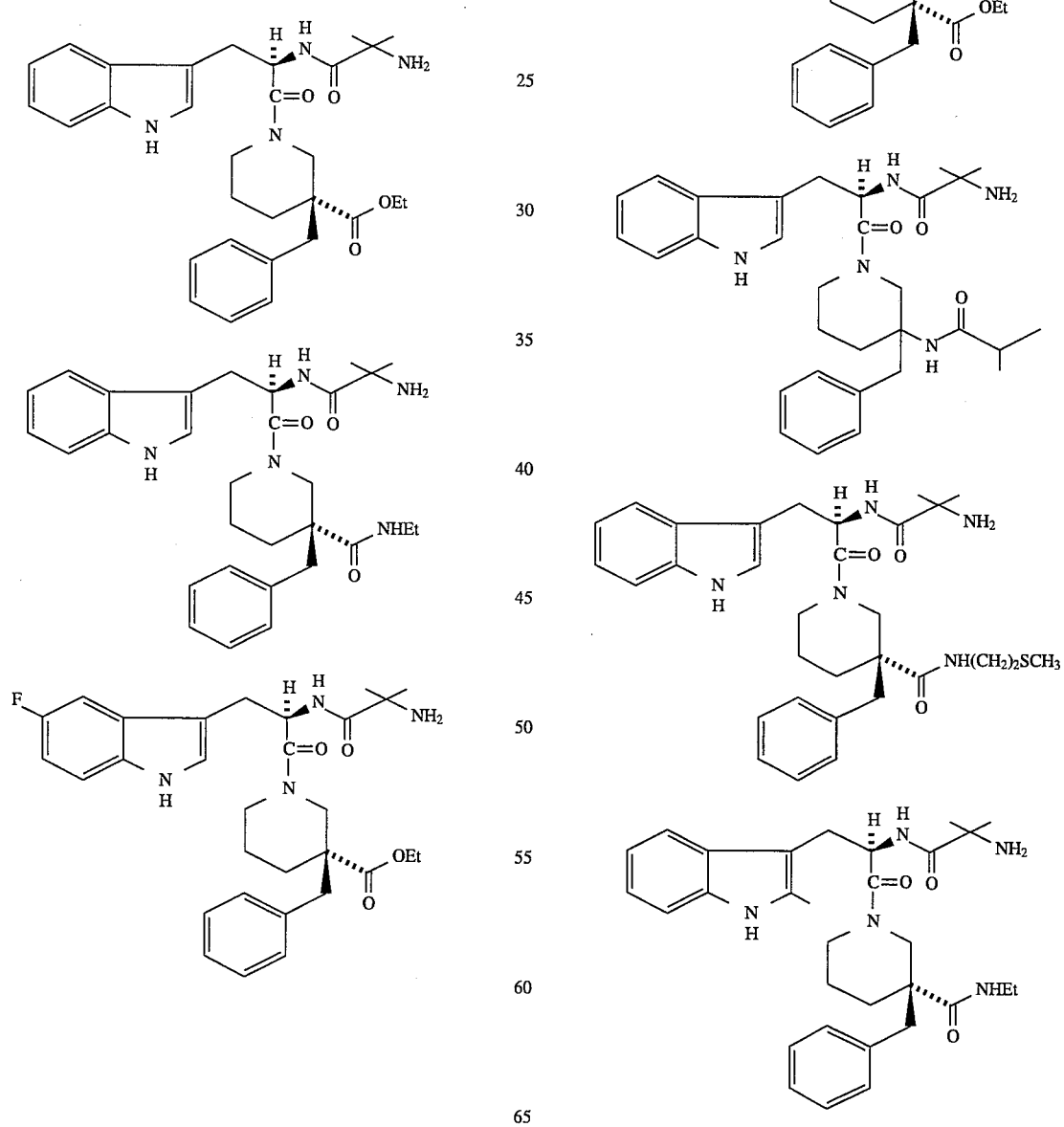

133
-continued
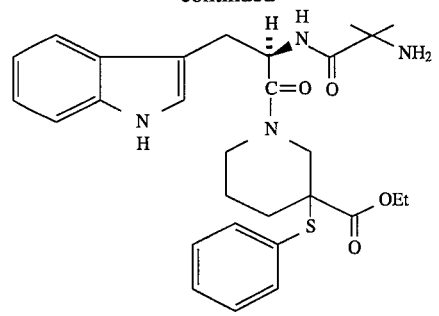
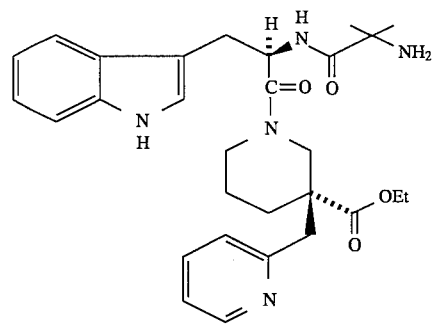
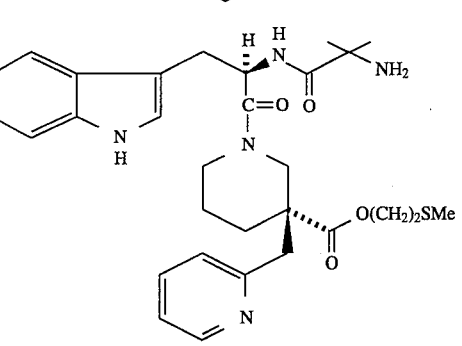
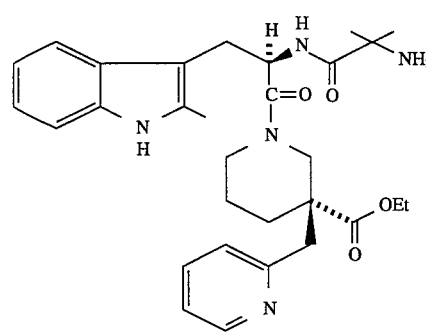
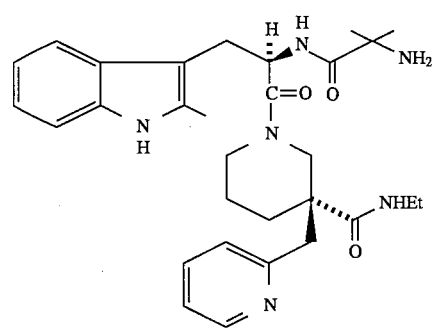
134
-continued
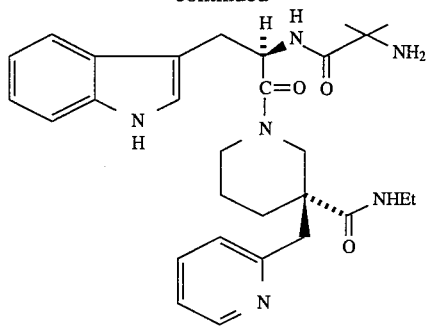
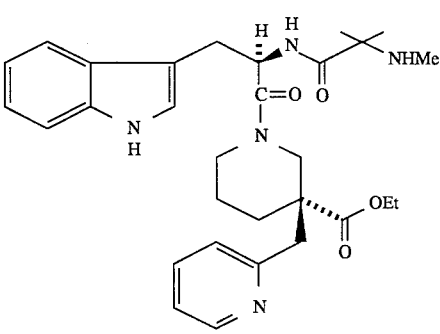
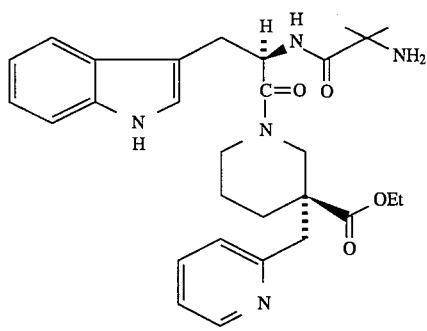
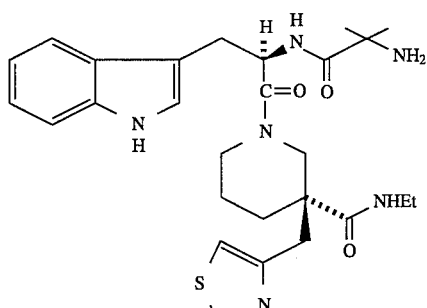
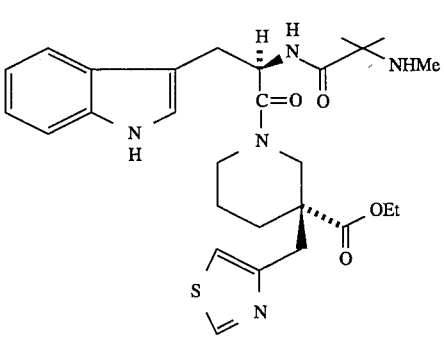

135
-continued
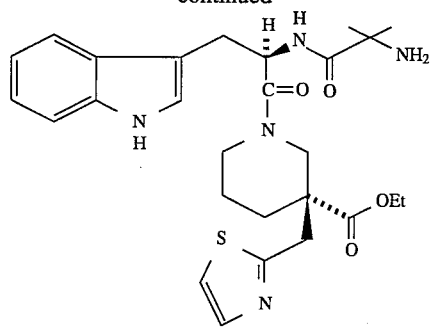
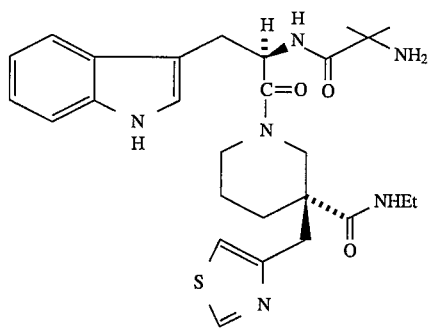
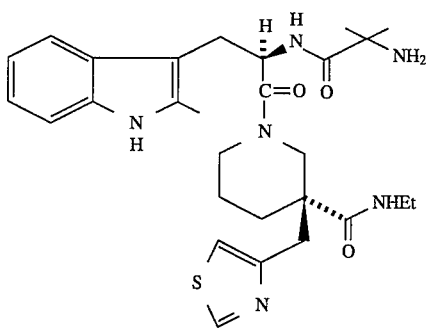
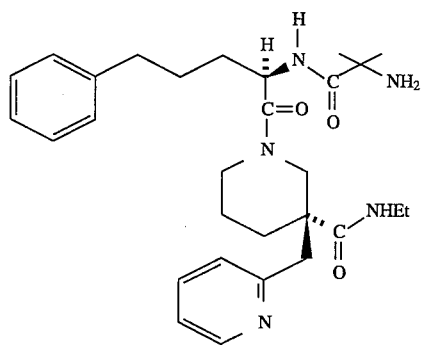
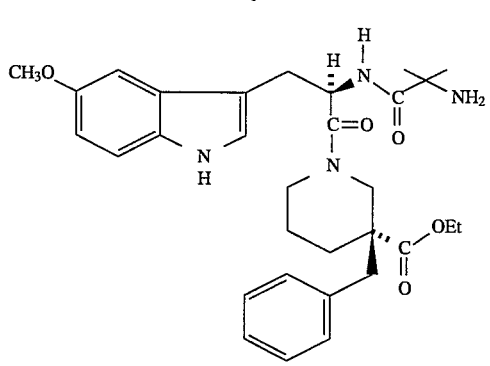
136
-continued
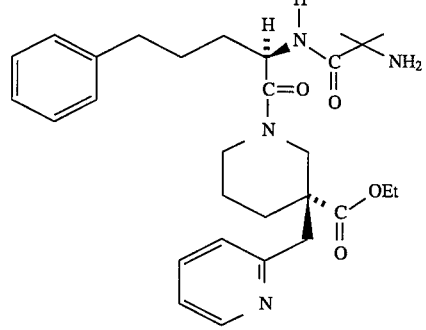
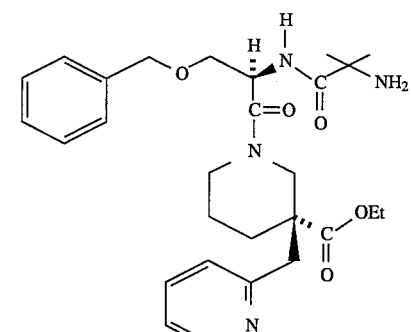
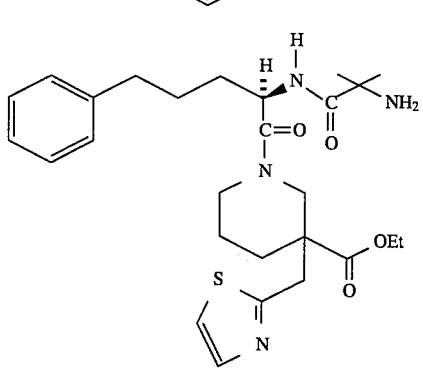
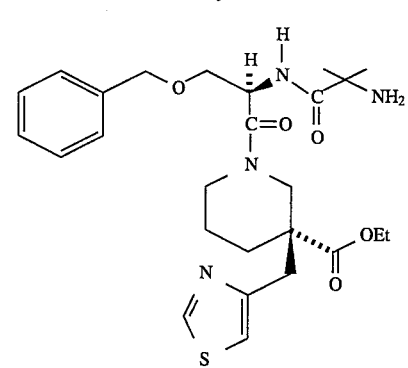

137
-continued

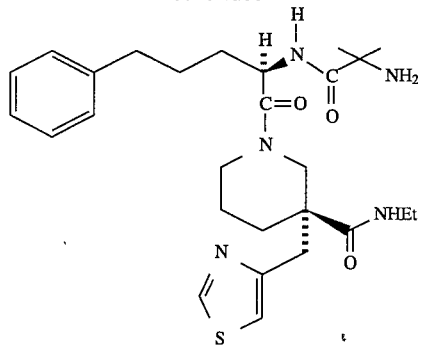

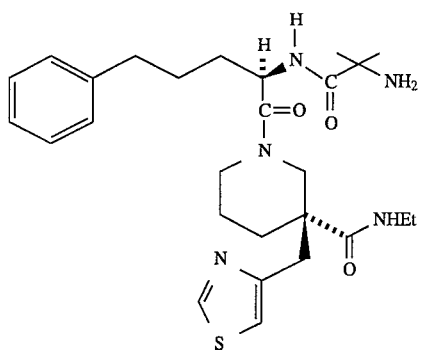

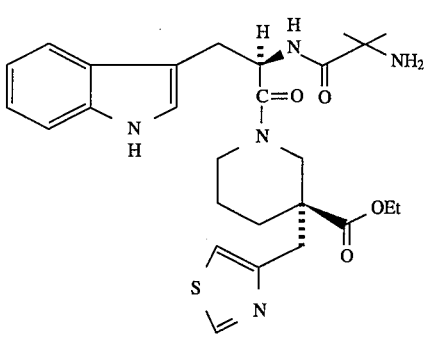

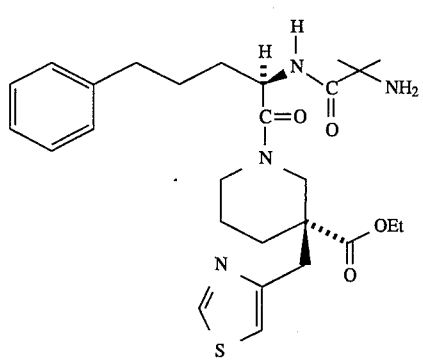

138
-continued

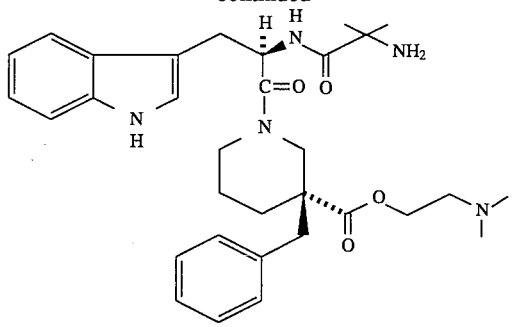

and their pharmaceutically acceptable salts and individual diastereomers thereof where not otherwise specified.

7. A compound which is:

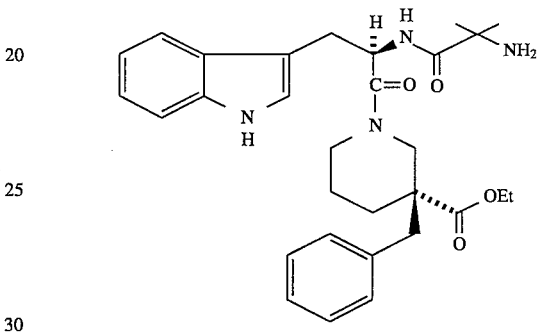

or a pharmaceutically acceptable salt thereof.

8. A compound which is:

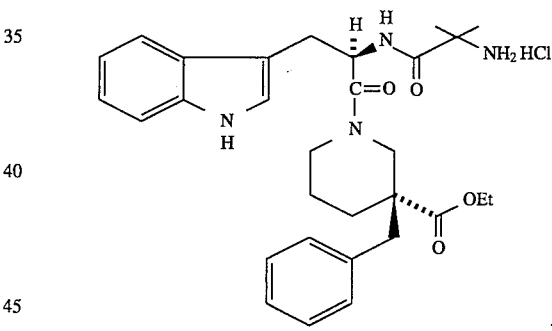

9. A composition useful for increasing the endogenous production or release of growth hormone in a human or an animal which comprises an inert carrier and an effective amount of the compound of claim 1.

10. A method for increasing levels of endogenous growth hormone in a human or an animal which comprises administering to such human or animal an effective amount of the compound of claim 1.

* * * * *